US012778635B2

(12) United States Patent
Samchukov et al.

(10) Patent No.: US 12,778,635 B2
(45) Date of Patent: Nov. 3, 2026

(54) BONE TRANSPORT SYSTEM AND METHODS

(71) Applicants: ORTHOFIX S.R.L., Bussolengo (IT); Texas Scottish Rite Hospital for Children, Dallas, TX (US)

(72) Inventors: Mikhail L. Samchukov, Coppell, TX (US); Andrea Ottoboni, Giacciano con Baruchella (IT); Daniele Venturini, Povegliano Veronese (IT); John David Ross, Ovilla, TX (US); Karen Divita Standefer, Flower Mound, TX (US); Alexander Cherkashin, Flower Mound, TX (US)

(73) Assignees: Orthofix S.R.L, Bussolengo (IT); Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 18/733,649

(22) Filed: Jun. 4, 2024

(65) Prior Publication Data

US 2024/0407807 A1 Dec. 12, 2024

Related U.S. Application Data

(60) Provisional application No. 63/506,888, filed on Jun. 8, 2023.

(51) Int. Cl.

| | |
|---|---|
| ***A61B 17/66*** | (2006.01) |
| ***A61B 17/17*** | (2006.01) |
| ***A61B 17/56*** | (2006.01) |
| ***A61B 17/60*** | (2006.01) |
| ***A61B 17/62*** | (2006.01) |

(Continued)

(52) U.S. Cl.
CPC .......... *A61B 17/66* (2013.01); *A61B 17/6425* (2013.01); *A61B 17/8866* (2013.01); (Continued)

(58) Field of Classification Search
CPC ... A61B 17/17; A61B 17/171; A61B 17/1739; A61B 17/64; A61B 17/645; (Continued)

(56) References Cited

U.S. PATENT DOCUMENTS

| | | | | |
|---|---|---|---|---|
| 6,617,534 B2 * | 9/2003 | Goff | ..................... | B60Q 1/1476 200/61.54 |
| 2020/0069334 A1 * | 3/2020 | Moradi | .............. | A61B 17/6425 |

FOREIGN PATENT DOCUMENTS

| | | |
|---|---|---|
| CN | 203183002 U | 9/2013 |
| CN | 105167828 A | 12/2015 |

(Continued)

OTHER PUBLICATIONS

Shuanji Ou et al., "Transverse Tibial Bone Transport Enhances Distraction Osteogenesis and Vascularization in the Treatment of Diabetic Foot", 2022 The Authors, Orthopaedic Surgery Published by Tianjin Hospital and John Wiley & Sons Australia, Ltd., Clinical Article, vol. 14, No. 9, Sep. 2022, pp. 2170-2179.

*Primary Examiner* — Marcela I. Shirsat
(74) *Attorney, Agent, or Firm* — Haynes and Boone, LLP

(57) ABSTRACT

Systems, methods, and devices for transverse bone transport. A transverse bone transport system may include a template for measuring and cutting a segment of the bone and a distractor for moving the segment. The template may include a plate including an opening configured to fit a pin sleeve. A channel may extend from the opening in the plate to a side of the plate. The distractor may include a first beam, a second beam, and an actuator including a knob configured to rotate in a first direction to increase a distance between the first beam and the second beam and in a second direction to decrease a distance between the first beam and the second beam.

31 Claims, 45 Drawing Sheets

(51) Int. Cl.

*A61B 17/64* (2006.01)
*A61B 17/88* (2006.01)
*A61B 17/90* (2006.01)

(52) U.S. Cl.

CPC ......... *A61B 17/171* (2013.01); *A61B 17/1739* (2013.01); *A61B 2017/564* (2013.01); *A61B 17/60* (2013.01); *A61B 2017/606* (2013.01); *A61B 17/62* (2013.01); *A61B 17/645* (2013.01); *A61B 17/6458* (2013.01); *A61B 17/6466* (2013.01); *A61B 17/6475* (2013.01); *A61B 17/6491* (2013.01); *A61B 17/8872* (2013.01); *A61B 17/8897* (2013.01); *A61B 17/90* (2021.08)

(58) Field of Classification Search

CPC ............ A61B 17/6466; A61B 17/6425; A61B 17/6491; A61B 17/60; A61B 17/6475; A61B 17/66; A61B 17/8866; A61B 17/1728; A61B 17/62; A61B 17/6458; A61B 17/8875; A61B 17/88; A61B 17/8869; A61B 17/8872; A61B 17/8897; A61B 2017/606; A61B 2017/564

USPC .................. 606/96, 104, 103, 105, 86 R, 90

See application file for complete search history.

(56) References Cited

FOREIGN PATENT DOCUMENTS

| | | | | | |
|---|---|---|---|---|---|
| CN | 106108992 | A | * 11/2016 | ......... A61B 17/6466 |
| CN | 211433237 | U | 9/2020 | |
| EP | 3410964 | A1 | 12/2018 | |
| WO | 2024032985 | A1 | 2/2024 | |

* cited by examiner

BONE TRANSPORT SYSTEM AND METHODS

CROSS-REFERENCE TO RELATED APPLICATIONS

The present application claims the benefit of U.S. Provisional Application No. 63/506,888, filed Jun. 8, 2023, which is incorporated by reference herein in its entirety.

TECHNICAL FIELD

The present disclosure relates generally to bone transport systems, and in particular to templates, distractors, and pins used in bone transport systems and methods of using bone transport systems.

BACKGROUND

Foot ulcers are a common problem for patients with poorly controlled diabetes or with peripheral arterial disease. Transverse bone transport is a method of treating those foot ulcers. During transverse bone transport, a segment of the bone in the leg where the ulcer is located, often the tibia, is cut and moved away from or transverse to the axis of the bone. This method may also be known as the Ilizarov technique. By providing continuous tension to the bone tissue, transverse bone transport may stimulate growth of new vessels in the tissues between the transport and base portions of the bone thereby increasing blood circulation and promoting active neovascularization in the bone and the entire extremity. This may improve healing of the diabetic and peripheral arterial disease foot ulcer in the lower part of the extremity.

However, transverse bone transport systems may be difficult or inconvenient for the surgeon to apply and for the patient to use. Moreover, transverse bone transport procedures may cause pain or discomfort to the patient. Therefore, improved transverse bone transport systems are needed.

SUMMARY

The present disclosure describes devices, systems, and methods for transverse bone transport. Some embodiments according to the present disclosure include a template to create a transport bone segment and attach that bone segment to a transverse bone transport device for a transverse bone transport. The template may include a plate including a top surface, a bottom surface, a first side, a second side opposite the first side, a first opening extending from the top surface to the bottom surface, and a channel extending between the top surface and the bottom surface and extending between the first opening and the first side of the plate. The width of the channel may be less than the width of the first opening. The template may also include a pin sleeve configured to fit into the first opening. The outer width of the pin sleeve may be greater than the width of the channel.

In some embodiments, the template may include a wire sleeve configured to fit into the pin sleeve. In some embodiments, the outer width of the wire sleeve may be smaller than an inner width of the pin sleeve. In some embodiments, the template may include a drill bit sleeve configured to fit into the pin sleeve. In some embodiments, the outer width of the drill bit sleeve may be smaller than an inner width of the pin sleeve. In some embodiments the first opening may be angled towards an end of the plate such that the pin sleeve is angled with respect to the top surface of the plate when the pin sleeve is disposed in the first opening. In some embodiments, the plate may further include a first end extending between the first side and the second side, a second end opposite the first end extending between the first side and the second side, and a plurality of corners between the first side, the first end, the second side, and the second end. In some embodiments, the template may further include a drill guide including a guide axis, a guide opening aligned with the guide axis, and an alignment structure configured to engage a first corner of the plurality of corners. The alignment structure may include a first guide wall configured to engage one of the first side or the second side, a second guide wall configured to engage one of the first end or the second end, and a base surface configured to engage the top surface. When the alignment structure engages the first corner of the plate, the guide axis may be angled relative to the top surface of the plate.

In some embodiments, the template also includes a second opening extending from the top surface to the bottom surface, a second channel extending between the top surface and the bottom surface and extending between the second opening and the first side of the plate; and a guide pin aperture extending from the top surface to the bottom surface and disposed on a longitudinal axis between the first opening and the second opening. In some embodiments, the plate also includes an extension extending upward around at least a portion of the first opening.

Some embodiments of the present disclosure include a distractor mechanism or distractor for a transverse bone transport system. The distractor may include a first beam that may include a first opening and a first moveable half-pin holder. The distractor may also include a second beam that may include a second opening and a second moveable half-pin holder. The length of the second beam may be larger than the length of the first beam. The first moveable half-pin holder and the second moveable half-pin holder may be longitudinally and radially displaced. The distractor may also include an actuator that includes a knob and a threaded rod disposed within the first beam and the second beam. The knob may be configured to rotate in a first direction to increase a distance between the first beam and the second beam and in a second direction to decrease a distance between the first beam and the second beam.

In some embodiments, the actuator may be rotatable through a plurality of discrete rotation positions. In some embodiments, each of the plurality of discrete positions may be located at set distance from the neighboring discrete positions. In some embodiments, the set distance may correspond to a discrete lateral distance between the first beam and the second beam.

In some embodiments, the first moveable half-pin holder and the second moveable half-pin holder may be configured to pivot between a plurality of angular positions. In some embodiments, the first moveable half-pin holder may be configured to hold a first pin, where the first moveable half-pin holder may be configured to tighten around the first pin such that the first pin is held in a first angular position of the plurality of angular positions. In some embodiments, the second moveable half-pin holder may be configured to hold a second pin, where the second moveable half-pin holder may be configured to tighten around the second pin such that the second pin is held in a second angular position of the plurality of angular positions. In some embodiments, the first angular position and the second angular position are different. In some embodiments, the threaded rod may be threadedly received in the second beam such that the actuator may be configured to move the first beam relative to the second beam. In some embodiments, the distractor may also include a support post coupled to at least one of the first beam or the second beam and disposed proximate the threaded rod.

In some embodiments, the first movable half pin holder and the second movable half pin holder may include a threaded shaft placed into the first opening and the second opening of the first beam and the second beam and tightened by the first half pin holder nut and the second half pin holder nut in such that the pin is held in one angular position of the plurality of angular positions. In some embodiments, the first beam and second beam may include a slotted first opening and a second opening for receiving pin holders. In some embodiments, the vertical slot may include an outer spherical surface adjacent the slot with a convex surface for engagement with a movable half pin holder on one side and a matching concave surface for engaging the tightening nut on the opposite side. In some embodiments, the first half pin holder tightening nut and the second half pin holder tightening nut may include a convex surface matching the concave surface of the vertically slotted spherical portion of the first beam and the second beam. In some embodiments, the first beam and the second beam may include a horizontally or obliquely slotted opening for movable half pin holder providing flexibility in distance between the distraction mechanism and the skin.

Some embodiments of the present disclosure may include a kit for a transverse bone transport system. The kit may include a template, a distractor, and a plurality of pins. The template may also include a plate including a top surface, a bottom surface, a first side, a second side opposite the first side, an opening extending from the top surface to the bottom surface, and a channel extending between the top surface and the bottom surface and extending between the opening and the first side of the lower plate. The width of the channel may be less than the width of the opening. The template may also include a pin sleeve configured to fit into the opening. The outer width of the pin sleeve may be greater than the width of the channel. The distractor may include a first beam that may include a first opening and a first moveable half-pin holder. The distractor may also include a second beam that may include a second opening and a second moveable half-pin holder. The length of the second beam may be larger than the length of the first beam. The first beam and the second beam may be longitudinally displaced. The distractor may also include an actuator that includes a knob and a threaded rod disposed within the first beam and the second beam. The knob may be configured to rotate in a first direction to increase a distance between the first beam and the second beam and in a second direction to decrease a distance between the first beam and the second beam.

In some embodiments, the plate may further include a first end extending between the first side and the second side, a second end opposite the first end extending between the first side and the second side, and a plurality of corners between the first side, the first end, the second side, and the second end. In some embodiments, the template may further include a drill guide including a guide axis, a guide opening aligned with the guide axis, and an alignment structure configured to engage a first corner of the plurality of corners. The alignment structure may include a first guide wall configured to engage one of the first side or the second side, a second guide wall configured to engage one of the first end or the second end, and a base surface configured to engage the top surface. When the alignment structure engages the first corner of the plate, the guide axis may be angled relative to the top surface of the plate. In some embodiments, the width of at least one pin of the plurality of pins is smaller than the width of the channel.

Some embodiments of the present disclosure may include a method of performing bone transport. The method may include positioning a template over a transport segment of a bone, where the template includes a plate having a top surface, a bottom surface opposite the top surface, a first side, and a second side opposite the first side. The method may also include retaining the template in a first position relative to the bone. The method may also include utilizing the template to form a plurality of holes in the bone adjacent at least the first and second sides. The method may also include cutting a transport segment from the bone using the plurality of holes.

In some embodiments, utilizing the template to form a plurality of holes in the bone may include engaging the template with a drill guide and passing a drill bit through the drill guide to form the plurality of holes. In some embodiments, the template may include a guide pin aperture and the method may further include inserting a first guide wire through the guide pin aperture.

In some embodiments, the method may further include inserting, after positioning the template over the transport segment, a half-pin through a pin sleeve attached to the template and into the transport segment. In some embodiments, the template may include a first opening to receive the pin sleeve and the pin sleeve may include a second opening. In some embodiments, the template may include a wire sleeve that is configured to be inserted into the second opening of the pin sleeve and comprises a third opening. In some embodiments, the method may further include inserting, before inserting the half-pin through the pin sleeve and into the transport segment, a second guide wire through the third opening of the wire sleeve and into the transport segment of the bone. In some embodiments, the method may further include passing, after inserting a second guide wire through the third opening of the wire sleeve, a skin flap over the template and second guide wire, with the wire sleeve extending through a hole in the skin flap. In some embodiments, the method may further include removing, after inserting the second guide wire through the third opening of the wire sleeve and into the transport segment of the bone, the second guide wire and the wire sleeve. In some embodiments, removing, after cutting the transport segment, the pin sleeve upwards along a longitudinal axis of the half-pin. In some embodiments, the method may further include removing, after removing the pin sleeve, the plate sideways along an axis generally perpendicular to the longitudinal axis of the half-pin.

Some embodiments of the present disclosure may include a distractor for a transverse bone transport system. The distractor may include a first beam including a first opening and a first moveable half-pin holder and a second beam including a second opening and a second moveable half-pin holder. A length of the second beam may be larger than a length of the first beam. The first moveable half-pin holder and the second moveable half-pin holder may be longitudinally and radially displaced. The distractor may also include a motorized actuator that includes a threaded rod disposed within the first opening of the first beam and the second opening of the second beam and a motor operably coupled to the threaded rod. The motor may be configured to rotate the threaded rod in a first direction to increase a distance between the first beam and the second beam and in a second direction to decrease a distance between the first beam and the second beam.

In some embodiments, the actuator may include a first gear coupled to the motor such that the motor is configured to rotate the first gear and a second gear in contact with the first gear such that the first gear is configured to rotate the second gear as the motor rotates the first gear. The second gear may be coupled to the threaded rod such that the second gear is configured to rotate the threaded rod as the first gear rotates the second gear. In some embodiments, the distractor may also include a power supply and a processor circuit operably coupled to at least one of the motor or the power supply, wherein the processor circuit is configured to control the at least one of the motor or the power supply. In some embodiments, the distractor may also include or more sensors configured to obtain measurement data and transmit the data to the processor circuit. In some embodiments, the processor circuit may be configured to receive the obtained measurement data from the one or more sensors. In some embodiments, the processor circuit may include an artificial intelligence program that uses the obtained measurement data to generate a treatment protocol. In some embodiments, the processor circuit may be configured to control the at least one of the power supply or motor according to the generated treatment protocol. In some embodiments, the processor circuit may be configured to transmit the obtained measurement data to a computer system. In some embodiments, the processor circuit may control the at least one of the or motor according to a sinusoidal rate of distraction and compression. In some embodiments, the transverse bone transport device may include multiple sensors measuring blood volume, speed of blood flow, vascularization/neovascularization, strain, or displacement.

In some embodiments, the distractor mechanism for transverse bone transport may be used in combination with a circular or semicircular external fixation device. In some embodiments, the distractor mechanism may be directly attached to the circular or semicircular external fixation device. In some embodiments, movable half pin holders may be utilized for attachment to circular or semicircular external fixation device.

In some embodiments, the transverse bone transport device may include modules for delivery of chemical/biological agents.

In some embodiments, the transverse bone transport device may include modules for mechanical stimulation of new vessels formation and increasing blood volume and flow.

Additional aspects, features, and advantages of the present disclosure will become apparent from the following detailed description.

BRIEF DESCRIPTION OF THE DRAWINGS

For a more complete understanding of the present disclosure and its advantages, reference is now made to the following description taken in conjunction with the accompanying drawings, in which like reference numbers indicate like features, and.

Although similar reference numbers may be used to refer to similar elements for convenience, it can be appreciated that each of the various example embodiments may be considered to be distinct variations.

DETAILED DESCRIPTION

Figure 1A:
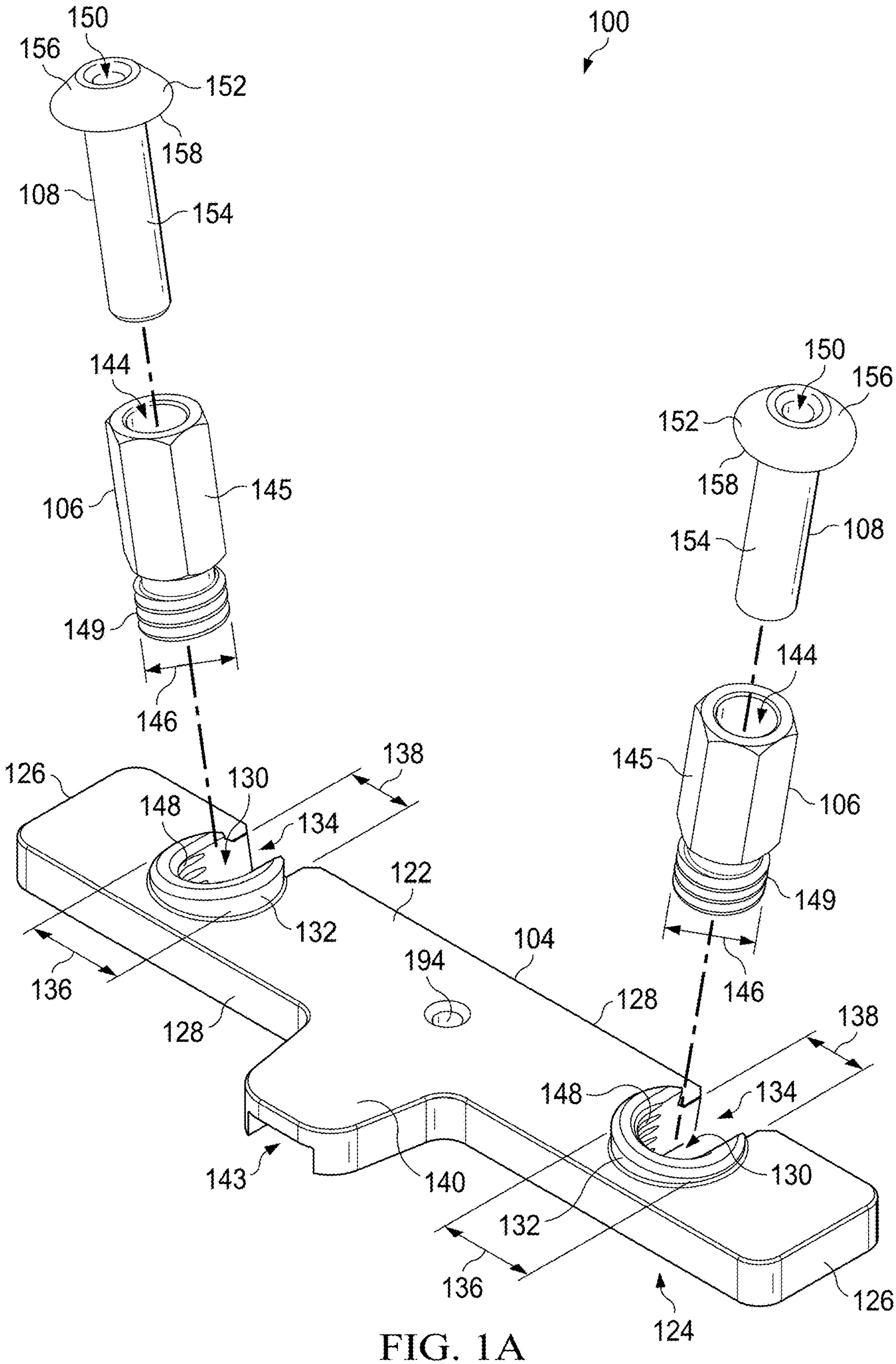
FIG. 1A is an exploded view of a template of a bone transport system, according to some embodiments of the present disclosure.

Exemplary embodiments will now be described hereinafter with reference to the accompanying figures, which form a part hereof, and which illustrate examples by which the exemplary embodiments, and equivalents thereof, may be practiced. As used in the disclosures and the appended claims, the terms “embodiment,” “example embodiment” and “exemplary embodiment” do not necessarily refer to a single embodiment, although it may, and various example embodiments, and equivalents thereof, may be readily combined and interchanged, without departing from the scope or spirit of present embodiments. Furthermore, the terminology as used herein is for the purpose of describing example embodiments only and is not intended to be limitations of the embodiments. In this respect, as used herein, unless specifically defined otherwise, the term “plate” may refer to any substantially flat structure or any other three-dimensional structure, and equivalents thereof, including those structures having one or more portions that are not substantially flat along one or more axis. Furthermore, as used herein, unless specifically defined otherwise, the terms “opening,” “recess,” “aperture,” and equivalents thereof, may include any hole, space, area, indentation, channel, slot, bore, and equivalents thereof, that is substantially round, oval, square, rectangular, hexagonal, and/or of any other shape, and/or combinations thereof, and may be defined by a partial, substantial or complete surrounding of a material surface. Furthermore, as used herein, the term “in” may include “in” and “on,” and the terms “a,” “an” and “the” may include singular and plural references. Furthermore, as used herein, the term “by” may also mean “from,” depending on the context. Furthermore, as used herein, the term “if” may also mean “when” or “upon,” depending on the context. Furthermore, as used herein, the words “and/or” may refer to and encompass any and all possible combinations of one or more of the associated listed items.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the “Background” is not to be construed as an admission that technology is prior art to any invention(s) in this disclosure. Furthermore, any reference in this disclosure to “invention” in the singular should not be used to argue that there is only a single point of novelty in this disclosure. Multiple inventions may be set forth according to the limitations of the multiple claims issuing from this disclosure, and such claims accordingly define the invention (s), and their equivalents, that are protected thereby. In all instances, the scope of such claims shall be considered on their own merits in light of this disclosure, but should not be constrained by the headings herein. The present disclosure hereby incorporates in its entirety the disclosure in U.S. Provisional Application No. 63/507,067, filed Jun. 8, 2023.

The present disclosure is, in some respects, directed to a bone transport system for use in orthopedic surgery. In one application, the bone transport system may be used to treat foot ulcers by performing transverse tibial bone transport to stimulate cell growth and neovascularization and increase blood flow for improved healing of the foot ulcers. The bone transport system may allow a physician to measure and cut a portion of the bone and move the portion of the bone transversely relative to the surrounding bone (i.e., base portion) to stimulate blood flow. The bone transport system may be used to form and connect to a portion of the bone and can move that portion of the bone during the treatment generally transverse from the axis of the bone. This portion of the bone may be referred to as the bone transport segment or the transport segment. The bone surrounding the transport segment may be referred to as the base portion of the bone. Moving the transport segment may stimulate cell growth and increase blood flow in the leg, thereby promoting healing of foot ulcers in the extremity.

The bone transport system includes a template 100 (see, e.g., FIGS. 1A-1D), a distractor 200 (see, e.g., FIGS. 2A-2D), one or more anchors, such as half-pins 400 (see, e.g., FIGS. 5J-5Q), one or more guide wires 190 (see, e.g., FIGS. 5D and 5G-5J), and a guide pin or wire 192 (see, e.g., FIG. 5A-5D).

Figure 1B:
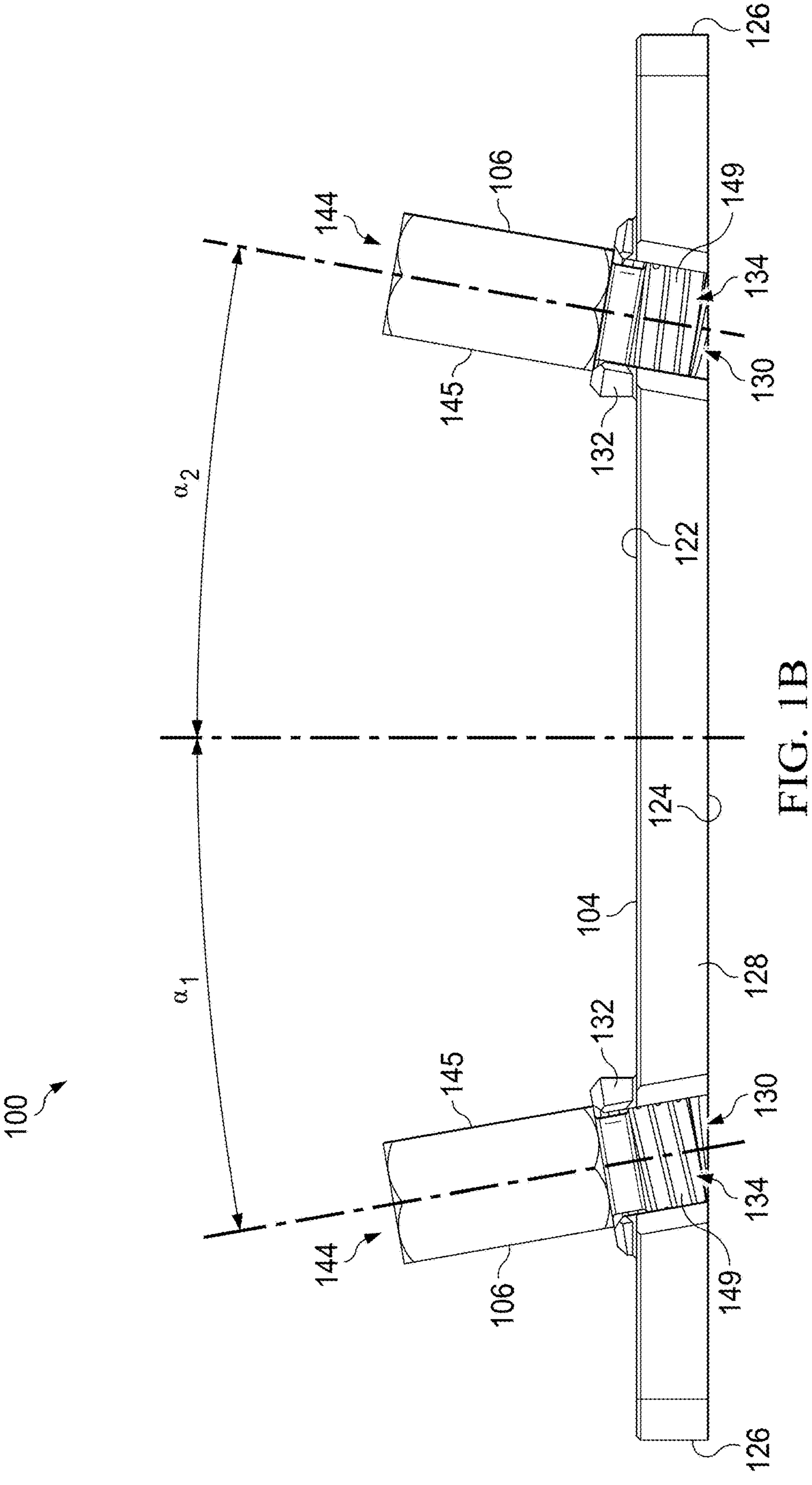
FIG. 1B is an assembled side view of the template shown in FIG. 1A.
Figure 1C:
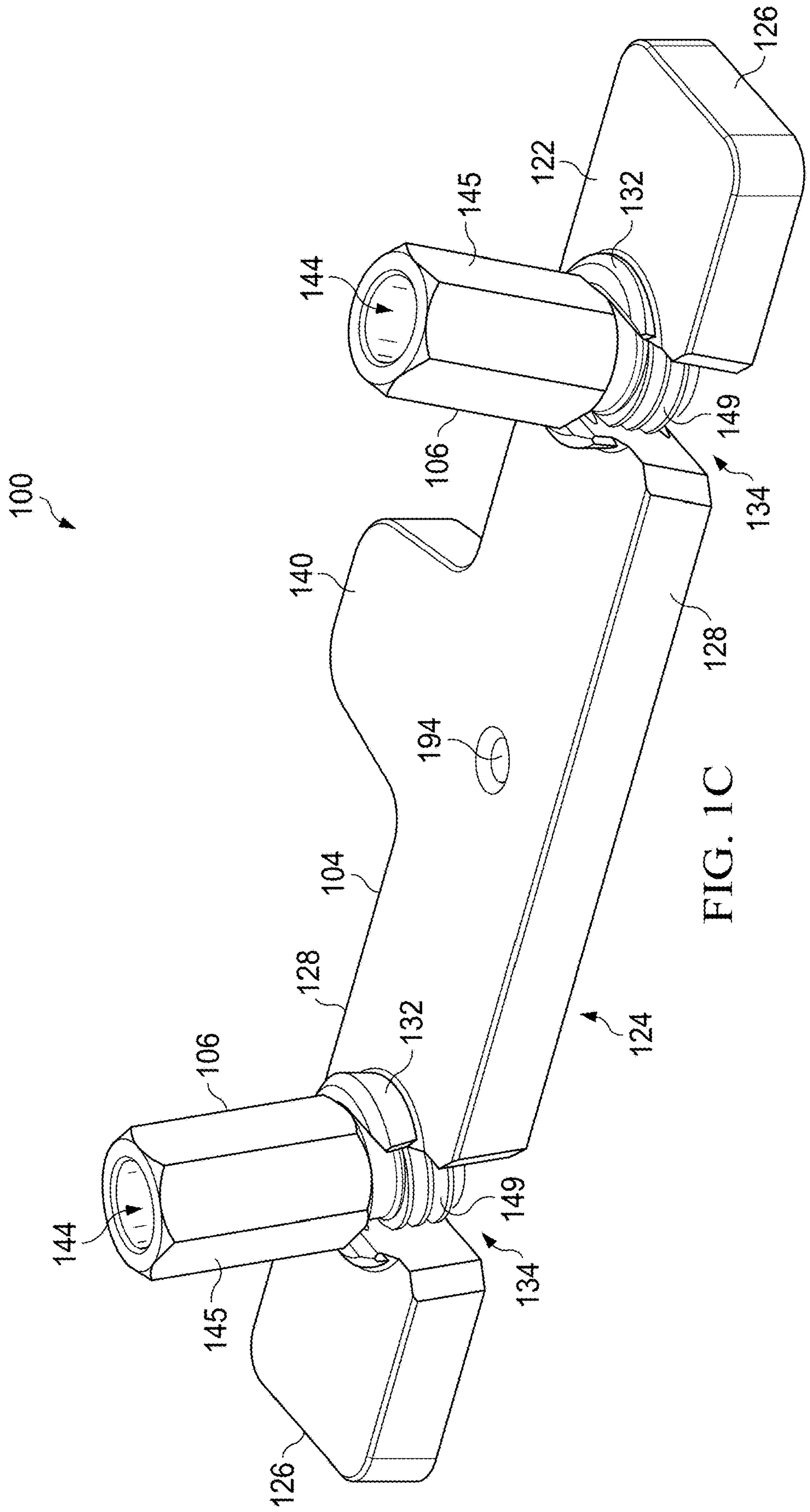
FIG. 1C is an assembled perspective top view of the template shown in FIG. 1A without wire sleeves.
Figure 1D:
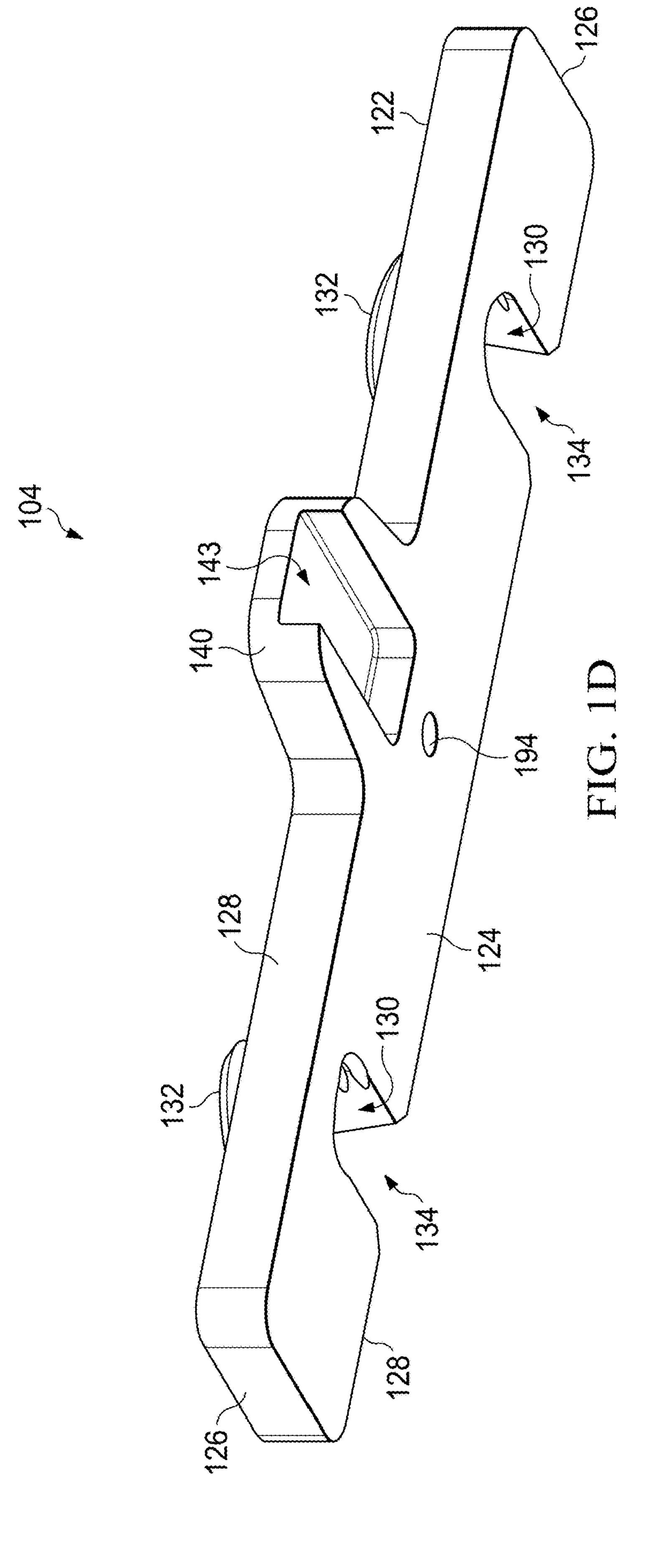
FIG. 1D is a perspective bottom view of the plate of the template shown in FIG. 1A.

FIGS. 1A-1D illustrate an example of a template 100, according to some embodiments of the present disclosure. FIG. 1A is an exploded perspective top view of the template. FIG. 1B is an assembled side view and FIG. 1C is an assembled perspective top view of the template 100 without wire sleeves 108. FIG. 1D is a perspective bottom view of the plate 104 of the template 100. The template 100 includes a plate 104, an anchor or half-pin sleeve guide 106, and a wire sleeve guide 108. In some embodiments, the template 100 may also include a stopper or a cap (not shown). The template 100 may be placed on the patient’s skin over a portion of the bone that the physician chooses as the transport segment 50 (see FIGS. 5B, 5P-5Q, and 6A-6B). The template 100 may then be used to measure, delineate, define or mark a skin flap over the transport segment 50. The skin flap may allow the physician to access the bone to form the transport segment 50. The template 100 may be placed directly on the chosen transport segment 50 and may be used to measure, delineate, or define the transport segment 50 of the bone so that it can be moved to stimulate blood flow to the extremity.

The template 100 includes a plate 104. The plate 104 functions to guide bone fixation devices or anchors such as half-pins 400, wires, anchors, screws, cables, or any other suitable bone fixation device. In addition, with the aid of such fixation devices, the plate 104 anchors the template 100 to the bone and maintains the position on the bone during the drilling operations. The plate 104 may have a top surface 122, a bottom surface 124, two ends 126, and two sides 128 disposed between the top surface 122 and the bottom surface 124 and between the two ends 126. The plate 104 may include two openings 130 that extend through the plate 104. The openings 130 may be generally circular. In other embodiments, the openings 130 may be any appropriate shape including, for example, oblong, rectangular, square, ovate, egg-shaped, elliptical, or ovoid. There may be one or more extensions 132 around the openings 130 to provide extra support to the sleeves 106, 108 or the guide wires 190 or half-pins 400 disposed therein (not shown, half-pins 400 (see, e.g., FIGS. 5J-5Q), one or more guide wires 190 (see, e.g., FIGS. 5G-5J)). The plate 104 may also include channels 134 that extend from the openings 130 to one side 128 of the plate 104. In some cases, a width 138 of the channel 134 may be smaller than a width or diameter 136 of the opening 130.

The half-pin sleeves 106 may be sized and shaped to fit within the openings 130 of the plate 104. The half-pin sleeves 106 may generally be cylindrical, but can have any shape. In other embodiments, the half-pin sleeves 106 may be any appropriate shape including, for example, a square, triangular, rectangular, polygonal, or irregular. The half-pin sleeves 106 may be hollow from the top to the bottom, thus forming an opening 144, and may be shaped to fit the half-pins 400 (see, e.g., FIGS. 5J-5Q) through the opening 144. The width or diameter 146 of the half-pin sleeve 106 may be sized so that it fits snuggly into the opening 130 of the plate 104 (i.e., the diameter 146 of the half-pin sleeves 106 may be slightly smaller than the diameter 136 of the openings 130 of the plate 104). The diameter 146 of the half-pin sleeves 106 may be larger than the width 138 of the channels 134 such that the half-pin sleeves 106 cannot move from the openings 130 through the channels 134.

In some embodiments, the openings 130 of the plate 104 may be threaded 148 and the bottom of the half-pin sleeve 106 may be threaded 149. Thus, the threading 149 on the half-pin sleeve 106 may be configured to mate with the threading 149 on the opening 130 of the plate 104 so that the half-pin sleeve 106 can be inserted therein. In the illustrated embodiment, the half-pin sleeve 106 includes male threading 149 and the opening 130 of the plate 104 includes female threading 148. However, in other embodiments, this may be reversed. Moreover, other embodiments, may use any suitable coupling mechanism that allows the half-pin sleeve 106 to be removed along the axis of the opening 130 of the plate 104. For example, the half-pin sleeves 106 may be snapped into the openings 130 of the plate 104, the half-pin sleeves 106 may form a friction-fit with the openings 130 of the plate 104, the half-pin sleeves 106 may use quarter-turn technology to twist into coupling with the openings 130.

In some embodiments, the exterior surface of the half-pin sleeves 106 above the threading 149 may include a plurality of flat surfaces 145. The flat surfaces 145 may make it easier for a physician to grab and maneuver the half-pin sleeves 106. However, any suitable gripping mechanism may be used on the half-pin sleeves 106. For example, the half-pin sleeves 106 may include ridges, a tab or handle, or a softer or more flexible material to improve gripping of the half-pin sleeves 106.

The wire sleeves 108 may be sized and shaped to fit within the openings 144 of the half-pin sleeves 106. The wire sleeves 108 may be generally cylindrical. In other embodiments, the wire sleeves 108 may be any appropriate shape including, for example, a square, triangular, rectangular, polygonal, or irregular. Each wire sleeve 108 may be hollow from the top to the bottom, thus forming an opening 150. The openings 150 in the wire sleeves 108 may be shaped to fit a guide wire 190 (see, e.g., FIGS. 5G-5J) through the opening 150. The opening 150 can have any shape that generally matches a cross-section of the guide wires 190, e.g., circular, cylindrical, square, rectangular, polygonal, or irregular.

Each wire sleeve 108 includes a head 152 that extends upward and outward from a shaft 154 of the wire sleeve 108. In some embodiments, the top 156 of the head 152 is rounded or curved from the largest diameter 158 to the opening 150. Thus, the head 152 forms a semi-spherical-like shape. The head 152 of the wire sleeve 108 is generally smooth so that the wire sleeve 108 does not irritate skin that contacts the head 152.

The plate 102, 104 may include a guide pin aperture 194 that is shaped to fit a guide pin or wire 192 (see e.g., FIGS. 5A-5D). The guide pin 192 may be configured to attach the template 100 to the bone before insertion of the guide wires 190 (see e.g., FIGS. 5B-5C), as described in more detail below.

As shown in FIG. 1B, in some cases, the openings 130 and extensions 132 of the plate 104 may be angled outward towards the ends 126 of the plate 104. The opening 130 on the left of FIG. 1B (and corresponding half-pin sleeve 106) is oriented at an angle of $\alpha$1 relative to the vertical. The opening 130' on the right of FIG. 1B (and corresponding half-pin sleeve 106') is oriented at an angle of $\alpha$2 relative to the vertical. This will ultimately lead to the half-pins 400 (not shown) being guided during insertion to an angle of $\alpha$1 for pin 400 and $\alpha$2 for pin 400', resulting in the tips of the half-pins 400, 400' converging within the transport segment 50.

Angle $\alpha$1 and $\alpha$2 may be any appropriate value. For example, $\alpha$1 and $\alpha$2 may be any angle within a range of 0 degrees to 80 degrees. In some embodiments, $\alpha$1 or $\alpha$2 may be plus or minus 0, 5, 10, 15, 20, 25 30, 35, 40, 45, 50, 60, 70 or 80 degrees. In some embodiments, the openings 130, 130' may be at a 15-degree angle relative to the vertical. In some cases, the openings 130, 130' may be at different angles relative to the surface of the bone. Although the openings 130, 130' are shown as being angled inward towards each other, the openings 130, 130' may also be angled outward away from each other or may be angled in the same direction.

Thus, when the half-pin sleeves 106 and the wire sleeves 108 are inserted into the openings 130, the sleeves 106, 108 are also angled outward towards the ends 126 of the plate 104 such that the sleeves 106, 108 are angled with respect to the top surface 122 of the lower plate 204. This allows the half-pins 400 (see e.g., FIGS. 5K-6A) to be inserted into the transport segment 50 such that they are angled outwards towards the ends 126 of the plate 104 and inwards towards each other such that they converge within the transport segment 50. By angling the half-pins 400 inwards towards each other, this provides more stability and improves movement of the transport segment 50 (see e.g., FIGS. 5K-6A), as described in more detail below.

In some embodiments, the template 100 (or the wire 190) may include caps, beads, or stoppers (not shown). When a guide wire 190 is inserted through the wire sleeve 107, 108, a stopper may be included on the wire in a fixed manner or placed over the guide wire 190 such that the bottom of the stopper contacts the top of the wire sleeve 107, 108. The stopper thus serves as a depth stop to limit penetration of the wire into the bone. The guide wire 190 may then be cut above the stopper. Thus, the stopper may be used as a guide for cutting the guide wire 190. The stopper may be rounded such that when a skin flap is pulled over the stopper, the guide wire 190 will not contact, cut, or injure the skin flap. In some embodiments, the stopper may have a pointed or rounded cone upper portion or may be a rounded or softened shape such as spherical, toroidal, ellipsoid, conical or oblate. Thus, in some cases, the stopper may be configured to provide a smooth contact with the skin above the wire sleeve 107, 108.

In some embodiments, the plate 104 may include a tab 140 at the posterior side 128 for easy handling of the template 100 during positioning on the skin and later positioning on the surface of the bone. The tab 140 may include grooves, rubber, or other features to improve the physician's ability to grip the plate 104. As shown in FIGS. 1A and 1D, the tab 140 may include a recess 143 on the bottom. This recess 143 may allow the physician to more easily grab the tab 140 and, thus, more easily maneuver the template 100 using her hand or an instrument (e.g., forceps) (not shown).

In some embodiments, the plate 104 may not have two openings 130. The plate 104 may have any suitable number of openings 130 including, for example, 1, 3, 4, or 5 openings 130. In some embodiments, the template 100 may have elongated guide apertures that form cutting guide slots or plurality of holes to guide cutting of the bone. For example, cutting guide slots may guide bladed cutting instruments and a plurality of holes may guide a drill bit. The plate 104 may be formed of any suitable material including metal or plastics or a combination thereof.

Figure 1E:
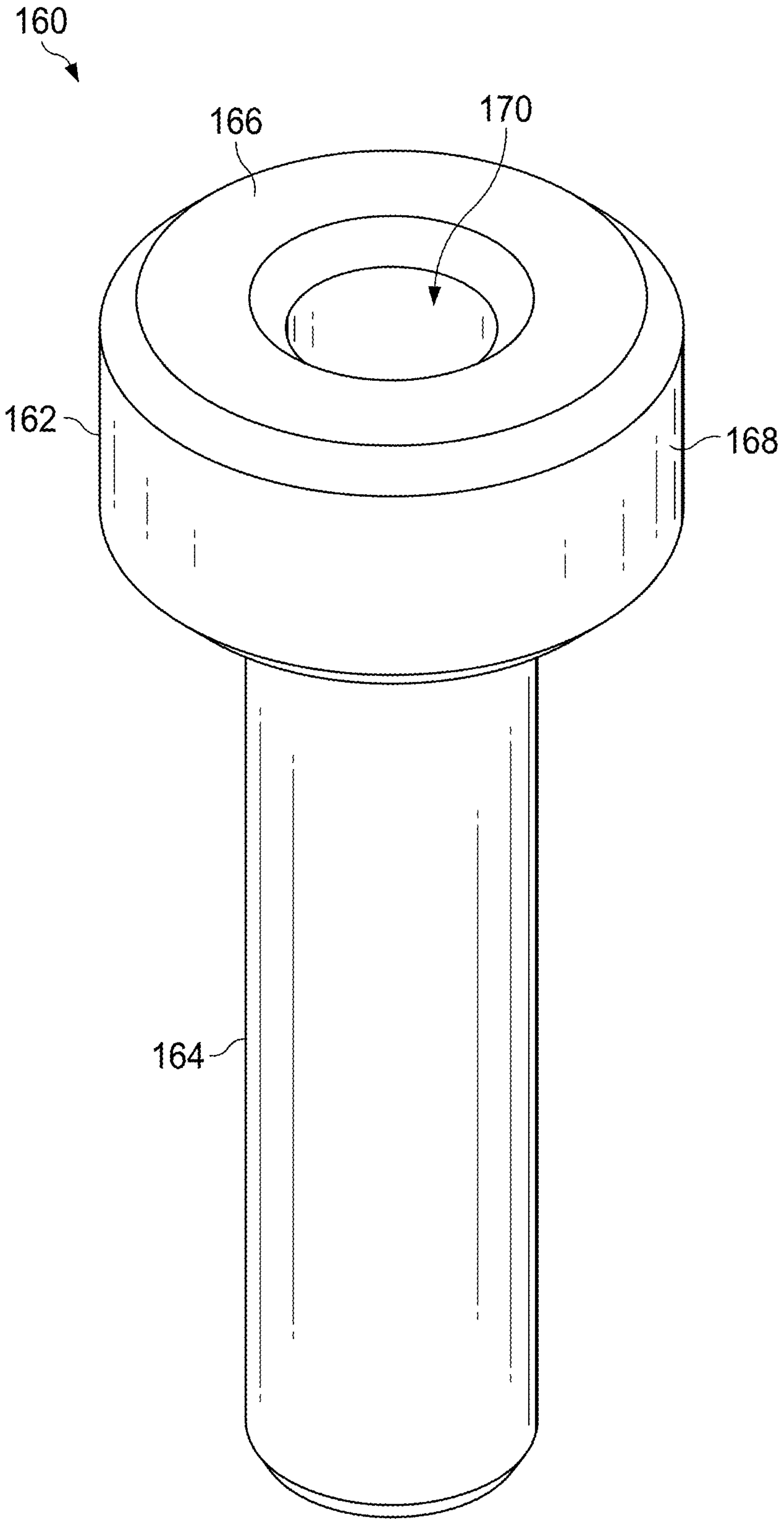
FIG. 1E is a perspective view of a drill sleeve of a template, according to some embodiments of the present disclosure.

In some embodiments, the template 100 may further include a drill guide or sleeve 160. FIG. 1E illustrates a drill sleeve 160, according to one or more embodiments of the present disclosure. Like the wire guides 108, the drill sleeves 160 may be sized and shaped to fit within the openings 144 of the half-pin sleeves 106. The drill sleeves 160 may be generally cylindrical. In other embodiments, the drill sleeves 160 may be any appropriate shape including, for example, a square, triangular, rectangular, polygonal, or irregular. The drill sleeve 160 may be hollow from the top to the bottom, thus forming an opening 170. The openings 170 in the drill sleeve 160 may be shaped to fit a drill bit therethrough, as described in more detail below.

The drill sleeve 160 may include a head 162 that extends upward and outward from a shaft 164. In some embodiments, the top 166 of the head 162 is generally flat with an outer side surface 168 extending downward therefrom. Thus, the head 162 of drill sleeve 160 may form a cylindrical-like shape.

Figure 2A:
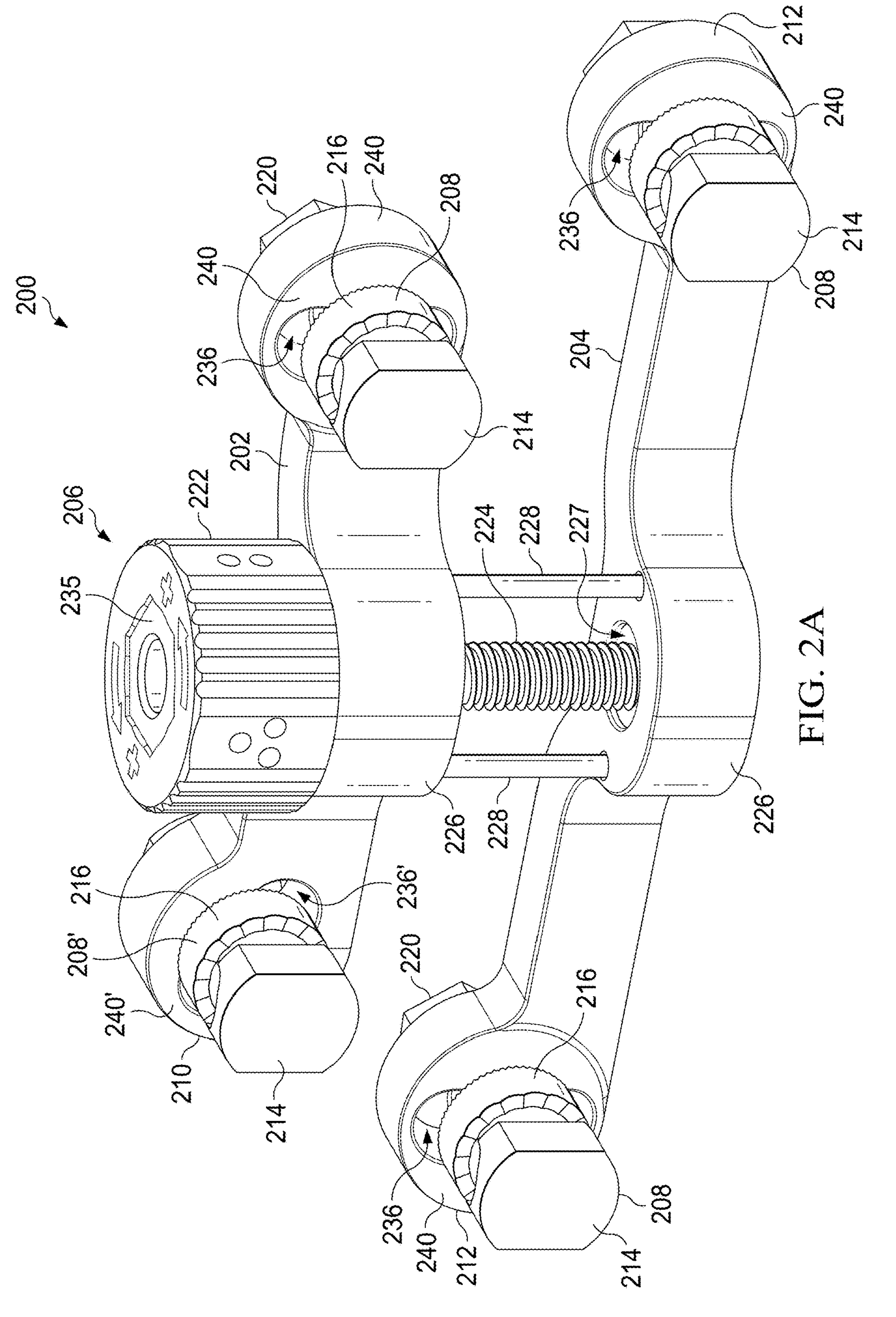
FIG. 2A is a perspective front view of a distractor of a bone transport system, according to some embodiments of the present disclosure.
Figure 2B:
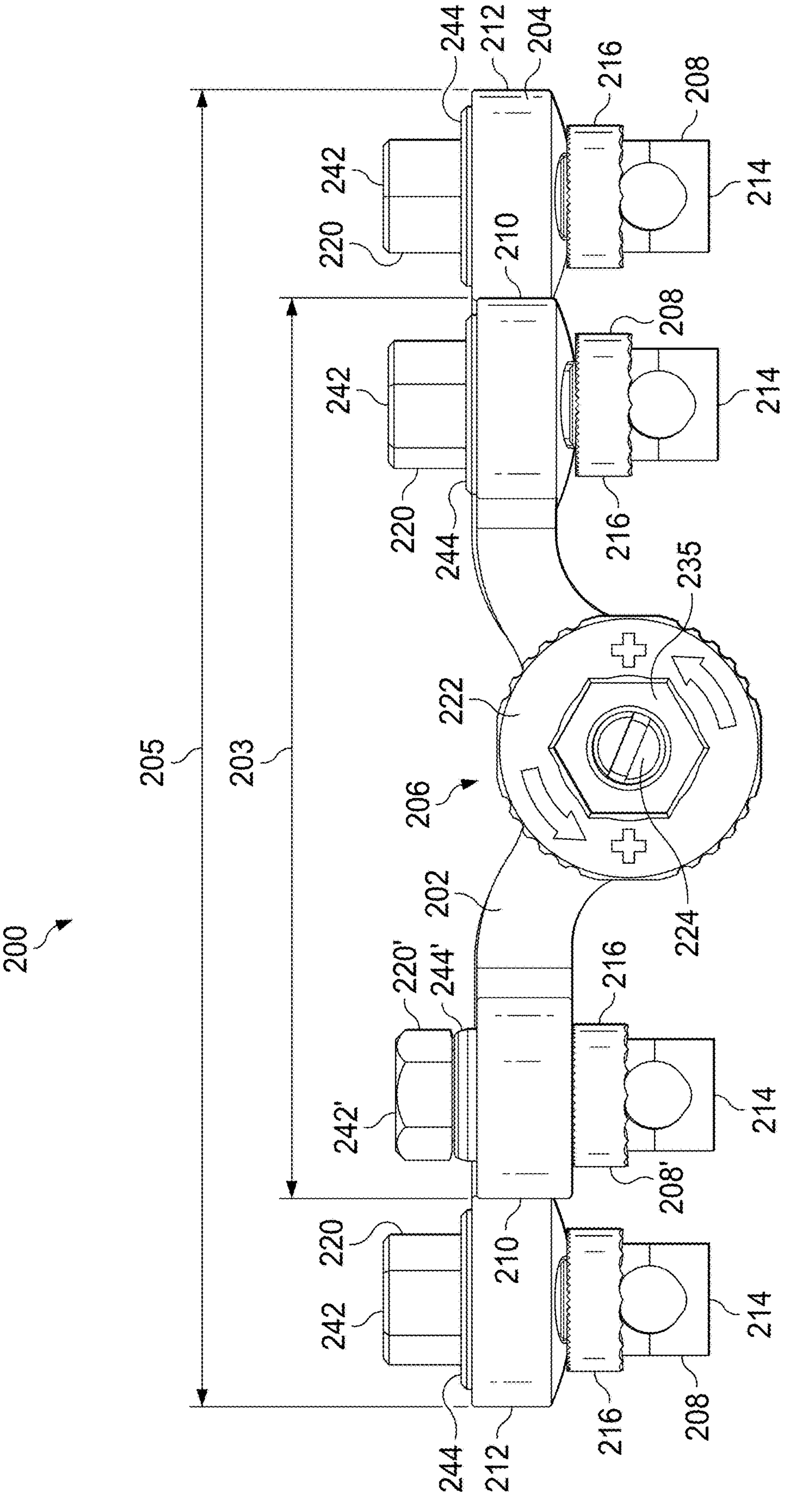
FIG. 2B is a top view of the distractor shown in FIG. 2A.
Figure 2C:
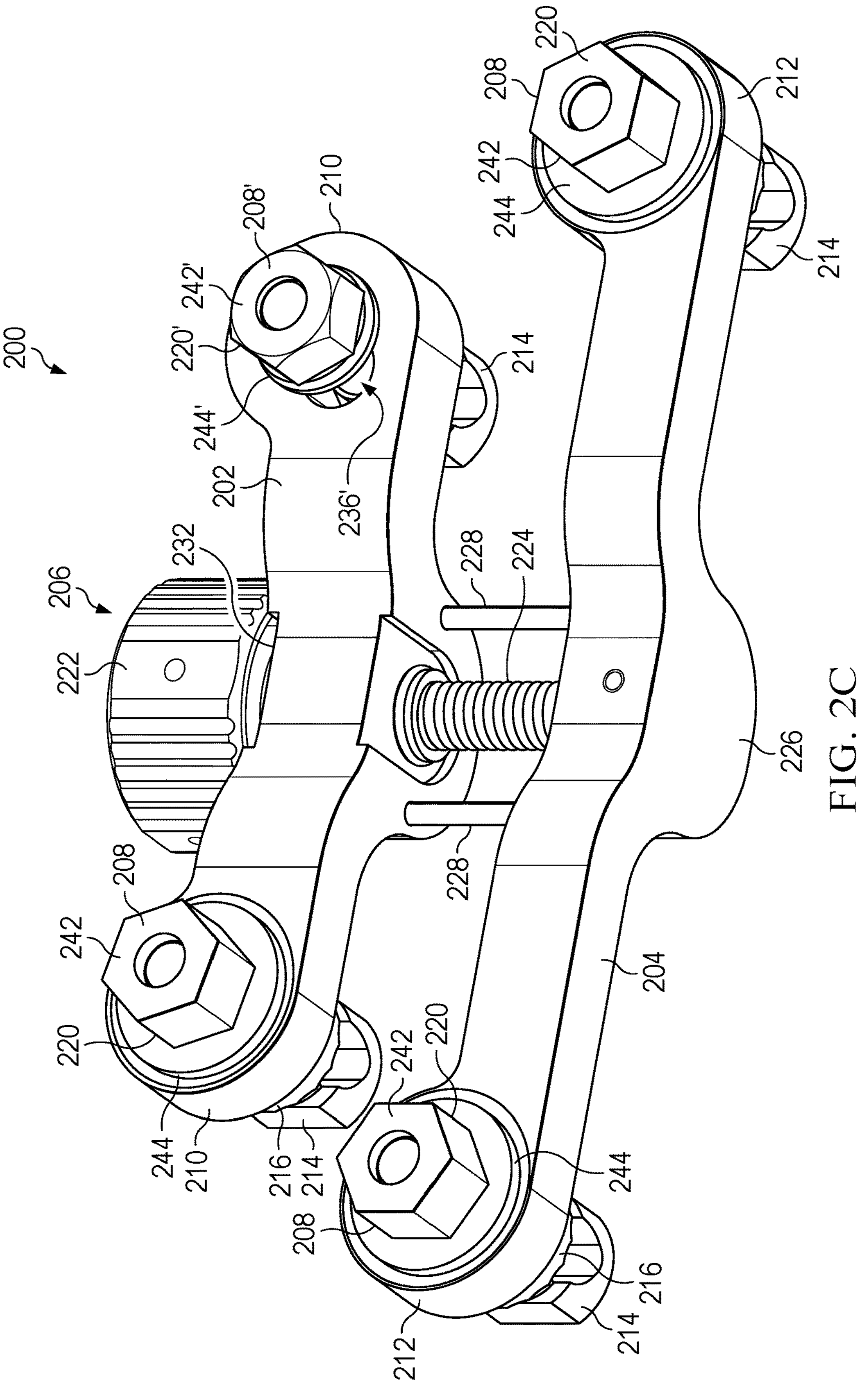
FIG. 2C is a perspective back view of the distractor shown in FIG. 2A.
Figure 2D:
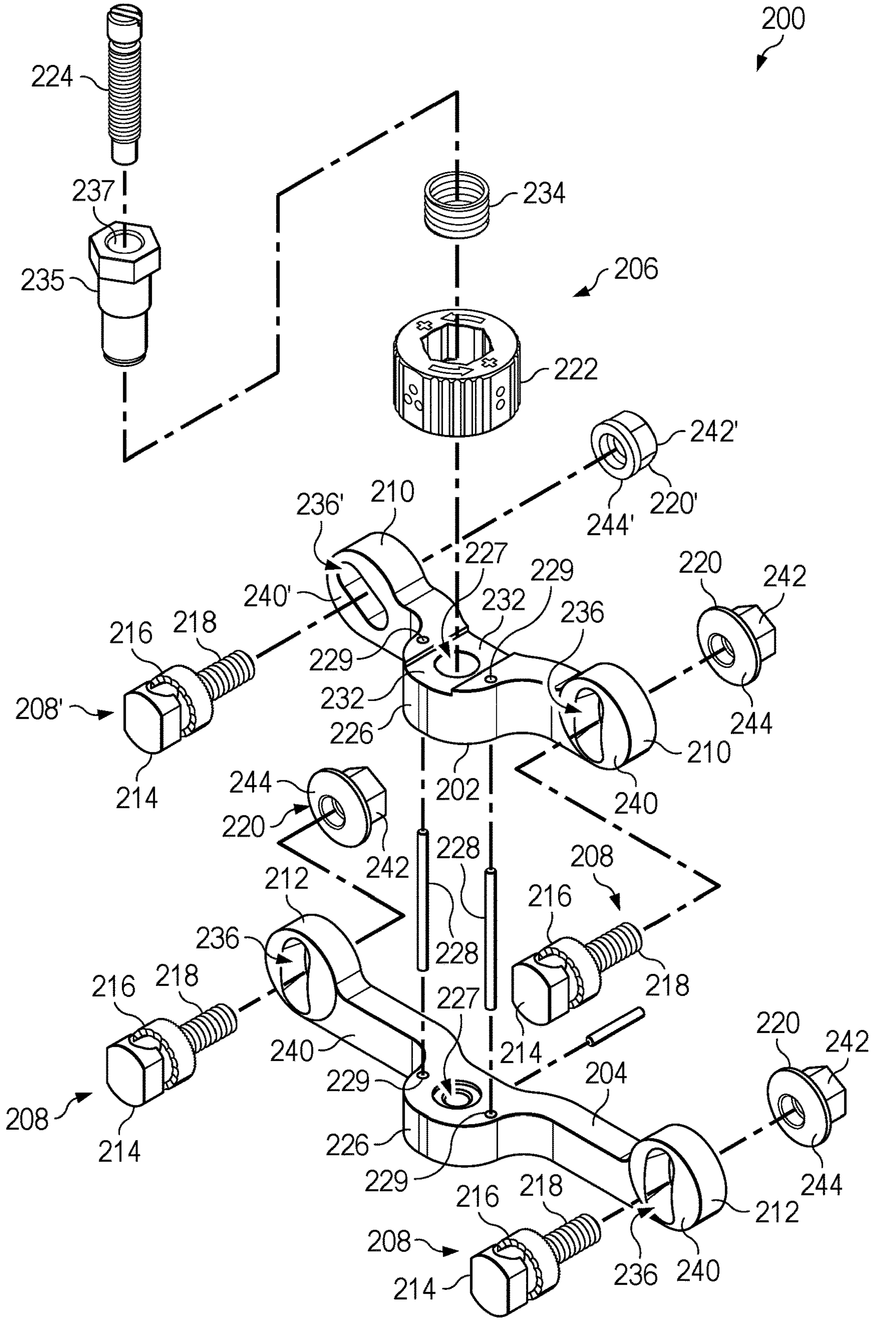
FIG. 2D is an exploded of the distractor shown in FIG. 2A.

FIGS. 2A-2D illustrate an example of a distractor 200, according to some embodiments of the present disclosure. FIG. 2A is a perspective front view, FIG. 2B is a top view, FIG. 2C is a perspective back view, and FIG. 2D is an exploded of the distractor 200.

Once the half-pins 400 (see e.g., FIGS. 5J-5Q) have been inserted into the transport segment 50 (see e.g., FIGS. 5B and 5P-5Q) and the holes have been drilled around at least part of the transport segment 50, the distractor 200 may be attached to the half-pins 400 and additional half-pins 400' (see e.g., FIGS. 50-5Q) may be inserted into the base portion 52 of the bone next to the transport segment 50 and may be attached to the distractor 200, as described in more detail below. The distractor 200 may move the transport segment 50 transverse or laterally with respect to an axial direction of the bone to stimulate blood flow to the extremity.

The distractor 200 may include an upper beam 202, a lower beam 204, and an actuator 206. The upper beam 202 and the lower beam 204 may have half-pin holders 208 disposed on each end 210, 212 (respectively) of the beams 202, 204. A length 203 of the upper beam 202 may be shorter than a length 205 of the lower beam 204. Thus, the half-pin holders 208 of the upper beam 202 may be longitudinally displaced relative to the half-pin holders 208 of the lower beam 204. Thus, the half-pin holders 208 of the upper beam 202 are located closer to a center of the distractor 200 and the half-pin holders 208 of the lower beam 202 are located further from the center of the distractor 200.

The upper and lower beams 202, 204 may have openings 236 proximate the ends 210, 212. Each opening 236 may have a rounded or partially-spherical shaped inner surface (not shown) and a rounded or partially spherical outer surface 240. In some embodiments, the outer surface 240 may match the profile of the inner surface, while in other embodiments the outer surface 240 may be cylindrical and the inner surface may be spherical to engage a spherically nut 220.

The openings 236 may be vertically elongated or slotted. Three of the openings 236 may be oriented generally vertically (though they may be angled slightly relative to the vertical). Each of these three openings may have the same angulation. However, a fourth opening 236' located on the upper beam 202 may be angled relative to the vertical and relative to the other openings 236. For example, the fourth opening 236' may be angled outward from the center at an angle in a range of 0 degrees to 90 degrees. This may allow the distractor 200 more flexibility when attaching the half-pins 400 to the half-pin holders 208.

Three half-pin holders 208 may be disposed in the three openings 236. The half-pin holders 208 may comprise a clamp having an outer portion 214 moveably coupled to an inner portion 216. The half-pin holders 208 may include a threaded extension 218 extending through the openings 236 in the beams 202, 204. A nut 220 may be threadedly coupled to the threaded extension 218. The nut 220 may include a head 242 and a base 244. The head 242 may be hexagonally-shaped. In other embodiments, the head 242 may be another shape including, for example, square, pentagon, circular, or any other shape. The base 244 may be rounded, such as, for example, partially or semi-spherical. The rounded base 244 may be shaped so that the nut 220 may pivot, rotate, or otherwise move along the inner surface 238 of the opening 236. The inner portion 216 of the clamp may have a flat or rounded lower surface that may be shaped to pivot, slide, rotate, or otherwise move along the rounded outer surface 240 of the opening 236. In some embodiments, the lower surface of the inner portion 216 may have grooves or be otherwise roughened to increase the friction between the inner portion 216 and the outer surface 240 of the opening 236.

In some embodiments, three of the half-pin holders 208 include a nut 220 with a rounded base 244. However, a fourth half-pin holder 208' may include a nut 220' with a similar hexagonal head 242' and a relatively cylindrical base 244'. The cylindrical base 244' may be smaller than the rounded base 244 of the other three half-pin holders 208. The fourth half-pin holder 208' may include the same clamp (with the same outer portion 214 and inner portion 216) and the same threaded extension 218. This fourth half-pin holder 208' may be configured to be inserted into the fourth opening 236' so that the fourth half-pin holder 208' has a larger range of motion than the other three half-pin holders 208.

In some embodiments, the fourth opening 236' may allow the fourth half-pin holder 208' to move laterally or at an angle relative to the beam 202 while allowing the half-pin holder 208' to pivot or rotate. Thus, the half-pin 400 disposed within the fourth half-pin holder 208' may have additional axes of movement. Advantageously, with diverging half pin axes, the fourth opening 236' in conjunction with the fourth half-pin holder 208' may allow the physician to adjust the distance of the distractor 200 from the bone while continuing to accommodate the same pin angles. For example, if a patient has thicker skin or a large amount of fat, muscle, or other soft tissue between the skin and the bone, the fourth half-pin holder 208' may slide outward along the fourth opening 236' so that the distractor 200 can be moved further away from the bone. The distance between the distractor 200 and the bone may be adjusted so that the distractor 200 contacts the skin or so that there is a gap between the distractor 200 and the skin. Thus, the distractor 200 may be used for a wide variety of patients who may have various amounts of soft tissue around their tibia.

For all half-pin holders 208, 208', when the nut 220 is loosened, the outer portion 214 of the clamp may be configured to move outward from the beam 202, 204 and may allow the half-pin holder 208, 208' to pivot, swivel, or otherwise rotate. The half-pin holder 208, 208' may also be able to slide or move up or down the opening 236, 236'. The outer portion 214 may have one or more grooves or channels for fitting a half-pin 400. Thus, the half-pin holders 208, 208' may be able to move to accommodate any angular position of the half-pin 400, including along an axis parallel to the beam 202, 204 (i.e., a horizontal axis) or an axis perpendicular to the beam 202, 204 (i.e., a vertical axis).

When the nut 220, 220' is moved to tighten the clamp, the outer portion 214 contacts and is pulled against the inner portion 216 to hold or secure the half-pin 400 to the beam 202, 204. When tightened, the clamp may fix the angular position of the half-pin 400, thus preventing the outer portion 214 or the half-pin 400 from moving relative to the beam 202, 204 or rotating. In some embodiments, the half-pin holders 208, 208' may rotate through multiple discrete angular positions or may rotate continuously through all angular positions. The inner surface of the outer portion 214 and the outer surface of the inner portion 216 may have grooves that may interconnect so that the half-pin holders 208, 208' can accommodate discrete angular positions and/or to prevent movement of the portions 214, 216 when the clamp is tightened. As explained above, the fourth half-pin holder 208' may have a larger range of motion than the other three half-pin holders 208 and, thus, may be capable of rotating through a larger range of angles than the other three half-pin holders 208.

Although particular embodiments of a half-pin holder 208, 208' are described herein, any appropriate moveable holder 208, 208' that is configured to accommodate multiple angular positions of a half-pin 400 may be used herein. For example, one or more half-pin holders 208, 208' may be ball and socket connections, a hinged clamp, or use a screw or bolt as described in more detail below.

The half-pin holders 208, 208' of the upper beam 202 may be arranged such that they can connect to the half-pins 400 that were inserted into the transport segment 50 of the bone using the template 100, as described in more detail below. The half-pin holders 208 of the lower beam 204 may be configured to attach to half-pins 400' that are inserted into the base portion 52 of the bone next to the transport segment 50.

The actuator 206 may include a knob 222 and a threaded rod 224. The beams 202, 204 may each include a block 226 having an opening 227 to fit the threaded rod 224. Each block 226 may be coupled to the center of the beams 202, 204. The knob 222 may be coupled to one end of the threaded rod 224. The knob 222 may be disposed on the top of block 226 coupled to the upper beam 202 such that the threaded rod 224 extends through the openings 227 in both blocks 226. There may be support posts 228 that extend from an opening 229 in one block 226 to an opening 229 in the other block 226. The support posts 228 may be disposed on either side of the threaded rod 224 and may be located close or proximate to the threaded rod 224 to provide support and prevent the upper beam 202 from rotating relative to the lower beam 204.

In some embodiments, the threaded rod 224 may be fixedly secured to at least one of the openings 227 in the block 226. The threaded rod 224 may be threadedly coupled to the knob 222. The knob 222 may be rotated to move the threaded rod 224 upwards and downwards within an opening in the knob 222. The knob 222 may be rotated in a first direction to move the threaded rod 224 downwards and may be rotated in a second, opposite direction to move the threaded rod 224 upwards. Thus, as the knob 222 is rotated in the first direction, the upper beam 202 and the lower beam 204 may be moved closer to each other. As the knob 222 is rotated in the second direction, the upper beam 202 and lower beam 204 may be moved further apart from each other. The support posts 228 may be moveably coupled to at least one block 226 (ex. to the lower beam 204) to allow the beams 202, 204 to move relative to each other.

In other embodiments, the openings 227 in the block 226 on the lower beam 204 and/or the block 226 on the upper beam 202 may be threaded such that they threadedly engage the threaded rod 224. The knob 222 may be rotated to move the threaded rod 224 through the openings 227 of the blocks 226. The knob 222 may be rotated in a first direction to move the threaded rod 224 downwards and may be rotated in a second, opposite direction to move the threaded rod 224 upwards. Thus, as the knob 222 is rotated in the first direction, the upper beam 202 and the lower beam 204 may be moved closer to each other. As the knob 222 is rotated in the second direction, the upper beam 202 and lower beam 204 may be moved further apart from each other. The support posts 228 may be moveably coupled to one block 226 to allow the beams 202, 204 to move relative to each other. In other embodiments, there is no block 226 coupled to the upper beam 202 or lower beam 204.

The knob 222 may be capable of rotating through a plurality of discrete rotational positions. For example, the knob 222 may be configured to move in quarter-turns by the provision of projections 230 (shown in FIGS. 5N, 5Q, 9A, and 9B) on the underside of the knob 222, which fit within recesses 232 (shown in FIGS. 2C, 2D, 5N, 5Q, 9A, and 9B) on the block 226 at 90-degree intervals. The knob 222 may include a sleeve adapter 235 with an opening 237 extending from the top to the bottom of the sleeve adapter 235. The opening 237 may be configured to fit the threaded rod 224. A spring 234 may be disposed between the knob 222 and the sleeve adapter 235 to bias the projections 230 towards the recesses 232. In this way, each time the knob 222 is turned, the threaded rod 224 is moved a predetermined amount. For example, each quarter-turn of the knob 222 may move the threaded rod 224 upwards or downwards by 0.25 millimeters (mm). In other examples, each turn or partial turn of the knob may move the threaded rod 0.1, 0.2, 0.3, 0.4, 0.5, 0.6, 0.7, 0.8, 0.9, or 1 mm. The amount that the threaded rod 224 is moved may correspond to the amount that the transport segment 50 is moved.

In other embodiments, the knob 222 may be able to move continuously through any rotational position. In some cases, the distractor 200 may be able to move the transport segment 50 in incremental or discrete amounts up from 0 mm distraction to 20 mm distraction and back to 0 mm distraction.

Figure 3A:
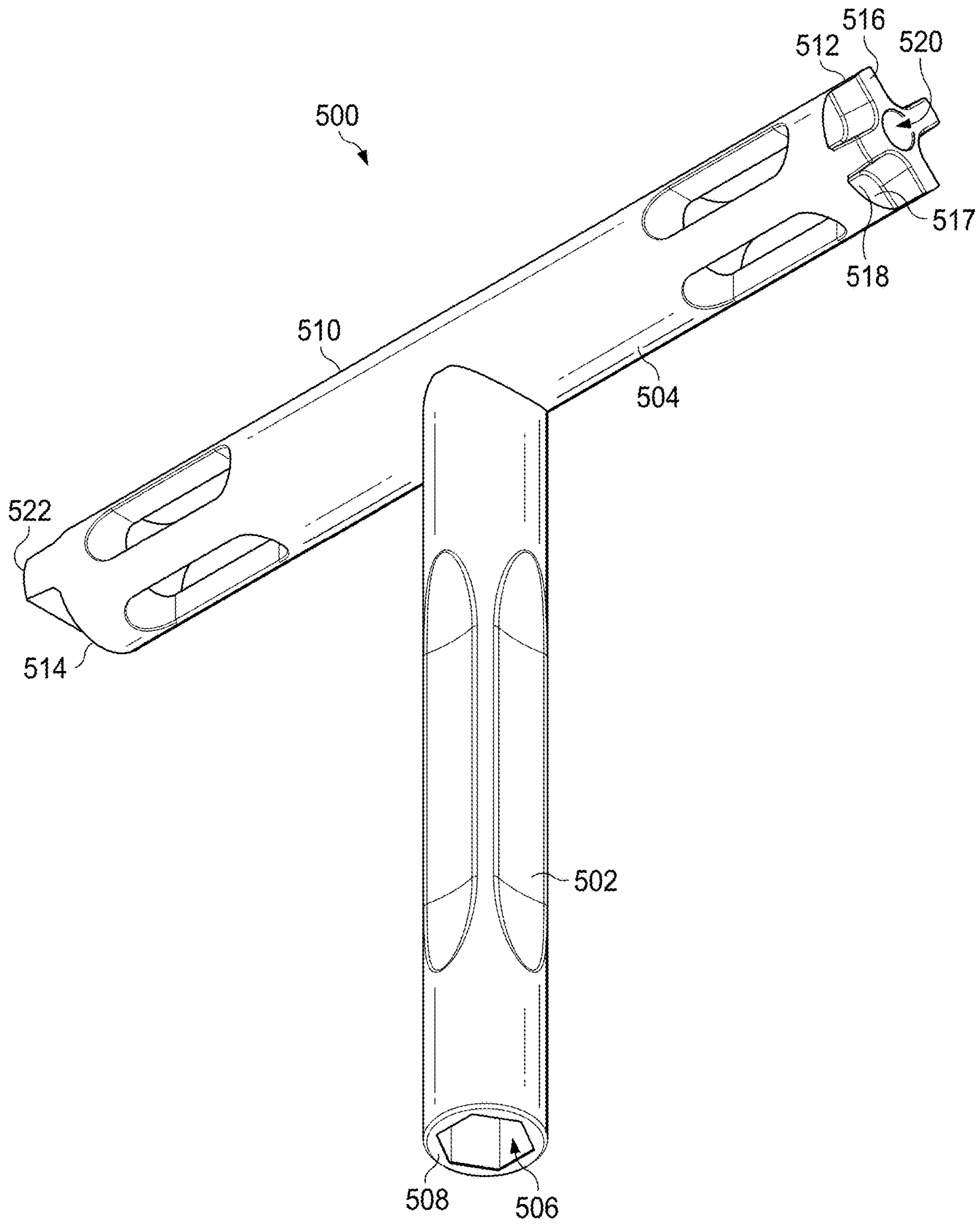
FIG. 3A is a perspective front view of a T-shaped drill guide, according to some embodiments of the present disclosure.
Figure 3B:
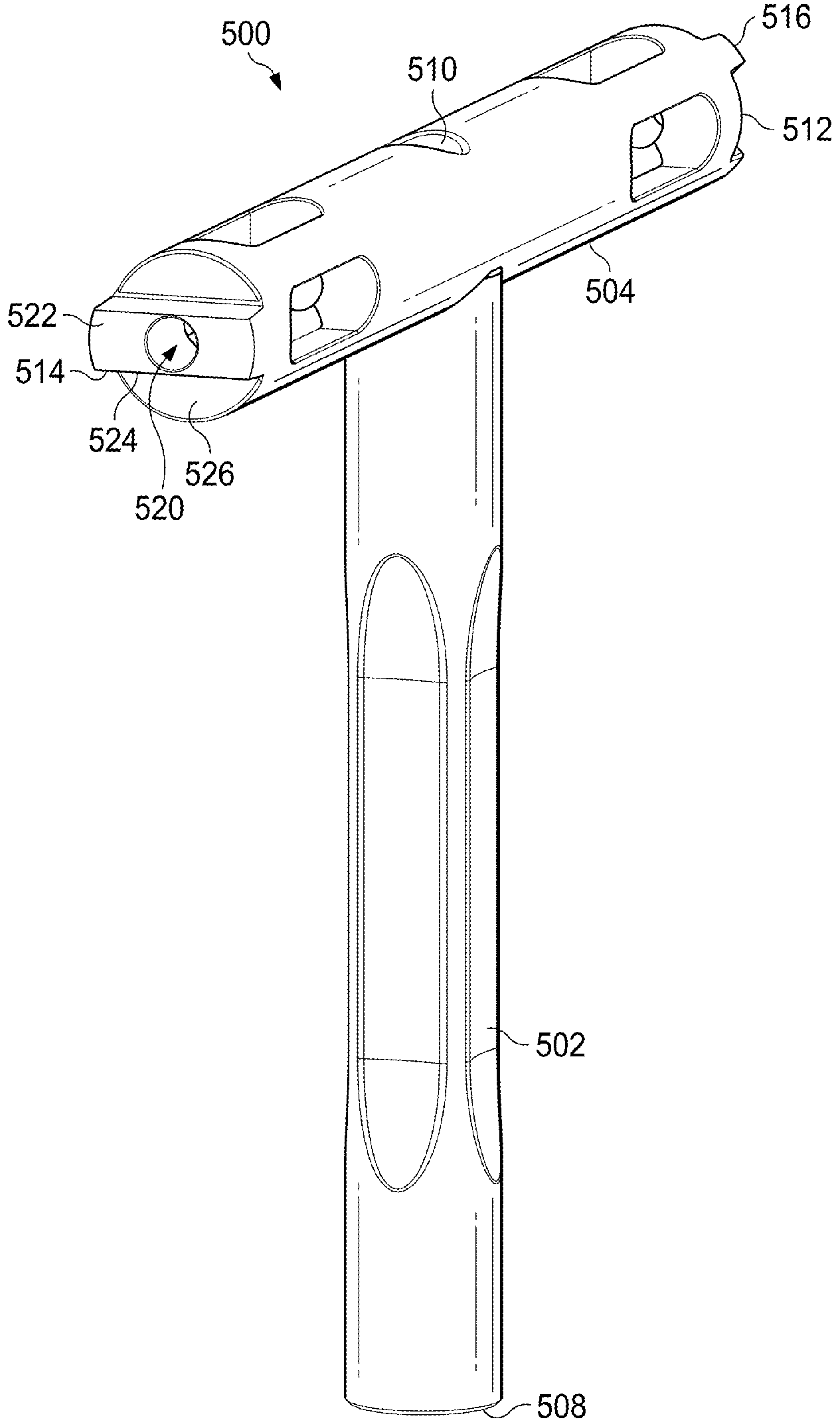
FIG. 3B is a perspective side view of the T-shaped drill guide shown in FIG. 3A.
Figure 3C:
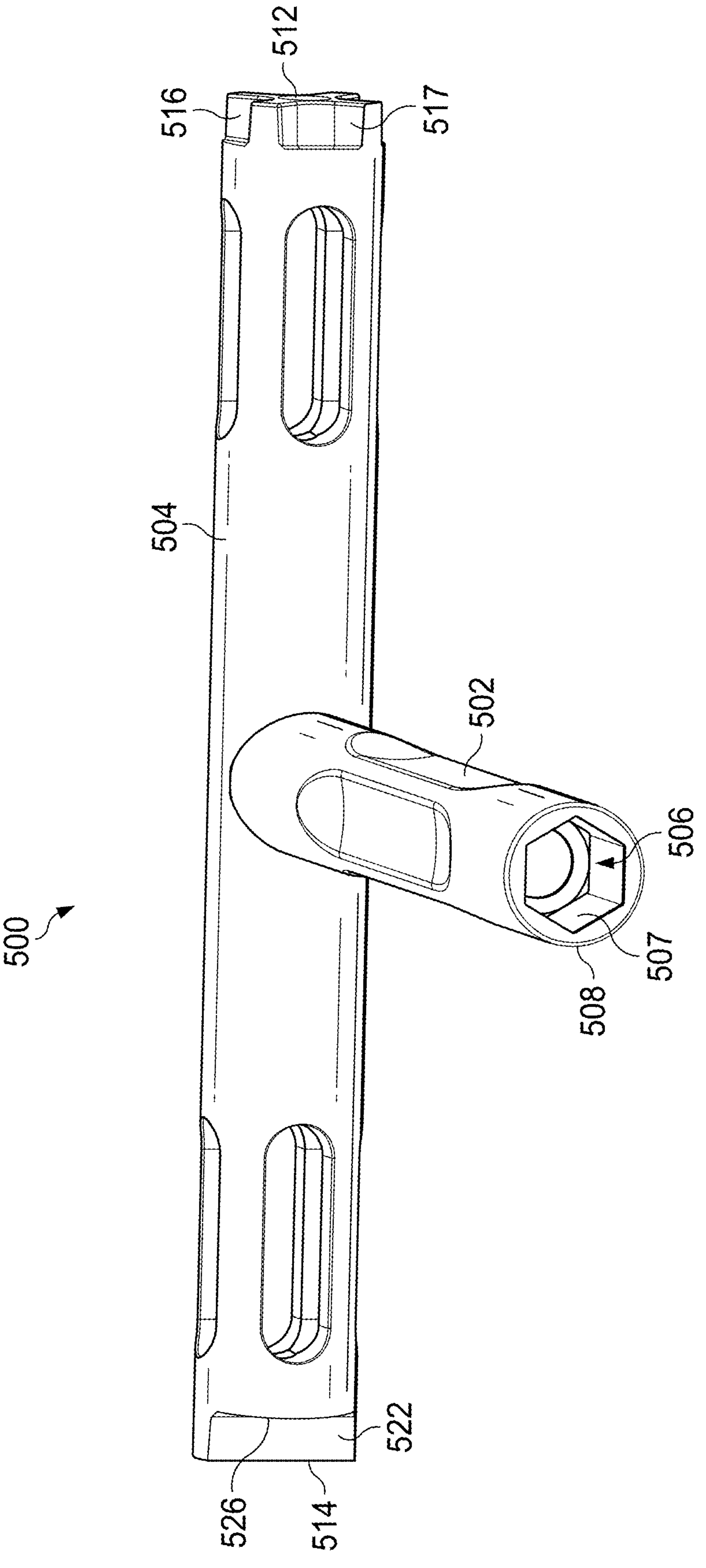
FIG. 3C is a perspective bottom view the T-shaped drill guide shown in FIG. 3A.
Figure 3D:
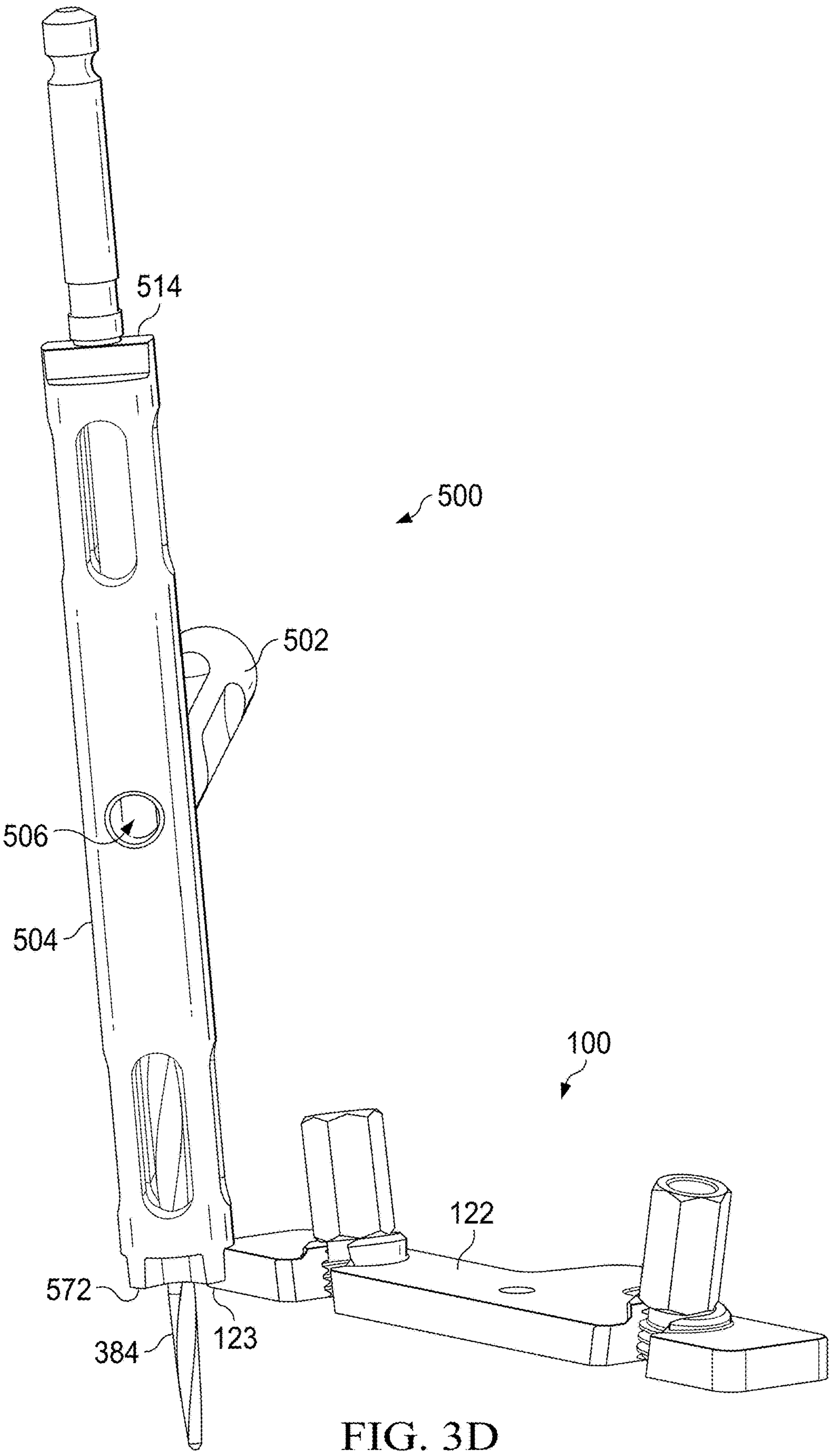
FIG. 3D is a perspective side view the T-shaped drill guide shown in FIG. 3A with drill bit inserted and being used to drill holes around the corners of a plate of a template, according to some embodiments of the present disclosure.
Figure 3E:
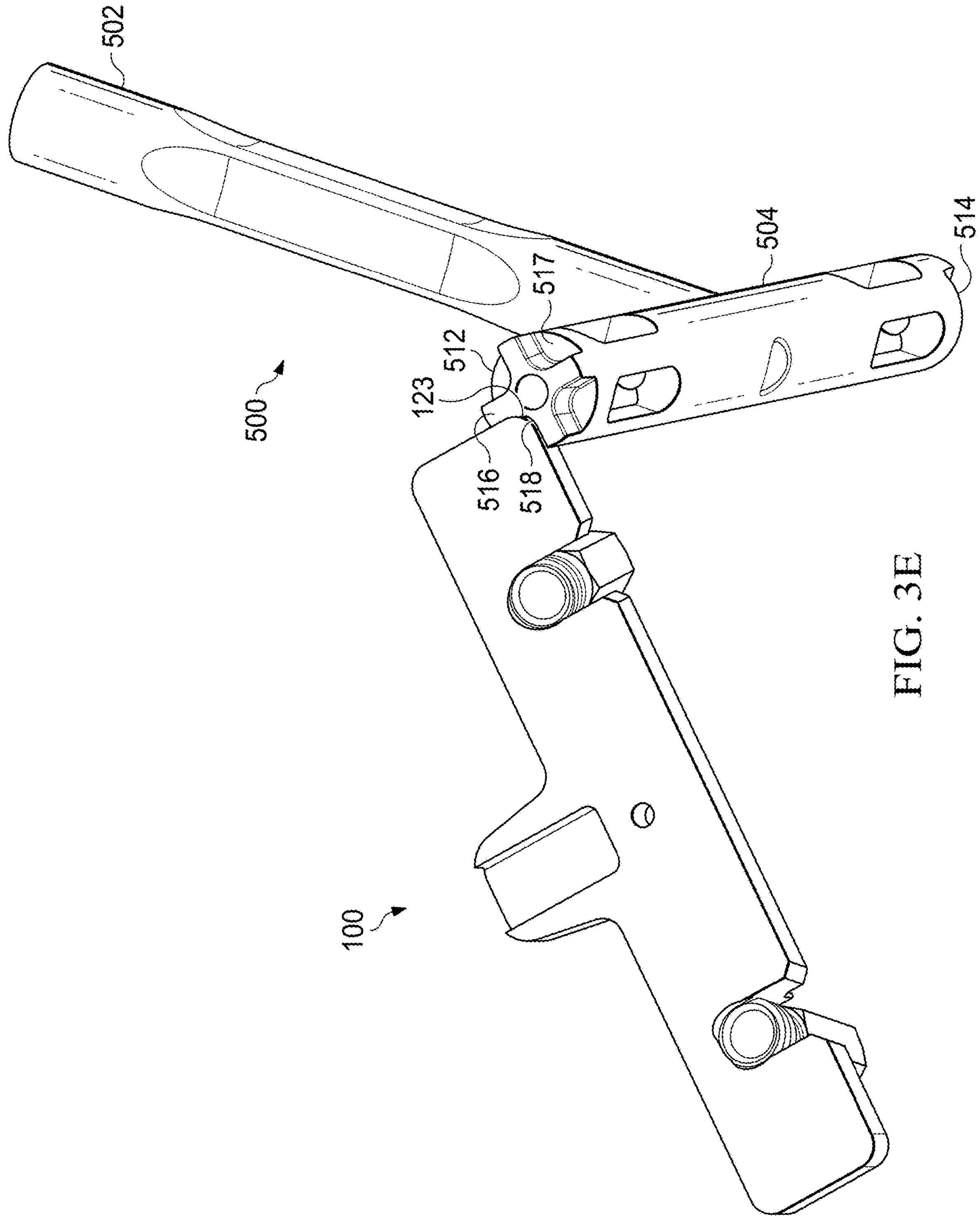
FIG. 3E is a perspective bottom view of the T-shaped drill guide shown in FIG. 3A being used to drill holes around the corners of a plate of a template, according to some embodiments of the present disclosure.
Figure 3F:
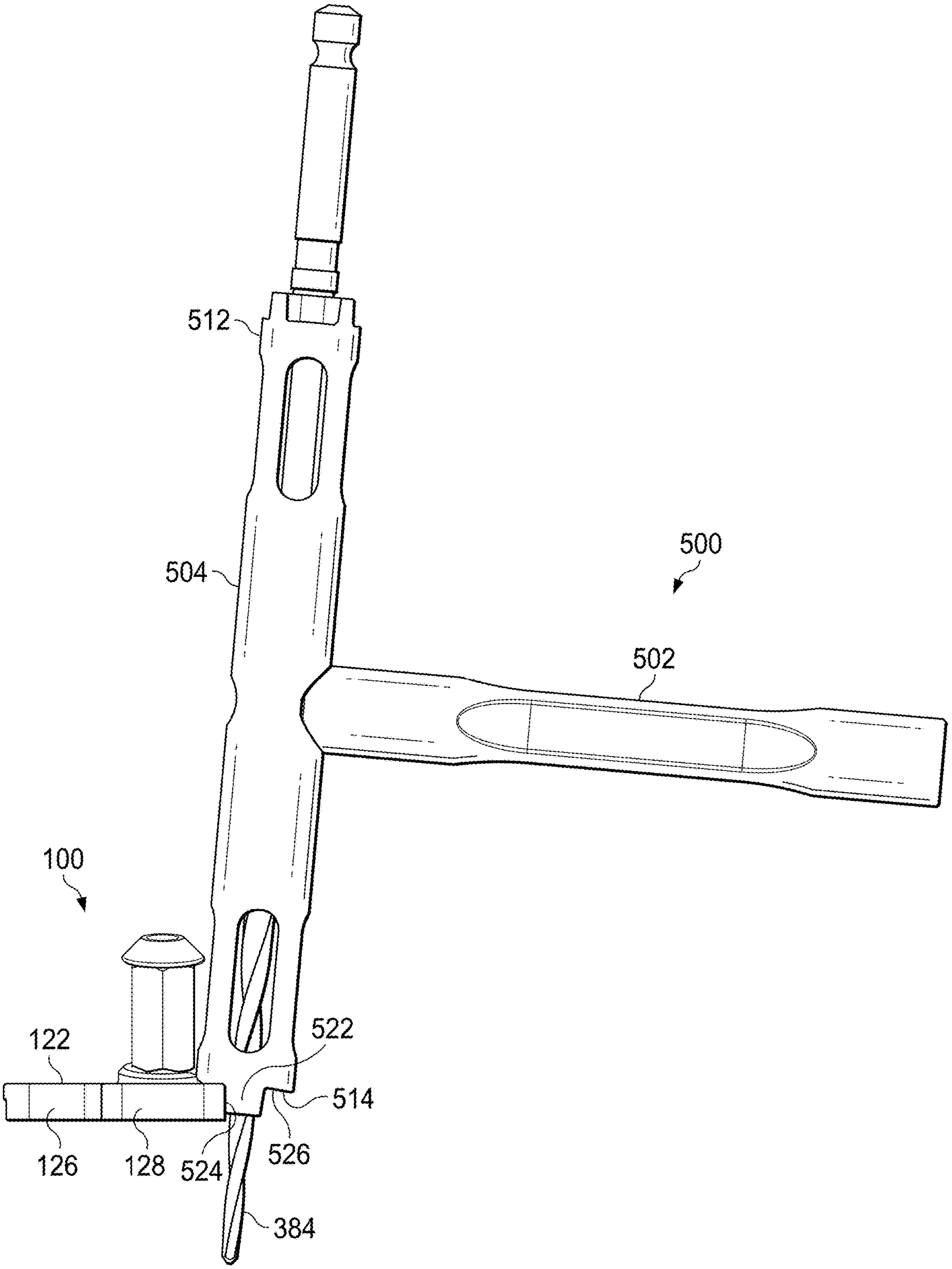
FIG. 3F a perspective side view the T-shaped drill guide shown in FIG. 3A with drill bit inserted and being used to drill holes around the sides of a plate of a template, according to some embodiments of the present disclosure.
Figure 5A:
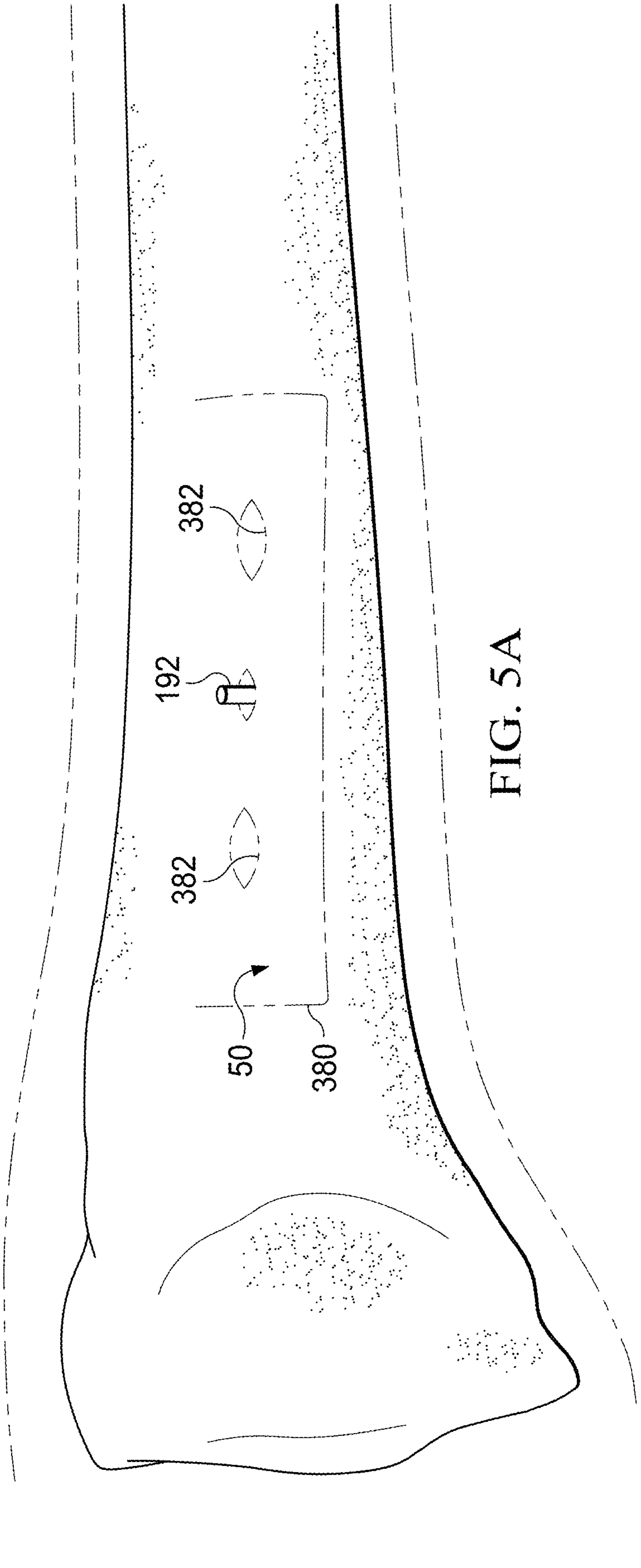
FIGS. 5A-5Q illustrate various steps in the method of FIG. 4, according to some embodiments of the present disclosure.
Figure 5B:
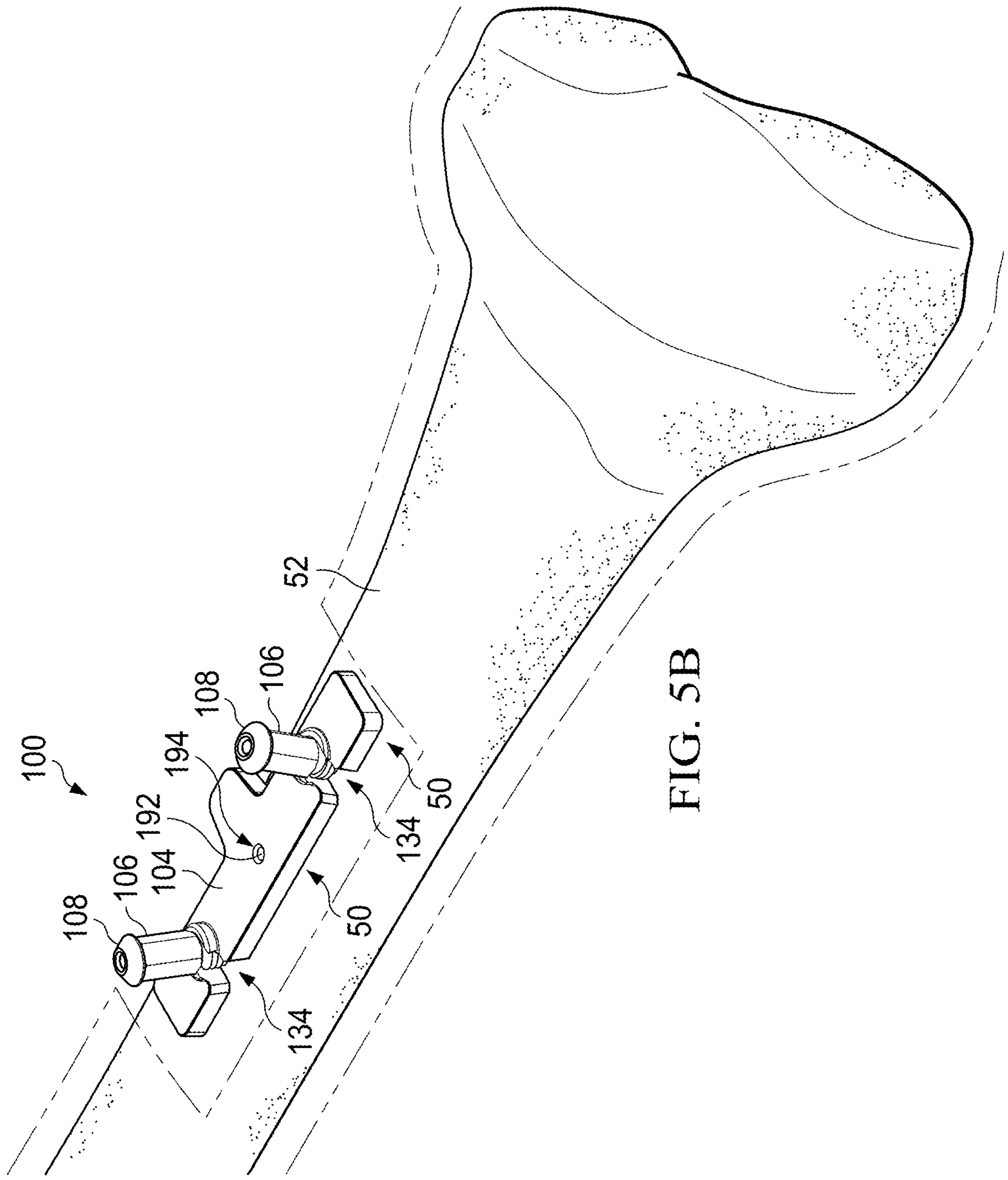
Figure 5C:
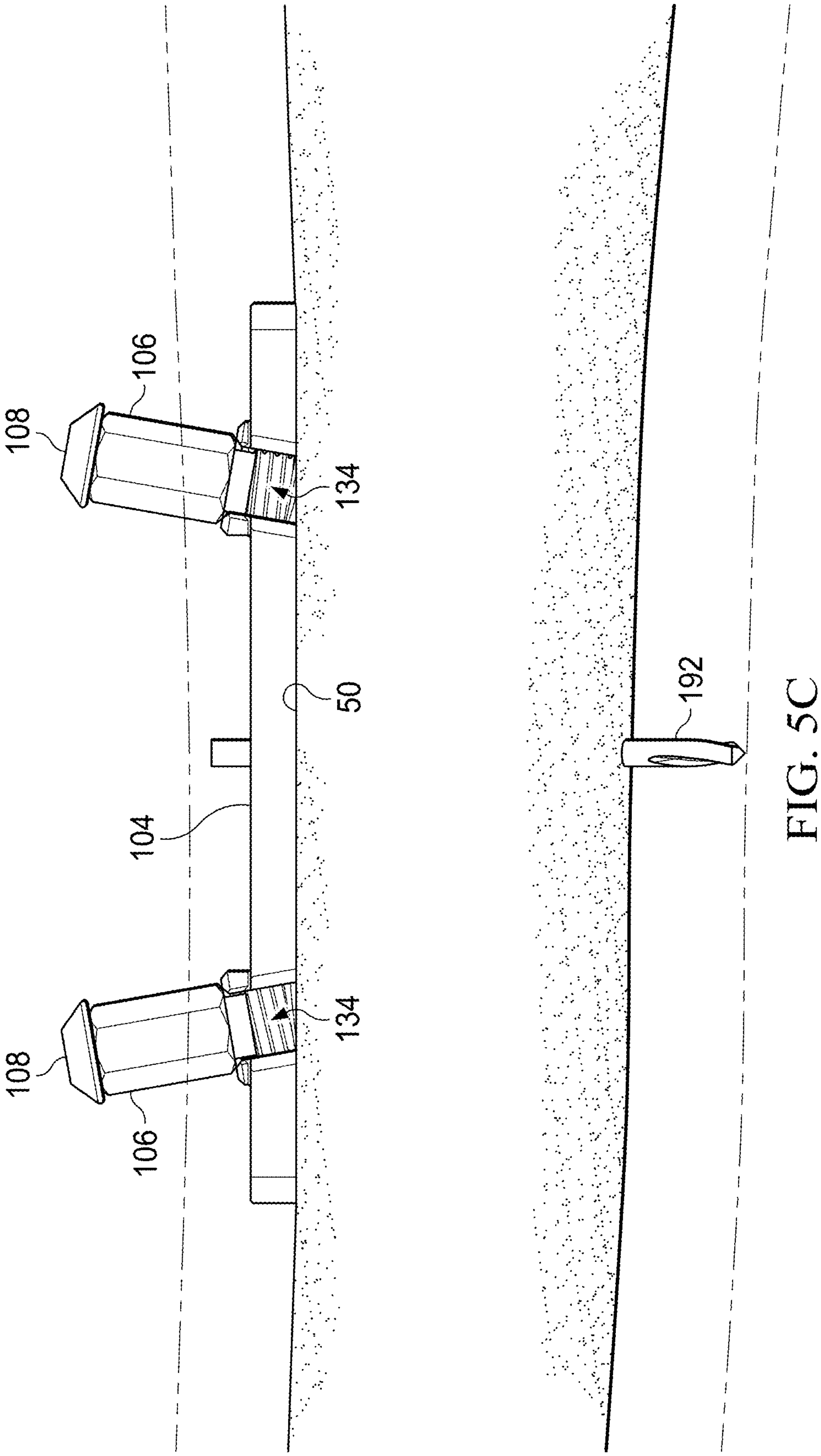
Figure 5D:
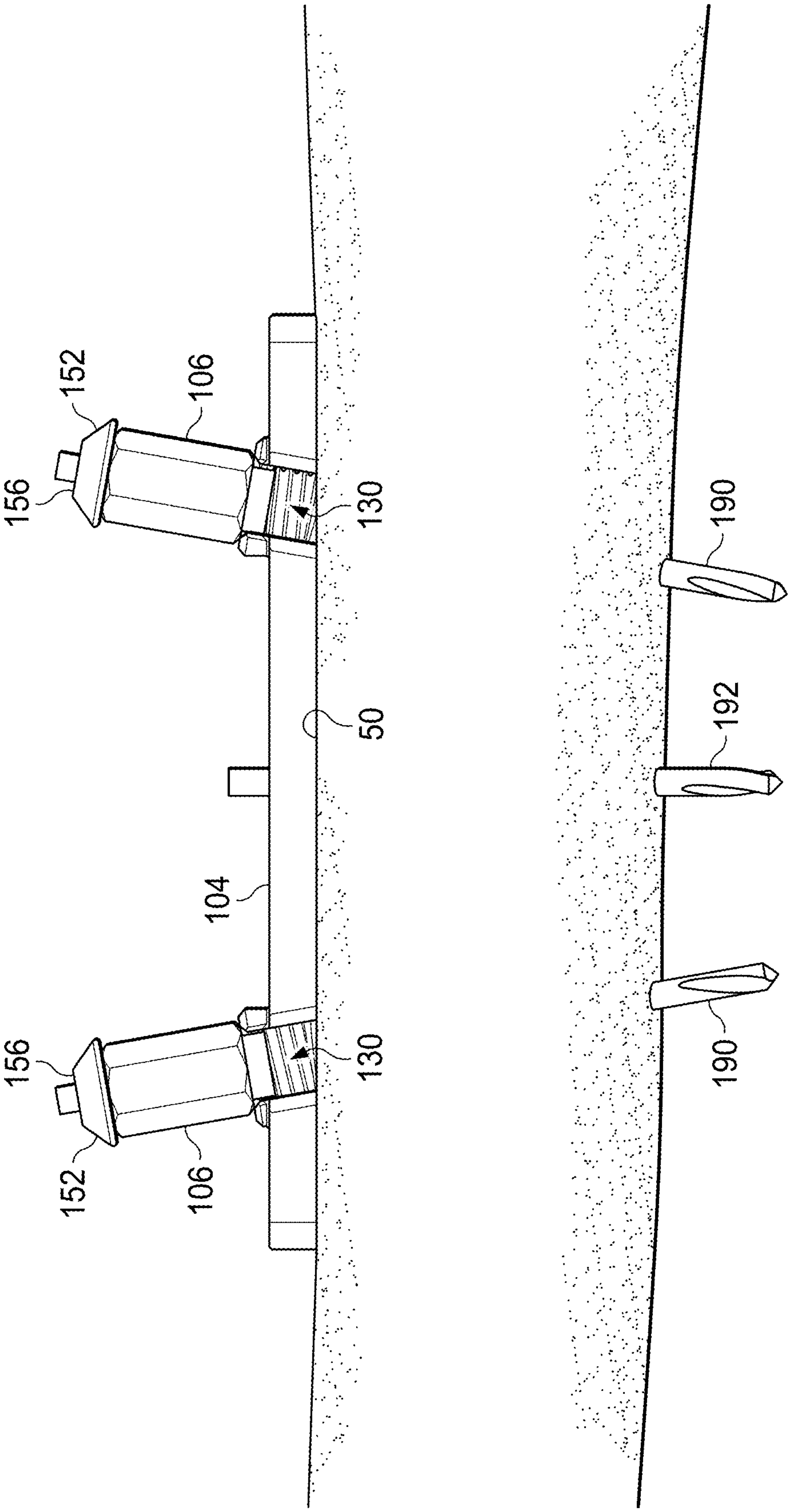
Figure 5E:
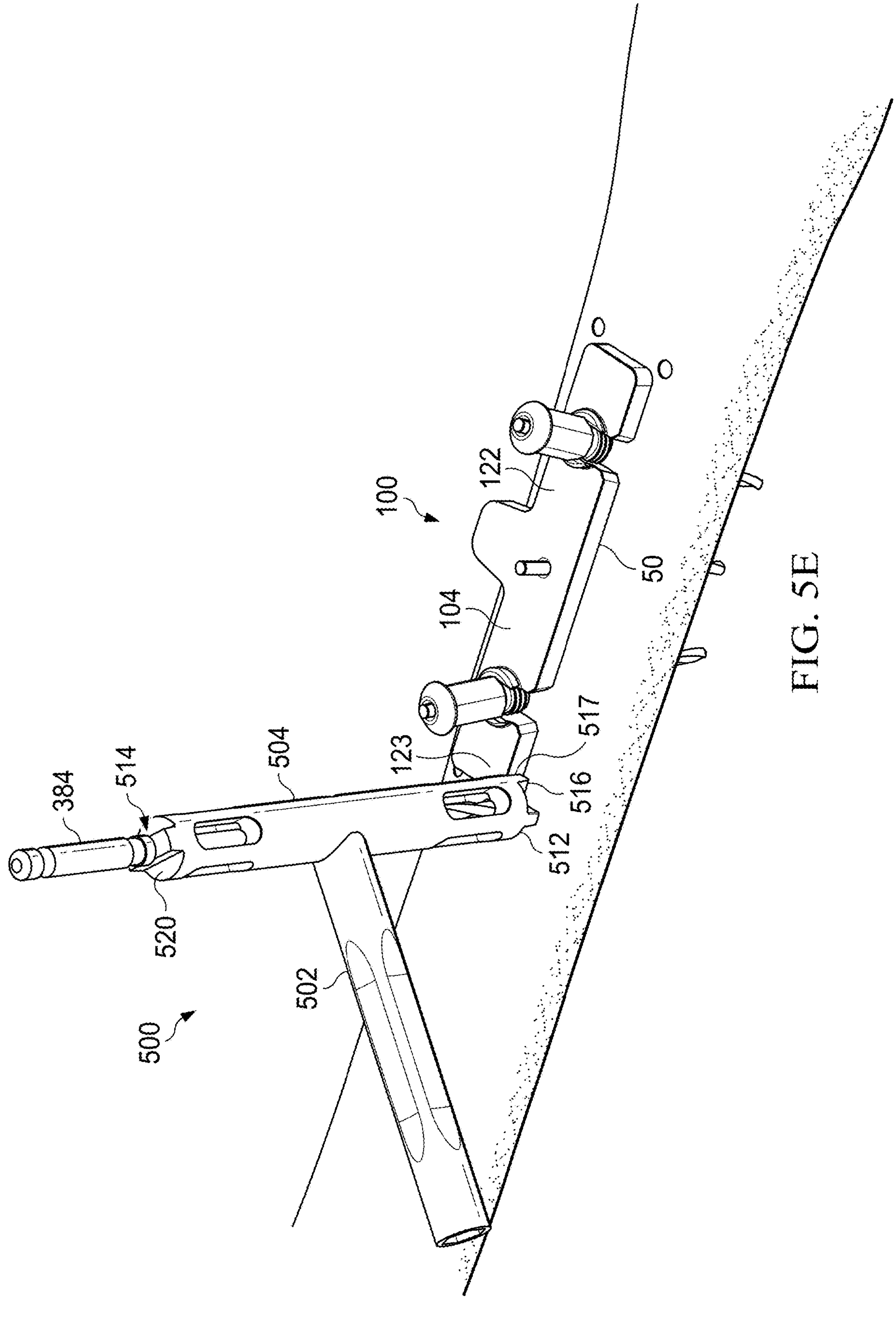
Figure 5F:
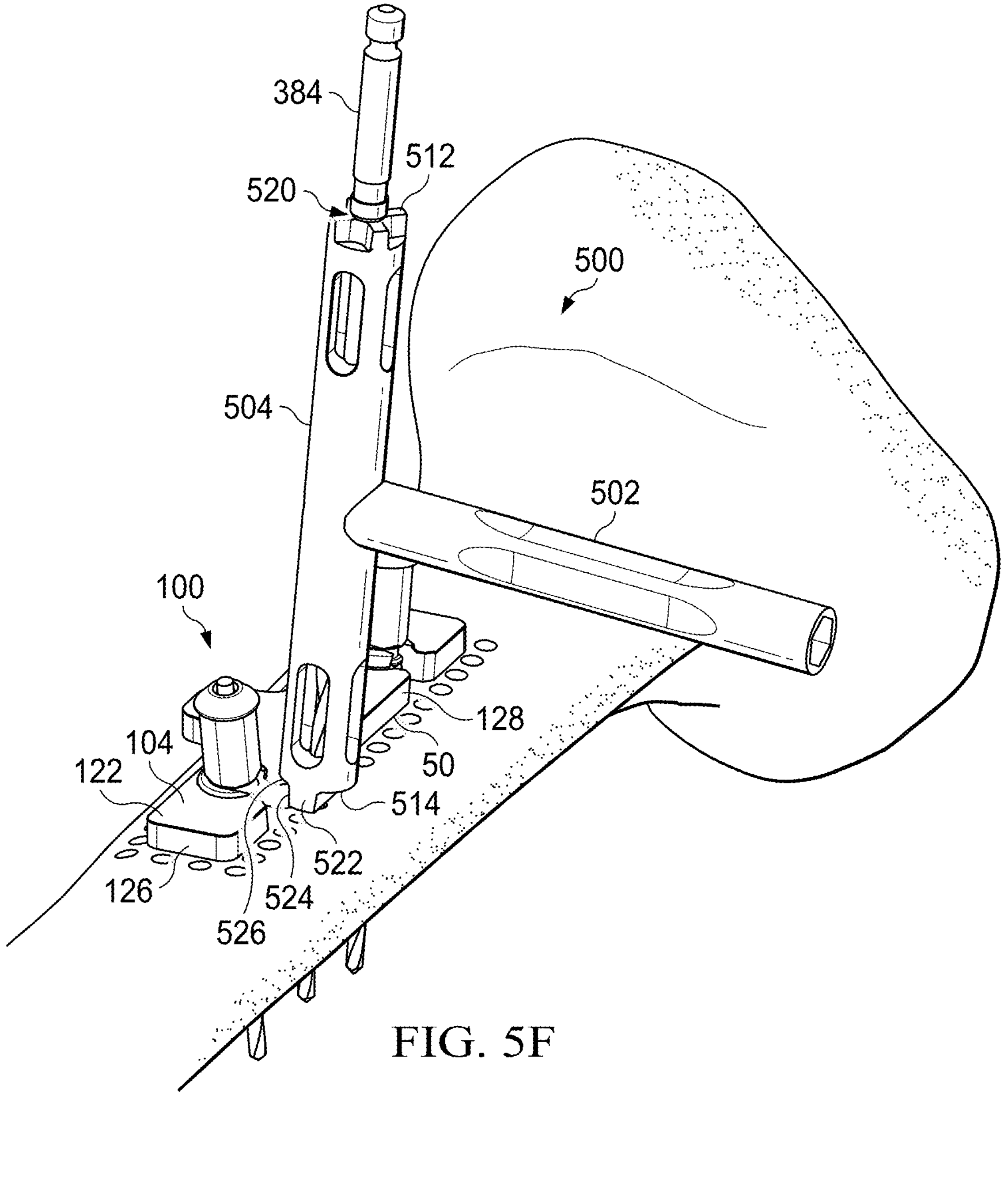

FIGS. 3A-3F illustrate an embodiment of a T-shaped drill guide 500, according to one or more embodiments of the present disclosure. FIG. 3A is a perspective front view, FIG. 3B is a perspective side view, and FIG. 3C is a perspective bottom view of the T-shaped drill guide 500. FIG. 3D is a perspective side view with drill bit 384 inserted and FIG. 3E is a perspective bottom view of the T-shaped drill guide 500 being used to drill holes around the corners of the plate 104 of the template 100. FIG. 3F is a perspective side view of the T-shaped drill guide 500 with drill bit 384 inserted therein being used to drill holes around the sides 128 of the plate 104 of the template 100. After the template 100 is placed on the bone, a T-shaped drill guide 500 may be used to drill holes around the transport segment 50 (as shown in FIGS. 5E-5F) of the bone and remove the half-pin sleeves 106 from the plate 104 around the half-pins 400 (as shown in FIG. 5L).

The T-shaped drill guide 500 includes a half-pin drill-guide shaft 502 and a drill bit guide shaft 504. In some embodiments, the half-pin drill-guide shaft 502 may form the base of the T-shape and the drill bit guide shaft 504 may form the top or cross of the T-shape. The half-pin drill-guide shaft 502 includes an opening 506 that extends from the bottom end 508 to the top end 510. The bottom portion 507 of the opening 506 may be, e.g., hexagonally-shaped (but may be any shape), similar to a socket tool for tightening bolts. The bottom portion 507 of the opening 506 of the half-pin drill-guide shaft 502 may be configured to fit over the hexagonal portion 145 of the half-pin sleeve 106. The half-pin drill-guide shaft 502 may thus be configured to unscrew/unthread the threading 149 of the half-pin sleeve 106 from the threading 148 in the opening 130 of the plate 104. The half-pin drill guide shaft 502 may remove the half-pin sleeves 106 along the longitudinal axis of the half-pins 400 (see e.g., FIG. 5L) (which had been previously inserted through the openings 144 of the half-pin sleeves 106 and into the bone (see e.g., FIGS. 5J-5K). In some cases, the rest of the opening 506 may be cylindrically shaped.

In other embodiments, the opening 506 may be entirely hexagonally-shaped. In yet other embodiments, the entire opening 506 may be cylindrically-shaped.

The drill bit guide shaft 504 may be coupled to the top end 510 of the half-pin drill-guide shaft 502 so that the opening 506 is still accessible through the top end 510. The drill bit guide shaft 504 may have two ends: a first corner-drill end 512 and a second side-drill end 514. The perimeter drill-guide shaft 504 may have an opening 520 that extends from the corner-drill end 512 to the side-drill end 514.

The corner-drill end 512 may be configured to contact a corner 123 of the plate 104. For example, the corner-drill end 512 may include an alignment structure including a projection 516 extending upward from a base surface 517. The projection 516 may be shaped like a cross or a plus-sign such that the corner 123 of the plate 104 fits within a corner 518 of the projection 516. Thus, the projection 516 may have a first wall configured to contact a side 128 of the plate 104 and a second wall configured to contact an end 126 of the plate 104 on either side of the corner 123. The base surface 517 of the corner-drill end 512 may contact, rest, and/or press against the top surface 122 of the plate 104. The opening 520 of the drill-bit guide 504 may extend through the center of the projection 516.

The side-drill end 514 may be configured to contact a side 128 or end 126 of the plate 104. For example, the side-drill end 514 may include an alignment structure including a projection 522 extending upward from the base surface 526. The projection 522 may be linearly-shaped (e.g., may include a wall) such that the side 128 or end 126 of the plate 104 contacts the side 524 of the projection 522. The base surface 526 of the side-drill end 514 may contact, rest, and/or press against the top surface 122 of the plate 104. The opening 520 of the drill-bit guide 504 may extend through the center of the projection 522.

For both ends 512, 514 of the drill-bit guide 504, the base surface 517, 526 is angled relative to the longitudinal axis of the drill-bit guide 504. In some embodiments, the base surfaces 517, 526 are not perpendicular or parallel to the longitudinal axis such that the base surfaces 517, 526 are each angled at an angle of between 0 and 90 degrees relative to the longitudinal axis. The base surfaces 517, 526 may be angled such that, when one of the ends 512, 514 is positioned around the plate 104, the opening 520 of the drill-bit guide 504 is angled towards the plate 104.

As shown in FIG. 3D, when the corner-drill end 512 of the perimeter drill-guide shaft 504 is positioned on the corner 123 of the plate 104, the longitudinal axis of the perimeter drill-guide shaft 504 is angled relative to the top surface 122 of the plate 104. Similarly, as shown in FIG. 3F, when the side-drill end 514 of the perimeter drill-guide shaft 504 is positioned on a side 128 or end 126 of the plate 104, the longitudinal axis of the perimeter drill-guide shaft 504 is also angled relative to the top surface 122 of the plate 104.

Thus, the drill-bit guide 504 guides the drill bit 384 such that it drills holes into the bone that are angled inward towards the plate 104. This results in a transport segment 50 of the bone that is angled inward from the top to the bottom to prevent the transport segment 50 from falling into the base portion 52 of the bone, as described in more detail below in reference to FIG. 6B.

In other embodiments, the projections 516, 522 on the ends 512, 514 of the perimeter drill-guide shaft 504 may be any suitable shape. In some embodiments, one end of the perimeter drill-guide shaft 504 may have a T-shaped projection that can be positioned around both the corners 123 and the sides 128 and ends 126 of the plate 104.

Figure 4:
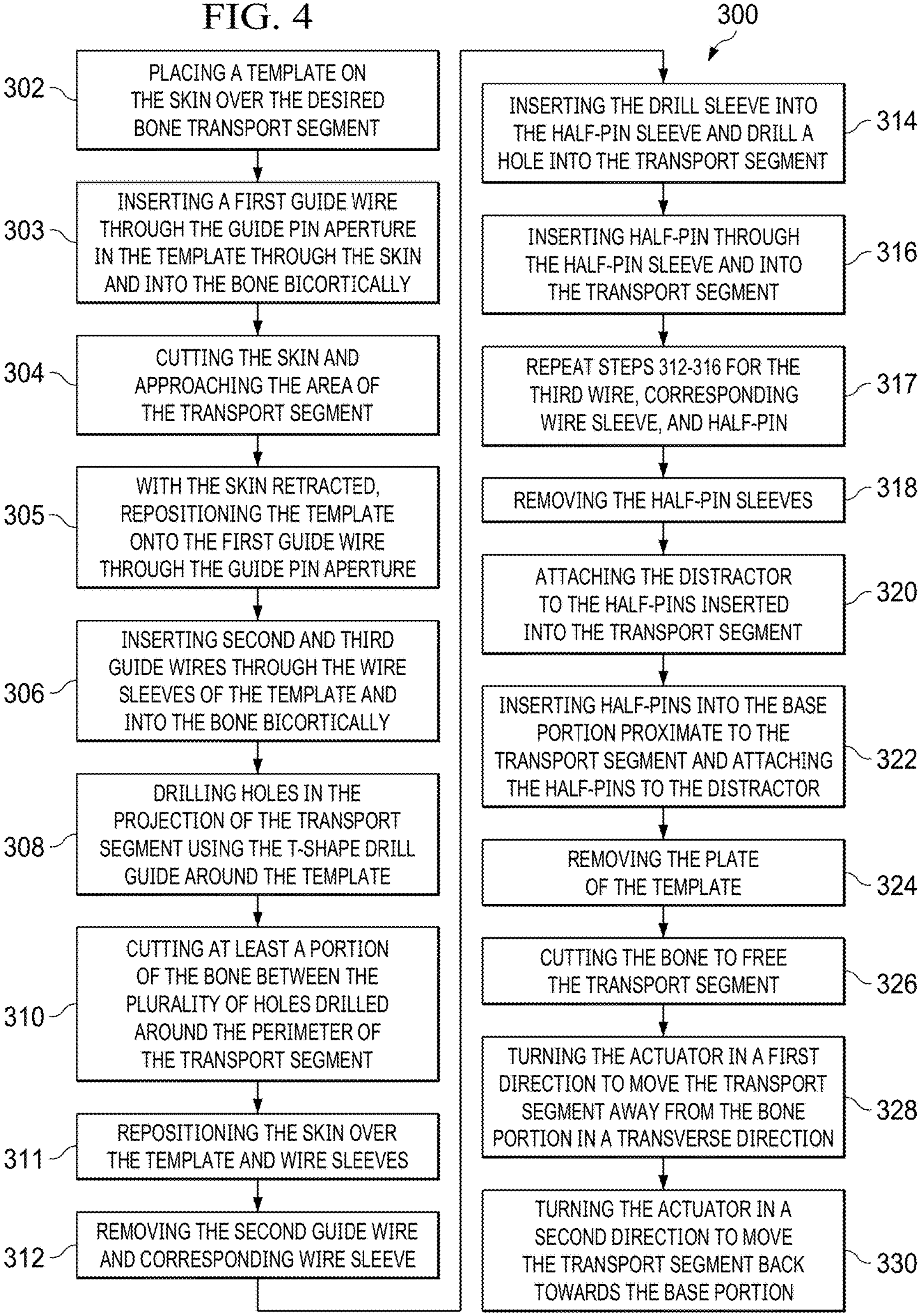
FIG. 4 is a flow chart illustrating a method of using a bone transport system, according to some embodiments of the present disclosure.

FIG. 4 is a flow diagram illustrating an example of a method 300 of performing bone transport using the bone transport system, according to some embodiments of the present disclosure. The method 300 will be described in reference to FIGS. 5A-5Q. The steps 302-330 of method 300 will be explained and illustrated with reference to FIGS. 5A-5Q showing various components of the system applied to patient anatomy.

Any suitable template may be used in accordance with method 300. For example, the embodiment of the template 100 shown in FIGS. 1A-1E is illustrated in FIGS. 5A-5Q. However, any of the templates shown in FIG. 7A-7B or 10A-10L (described in more detail below) may be used with similar methods to that of method 300.

Step 302 of the method 300 shown in FIG. 4 may include placing the plate 104 of a template 100 on the skin over the desired transport segment 50 of the bone. The physician may choose the desired transport segment 50 based on the anatomical structure of the bone, condition of surrounding soft tissues, level of preserved blood supply on the extremity, the ease of access for the bone transport system, or any other appropriate factor. For example, the plate 104 may be placed over a projection of the medullary canal on the medial face of the tibia. The plates' level and orientation may be confirmed using digital C-arm fluoroscopy or stationary digital x-ray.

Step 303 of the method 300 shown in FIG. 4 may include inserting a first guide wire 192 through the guide pin aperture 194 in the plate 104 of the template 100 through the skin and into the bone bicortically. The first guide wire 192 may extend through the skin, subcutaneous soft tissues, and both cortecies of the bone to stabilize the level of the template 100 and to keep the first guide wire 192 as perpendicular to the bone as possible. The first guide wire 192 may be inserted into the desired transport segment 50 of the bone.

Step 304 of the method 300 shown in FIG. 4 may include cutting the skin and approaching the area of the transport segment 50. After inserting the first guide wire 192, the physician may mark the skin around the plate 104 of the template 100. Using the plate 104 as a guide, the physician may use a marker or any other suitable instrument to mark the skin. The skin may be marked around part or all of the perimeter of the upper plate 102. For example, the physician may only mark three sides around the template 100 to delineate a skin flap. In some embodiments, the physician may mark only one or two sides or may mark all four sides around the upper plate 102. In particular, the posterior border 380 of the perimeter of the plate 104 may be marked. The skin may also be marked through the openings 130 of the plate 104. These markings may delineate exit holes 382 within the skin flap. The skin may then be cut along the markings to create a skin flap (cut along at least the posterior side 380), exit holes 832, and a guide wire opening around the first guide wire 192. The first guide wire 192 may be cut along the top surface 110 of the plate 104 so that the end of the first guide wire 192 is flush with the top surface 122. Once the skin flap and the openings are cut, the plate 104 of the template 100 may be removed. The plate 104 may be removed upwards over the first guide wire 192 and off of the skin. FIG. 5A illustrates the bone and the skin (shown as transparent in dotted lines) with the template 100 removed (and thus, not shown) and the first guide wire 192 inserted therein. The cuts along the markings made using the template 100 delineate the flap including the posterior side 380 and the delineating the exit holes 382, as illustrated in FIG. 5A in dotted lines.

Once the cuts are made, the skin flap may be retracted to expose the bone of the transport segment 50. The physician may cut the skin and subcutaneous soft tissue from the skin to the bone. In some embodiments, the physician may cut along part or all of the perimeter markings to form a skin flap. In particular, the physician may make an incision along the posterior border 380 of the perimeter of the tibial midface. This incision may be approximately 10 centimeters (cm). The sides of the perimeter adjacent the posterior side may be cut as well. In some embodiments, these incisions may be approximately 5 mm.

Additionally, the physician may further cut exit holes 382 such that they extend through the skin flap. These exit holes 382 may be sized and shaped to fit over the half-pin sleeves 106 and wire sleeves 108, as described in more detail below in reference to step 311 (see e.g., FIG. 5C). The skin flap may then be retracted or removed from the bone, exposing the transport segment 50. In some embodiments, the physician may stab skin incisions over the marked exit holes 382. The physician may pull the skin up over the first guide wire 192 to open the skin incisions to expose the transport segment 50.

Step 305 of the method 300 shown in FIG. 4 may include, with the skin retracted, repositioning the template 100 onto the first guide wire 192 through the guide pin aperture 194. Step 306 may be illustrated in FIGS. 5B and 5C. FIG. 5B is a top perspective view and FIG. 5C is a side perspective view of the template 100 placed over the first guide wire 192 such that it is disposed on the transport segment 50. The first guide wire 192 may be inserted into the guide pin aperture 194 of the plate 104 to center the plate 104 on the transport segment 50. The physician may adjust the plate 104 to properly align it on the transport segment 50. The physician may position the plate 104 so that the channels 134 of the plate 104 are oriented towards the anterior side of the perimeter (e.g., towards the retracted skin flap). The half-pin sleeves 106 may be disposed in the openings 130 of the plate 104 and the wire sleeves 108 may be disposed in the half-pin sleeves 106. The wire sleeves 108 may be inserted into the half-pin sleeves 106 before or after the half-pin sleeves 106 are inserted into the openings 130 of the plate 104. In some embodiments, sleeves 106, 108 may be assembled after the plate 104 is placed over the transport segment 50.

Step 306 of the method 300 shown in FIG. 4 may include inserting second and third guide wires 190 through the openings 150 of the wire sleeves 108 of the template 100 and into the bone bicortically. Step 306 is illustrated in FIG. 5D (skin and subcutaneous tissue not shown). The second and third guide wires 190 may be inserted by any appropriate means including by drilling or by tapping on the ends of the guide wires 190. In some embodiments, the guide wires 190 may be inserted such that they extend through the entire width of the bone such that they extend through both cortical layers of the bone and through the medullary cavity therebetween. As shown in FIG. 5D, the guide wires 190 may be cut or trimmed along the top 156 of the head 152 of the wire sleeves 108. The guide wires 190 may be cut so that the end of the wires 190 are flush with the top 156 of the head 152 of the wire sleeves 108 and so they do not project above the head 152. Thus, the wires 190 may be relatively smooth along the top 156 of the wire sleeves 108. Cutting the guide wires 190 may make the system easier to work with and may prevent them from scratching, cutting, irritating or otherwise injuring the skin or soft tissue.

As described in more detail above, the openings 130 of the plate 104 (and, thus, the half-pin sleeves 106 and the wire sleeves 108) are angled relative to the top surface 122 of the plate 104. Thus, the wires 190 are inserted such that they are angled inward into the transport segment 50.

Step 308 of the method 300 may include drilling holes in the projection of the transport segment 50 using the T-shaped drill guide 500 around the template 100. First, the physician may drill holes around each corner 123 of the plate 104 using the corner-drill end 512 of the perimeter drill-guide shaft 504 of the T-shaped drill guide 500, as shown in FIG. 5E (skin and subcutaneous tissue not shown). The corner-drill end 512 may be positioned such that the corner 518 of the cross-shaped projection 516 contacts the corner 123 of the plate 104 and the base surface 517 contacts the top surface 122 of the plate 104. A drill bit 384 may then be inserted through the opening 520 of the perimeter drill-guide shaft 504 and into the bone to drill a hole therein. The perimeter drill-guide shaft 504 may angle the drill bit 384 at an angle so that the hole drilled into the bone is angled inward towards the transport segment 50, as described above.

Next, the physician may drill holes around the sides 128 and ends 126 of the plate 104 using the side-drill end 514 of the perimeter drill-guide shaft 504 of the T-shaped drill guide 500, as shown in FIG. 5F (skin and subcutaneous tissue not shown). The side-drill end 514 may be positioned such that the side 524 of the linearly-shaped projection 522 contacts the side 128 (or end 126) of the plate 104 and the base surface 526 contacts the top surface 122 of the plate 104. A drill bit 384 may then be inserted through the opening 520 of the perimeter drill-guide shaft 504 and into the bone to drill a hole therein. Similarly, the perimeter drill-guide shaft 504 may angle the drill bit 384 at an angle so that the hole drilled into the bone is angled inward towards the transport segment 50, as described above.

During this process, the physician may use the half-pin drill-guide shaft 502 of the T-shaped drill guide 500 as a handle to hold and maneuver the perimeter drill-guide shaft 504.

Holes may be drilled along the entire perimeter of the plate 104. In some embodiments, 4-20 holes may be drilled around the perimeter of the transport segment 50. For example, holes may be drilled in the four corners 123 of the plate 104 and along the sides 128 and ends 126 between the corners 123.

Figure 5G:
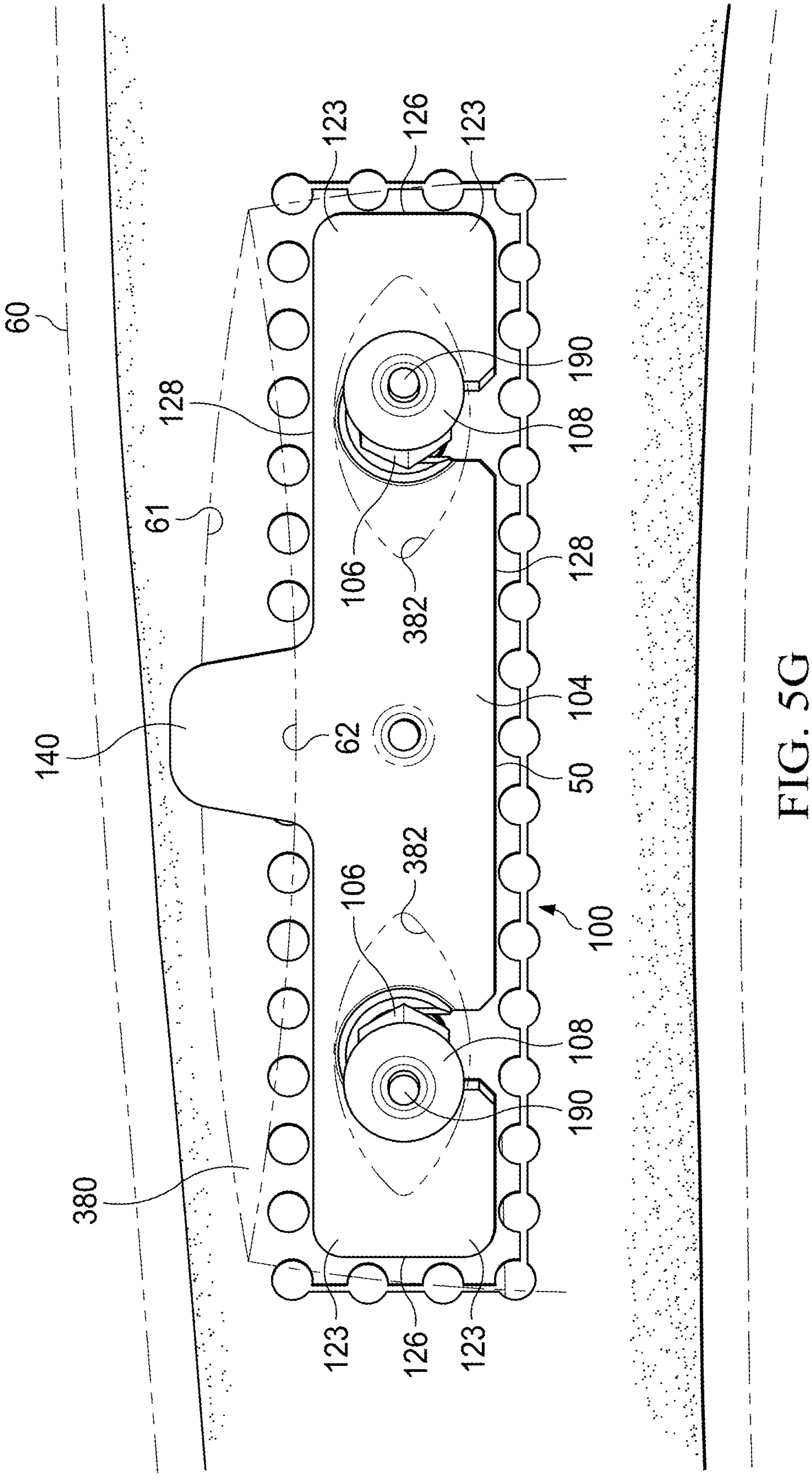

Step 310 of the method 300 may include cutting at least a portion of the bone between the plurality of holes drilled around the perimeter of the transport segment 50, as shown in FIG. 5G (FIG. 5G also illustrates step 311, as described below). The bone may be cut between the holes to cut around at least a portion of the perimeter of transport segment 50. The bone may be cut using any appropriate method, including using an osteotome to manually cut the bone between the drill holes or with powered devices such as a drill or a bone saw. In some cases, only the top layer of the cortical bone may be cut. In other embodiments, part or all of the bone marrow in the medullary cavity may be cut. In a preferred aspect, not all sides of the transport segment 50 may be cut. In some embodiments, 3, 2, or 1 side may be cut. For example, in the embodiment illustrated in FIG. 5G, the posterior side of the transport segment 50 may not be cut.

Step 311 of the method 300 illustrated in FIG. 4 may include repositioning the skin 60 over the template 100 and wire sleeves 108. FIG. 5G may also illustrate the skin flap 62 repositioned over the template 100 and wire sleeves 108 according to step 311. After cutting between holes along the perimeter of the transport segment 50, the skin flap may be replaced over the transport segment 50. The skin flap 62 may be pulled over the plate 104. The half-pin sleeves 106 with wire sleeves 108 and cut guide wires 190 disposed therein may be inserted through the corresponding exit holes 382 in the skin flap 62 so that the complex projects through and extends past the top of the skin flap 62. Thus, the bottom of the skin flap 62, which may have subcutaneous soft tissue, may be disposed directly over and may contact the plate 104, half-pin guides 106 and/or wire guides 108. The tab 140 of the plate 104 may project out of the posterior side 380 of the perimeter of the skin flap 62. As shown in FIG. 5G, the exit holes 382 are defined by two walls of the skin that extend from the top of the skin flap 62 to the bottom. Similarly, an opening may be disposed at the posterior incision 380 between the posterior side of the skin flap 62 and the base portion 61 of the skin adjacent the posterior side of the skin flap 62. The opening may extend from a top to a bottom of the skin. The plate 104 of the template 100 may be removed from the patient via the opening at the posterior incision 380, as described in more detail below in reference to Step 324.

Figure 5H:
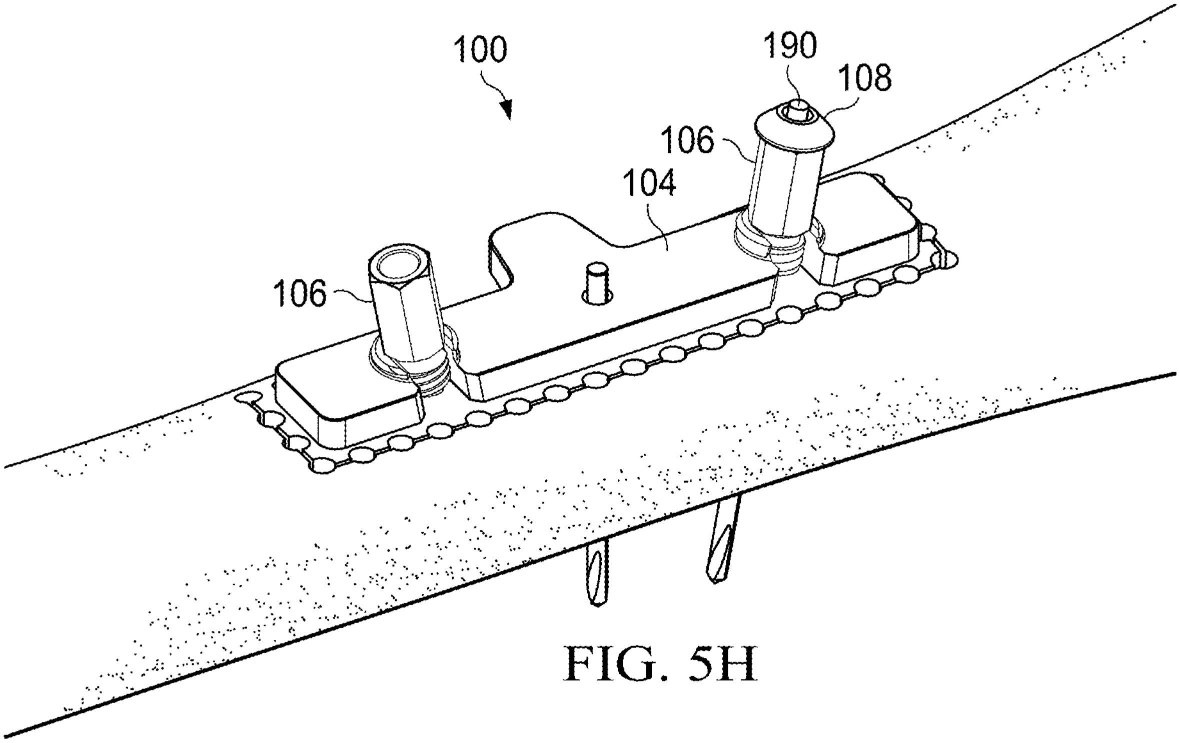

Step 312 of the method 300 shown in FIG. 4 may include removing the second guide wire 190 and corresponding wire sleeve 108. Step 312 is illustrated in FIG. 5H (skin and subcutaneous tissue not shown). The guide wire 190 and wire sleeve 108 may be removed generally laterally or at an angle relative to the axial direction of the bone. FIG. 5H illustrates template 100 after the second guide wire 190 and corresponding wire sleeve 108 have been removed from the pin sleeve 106 (skin and subcutaneous tissue not shown).

Figure 5I:
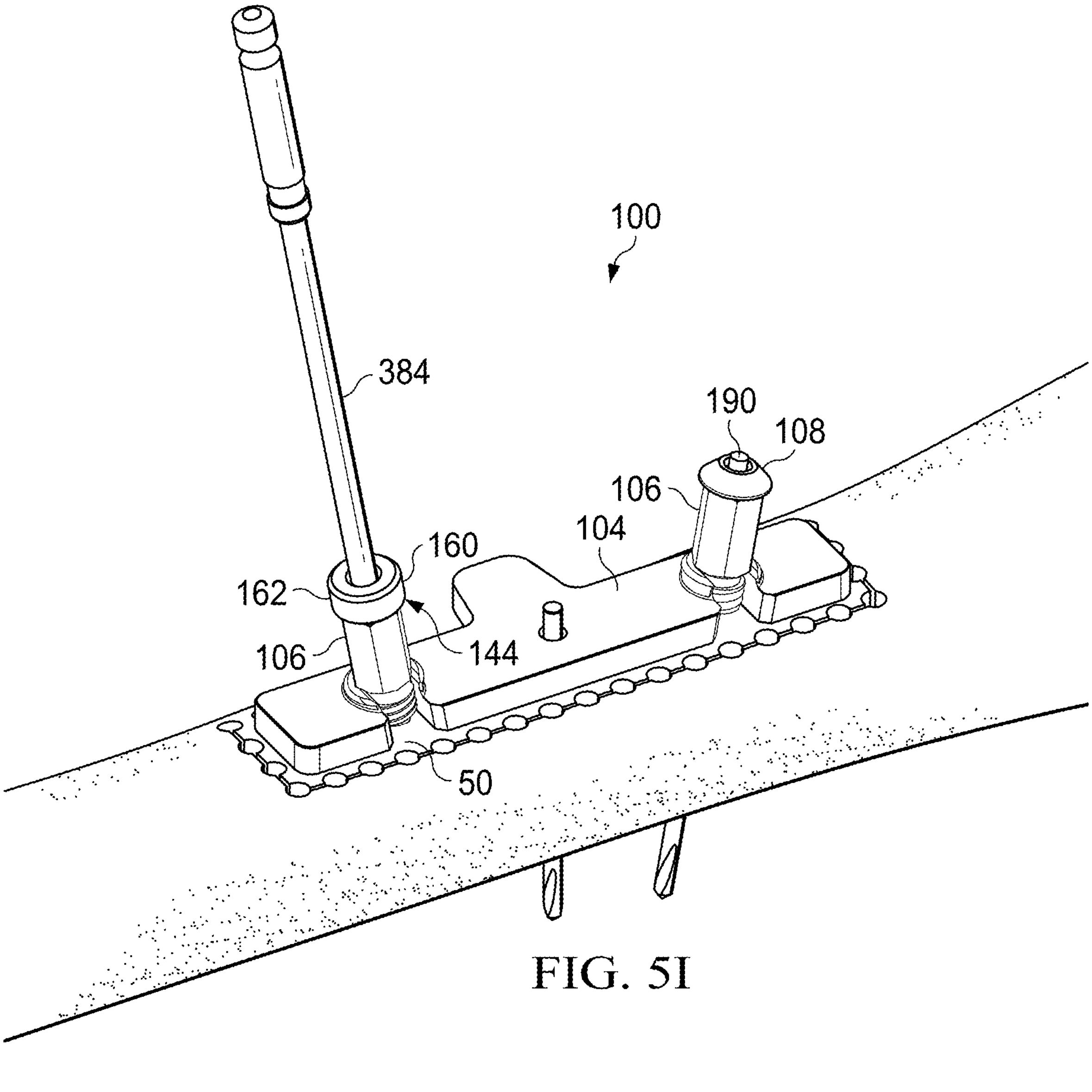

Step 314 of the method 300 shown in FIG. 4 may include inserting the drill sleeve 160 into the half-pin sleeve 106 and drilling a hole into the transport segment 50. Step 314 is illustrated in FIG. 5I (skin and subcutaneous tissue not shown). The shaft 164 of the drill sleeve 160 may be inserted into the opening 144 of the half-pin sleeve 106 such that the head 152 of the drill sleeve 160 contacts the top of the half-pin sleeve 106. A drill bit 384 may then be inserted through the drill sleeve 160 and into the transport segment 50 of the bone to drill a hole therein.

Figure 5J:
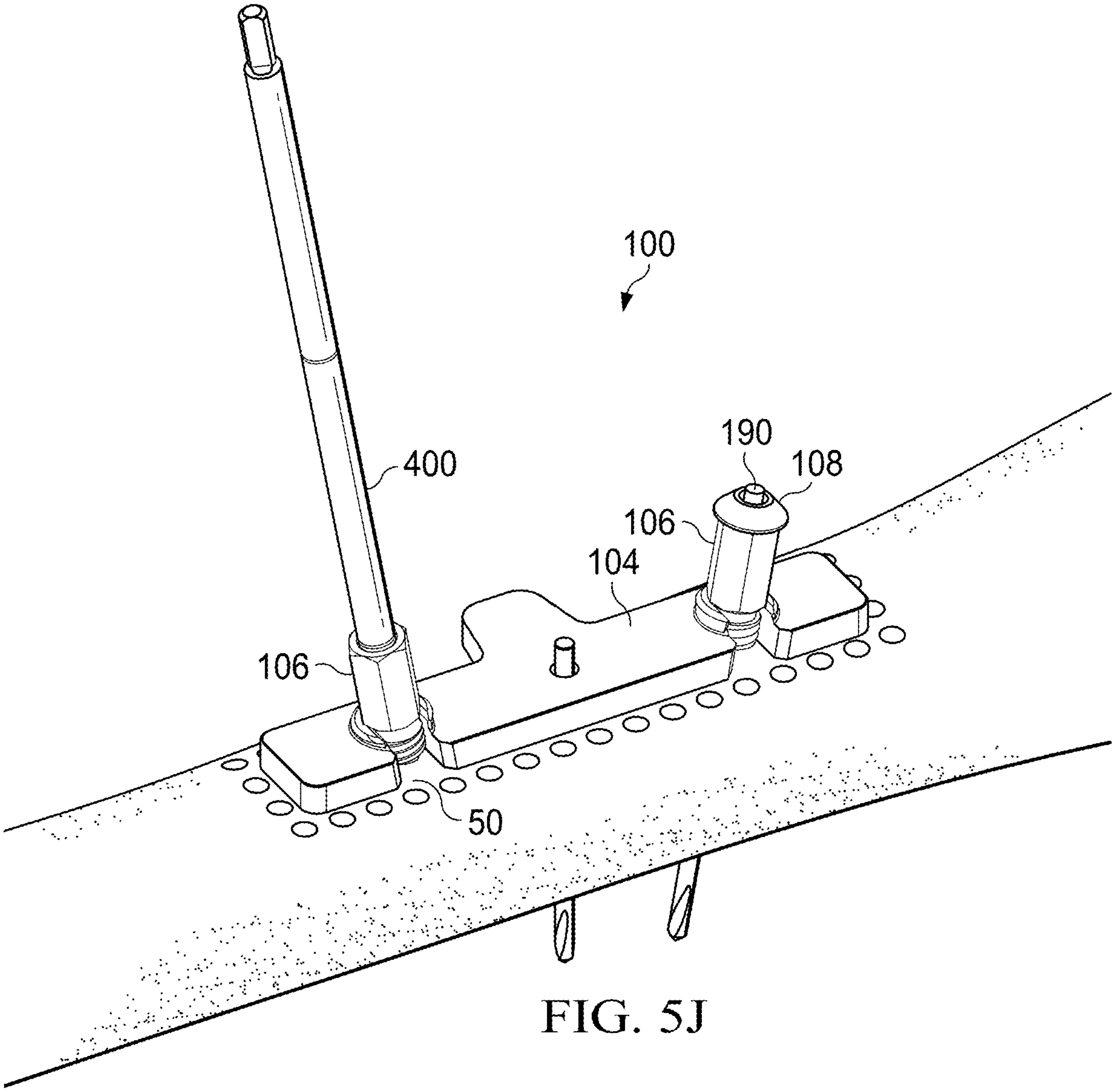

Step 316 of the method 300 shown in FIG. 4 may include inserting a half-pin 400 through the half-pin sleeve 106 and into the transport segment 50. Step 316 is illustrated in FIG. 5J. The half-pin 400 may be inserted using any appropriate method, including by screwing or tapping. The half-pin 400 may be inserted through the half-pin sleeves 106 such that the half-pin 400 is inserted into the transport segment 50 at an angle relative to the top surface 122 of the plate 104 and thus, at an angle relative to the surface of the transport segment 50.

Figure 5K:
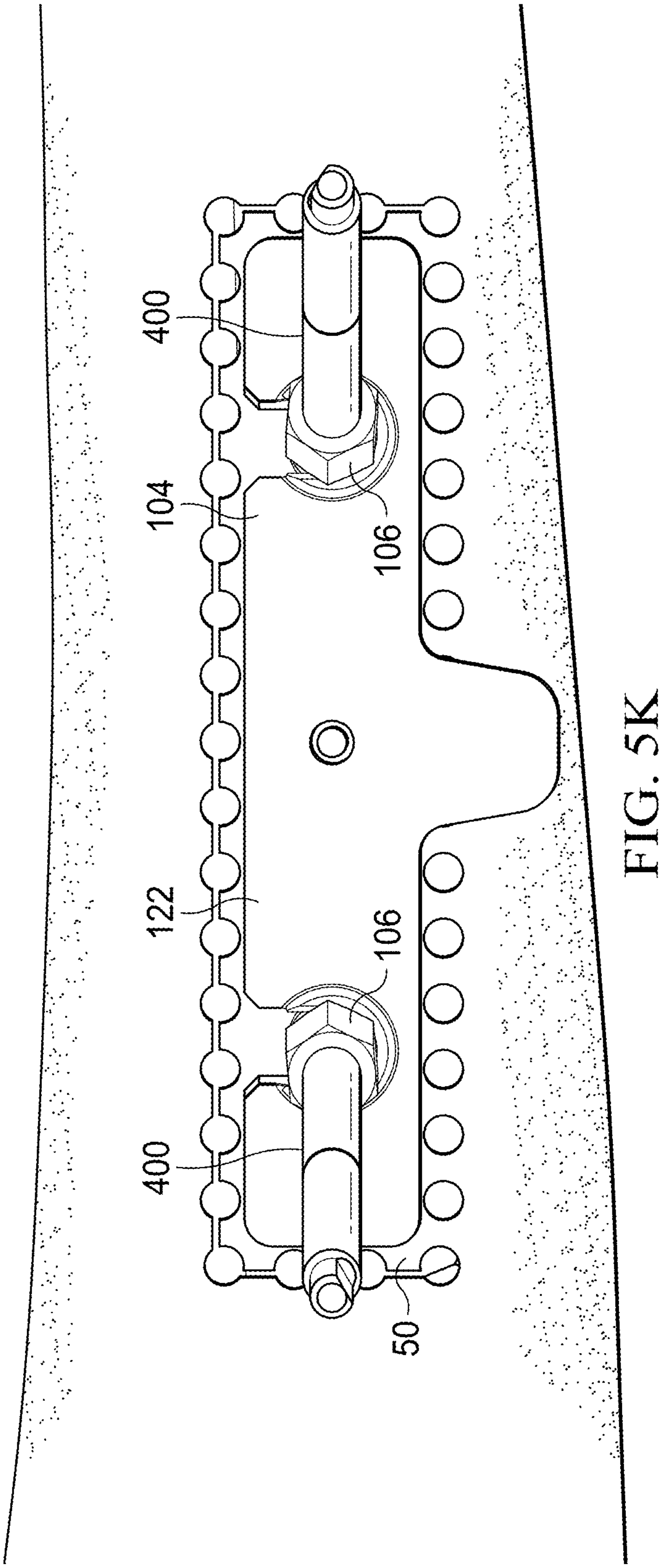
Figure 5L:
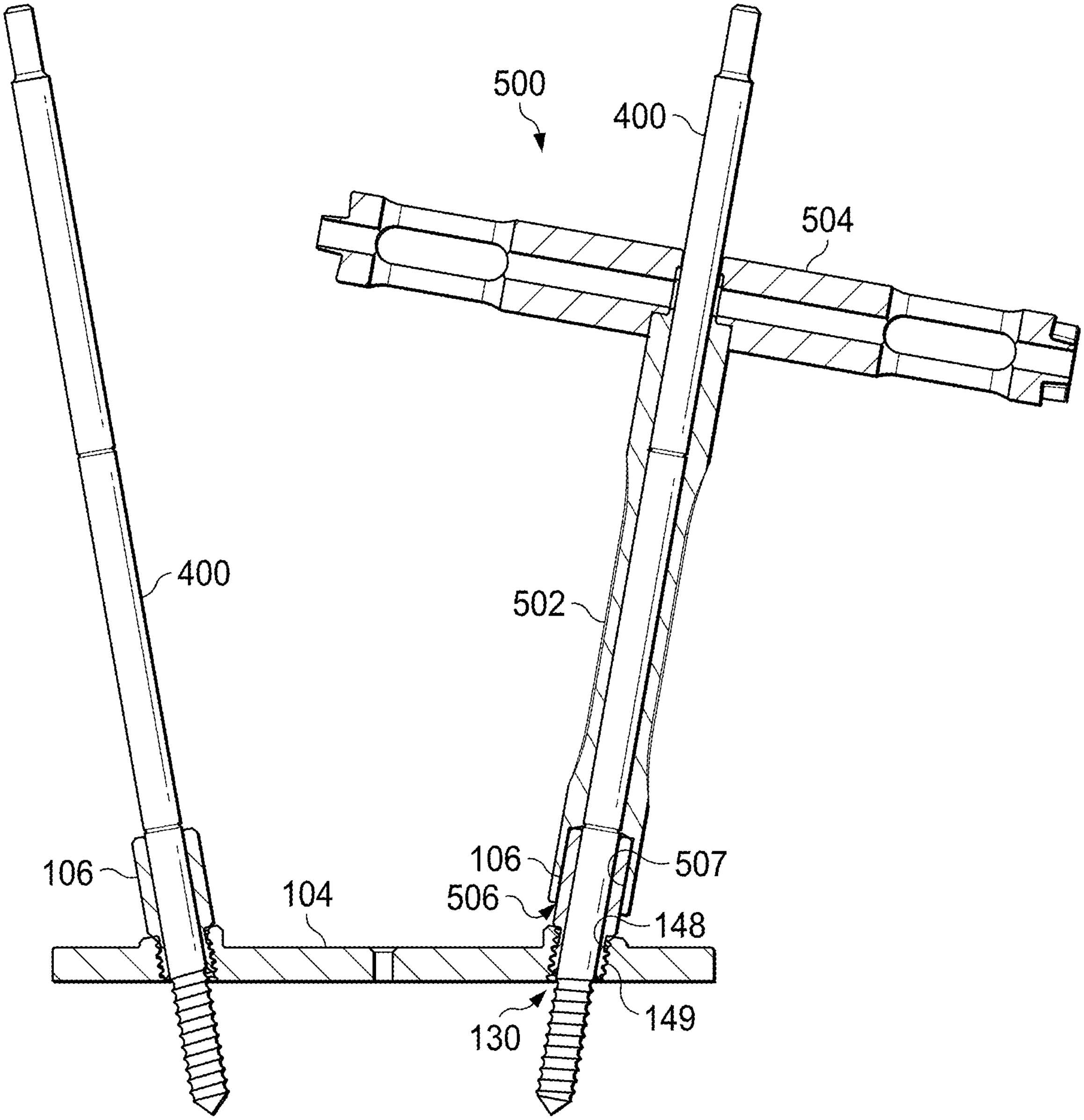

Step 317 of the method 300 shown in FIG. 4 may include repeating steps 312-316 for the third guide wire 190, corresponding wire sleeve 108, and half-pin 400. FIG. 5K illustrates the system after step 317 is performed (i.e. after the wires 190 and wire sleeves 108 have been removed and the half-pins 400 have been inserted through the half-pin sleeves 106 and into the transport segment 50). The skin and subcutaneous tissue is not shown in FIG. 5K, but it should be understood that the plate 104 may be disposed under the skin and the half-pin sleeves 106 and half-pins 400 project through and outward from the skin. In some embodiments, in addition to be angled relative to the top surface 122 of the plate 104, the half-pins 400 may also be angled posteriorly or anteriorly.

Figure 5M:
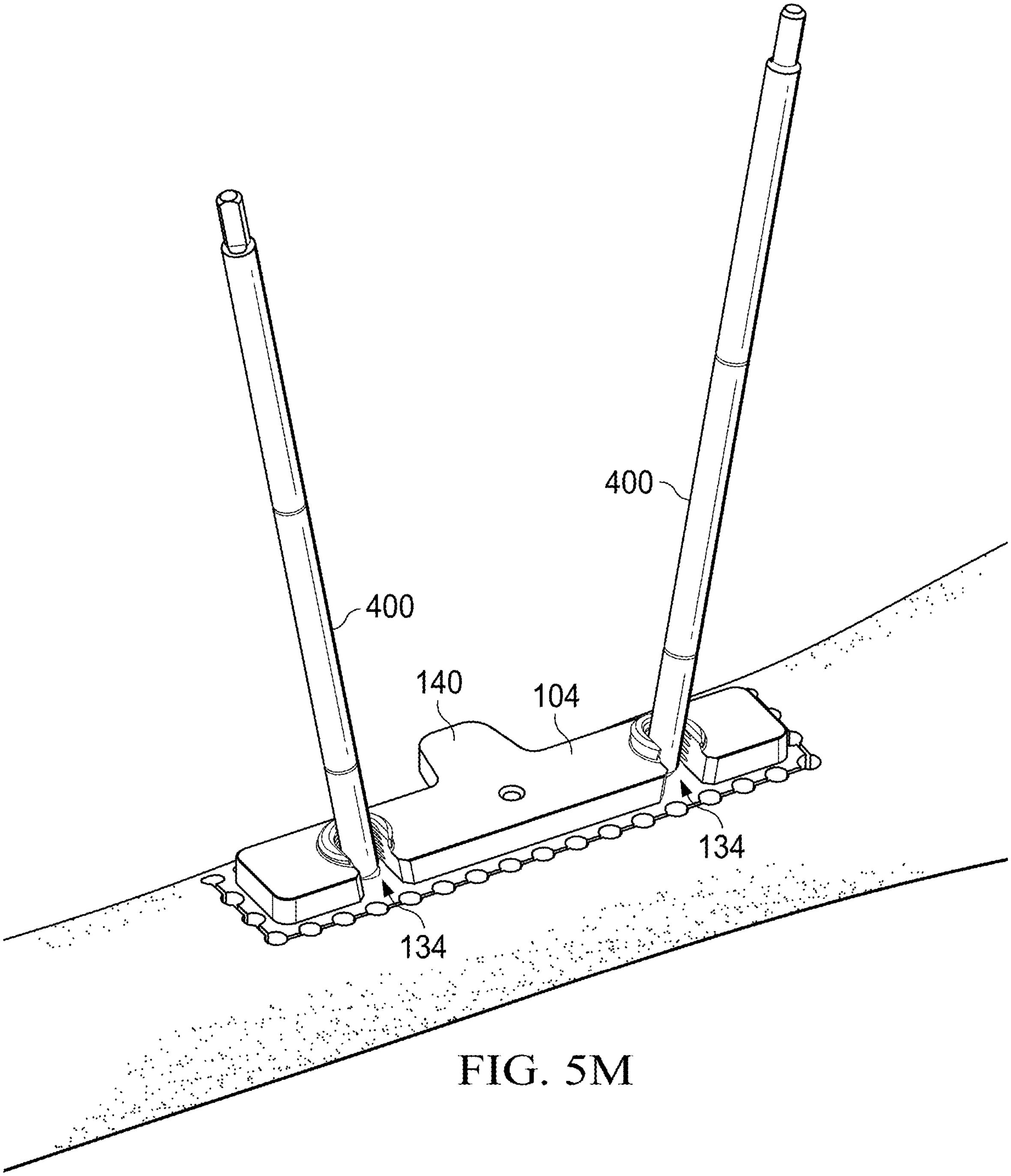

Step 318 of the method 300 shown in FIG. 4 may include removing the half-pin sleeves 106. The half-pin sleeve 106 may be removed from the opening 130 of the plate 104 using the T-shaped drill guide 500, as shown in FIG. 5L (skin and subcutaneous tissue not shown). The half-pin drill-guide shaft 502 of the T-shaped drill guide 500 may be positioned over the half-pin 400 and half-pin sleeve 106 such that the bottom portion 507 of the opening 506 of the half-pin drill-guide shaft 502 is disposed over the plurality of flat surfaces that form the hexagonal portion 145 of the half-pin sleeve 106. The T-shaped drill guide 500 may be rotated to unscrew/unthread the threading 149 on the half-pin sleeve 106 from the threading 148 in the opening 130 of the plate 104. The T-shaped drill guide 500 may remove half-pin sleeves 106 upward along the longitudinal axis of the half-pins 400. During this process, the physician may use the perimeter drill-guide shaft 504 as a handle to maneuver the half-pin sleeve 106. FIG. 5M illustrates the system after step 318 (i.e. after the half-pin sleeves 106 have been removed).

In some embodiments, the first guide wire 192 may be removed after the half-pin sleeves 106 are removed. However, in other embodiments, the first guide wire 192 may be removed before the half-pin sleeves 106 are removed. The first guide wire 192 may be removed upward and generally perpendicularly from the top surface 122 (see e.g., FIG. 5K) of the plate 104.

Figure 5N:
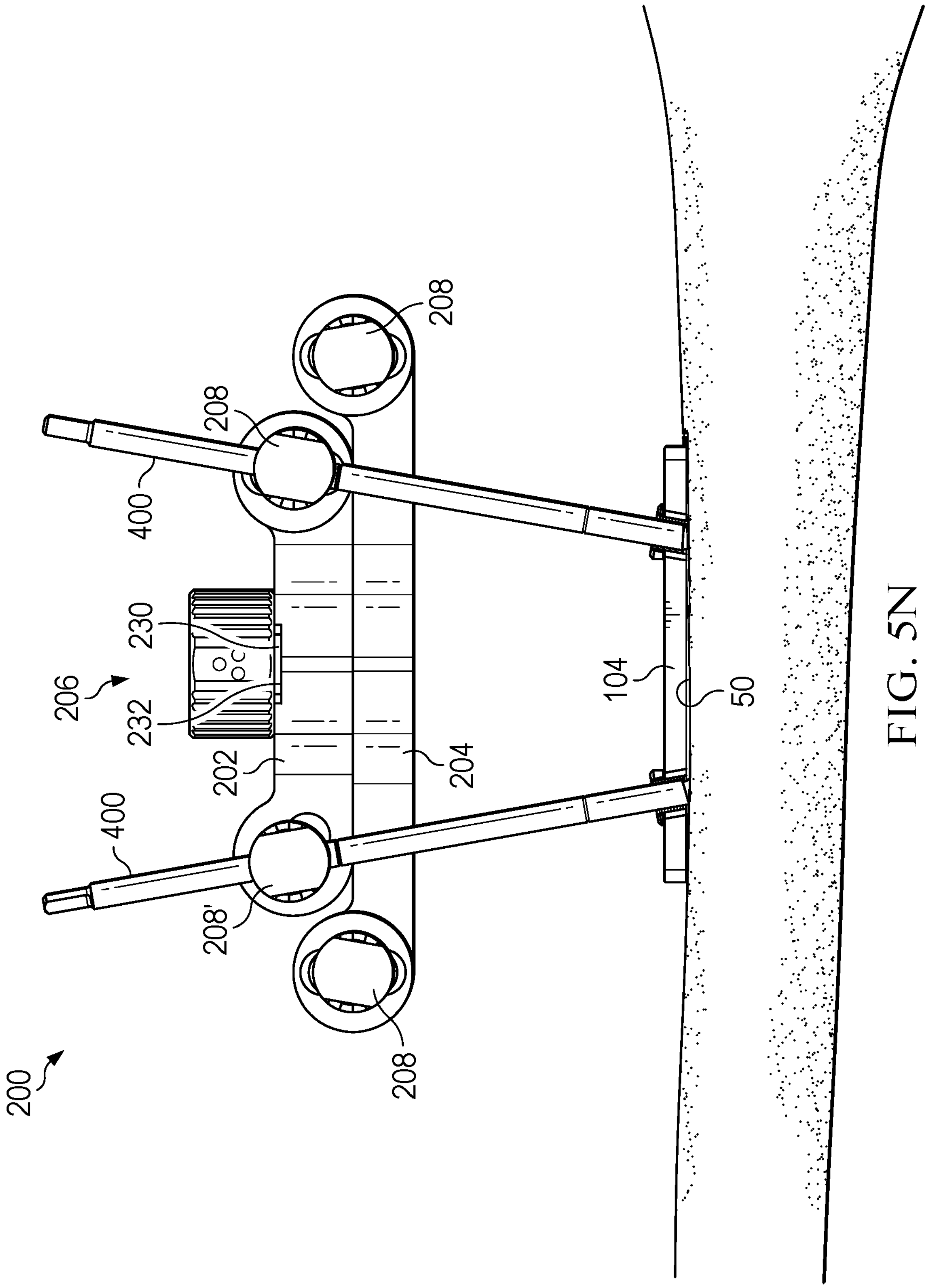

Step 320 of the method 300 shown in FIG. 4 may include attaching a distractor 200 to the half-pins 400 inserted into the transport segment 50. Step 320 is illustrated in FIG. 5N (skin and subcutaneous tissue not shown). The half-pin holders 208, 208' of the upper beam 202 of the distractor 200 may be placed over the half-pins 400. The half-pin holders 208, 208' may be moved, rotated, pivoted, or swiveled to fit over the inserted half-pins 400, which may be inserted at an angle relative to the surface of the transport segment 50. The nuts 220, 220' (see e.g., FIG. 5O) of the half-pin holders 208, 208' may be tightened to tighten the half-pin holders 208, 208' around the half-pins 400 and secure the distractor 200 to the half-pins 400.

Figure 5O:
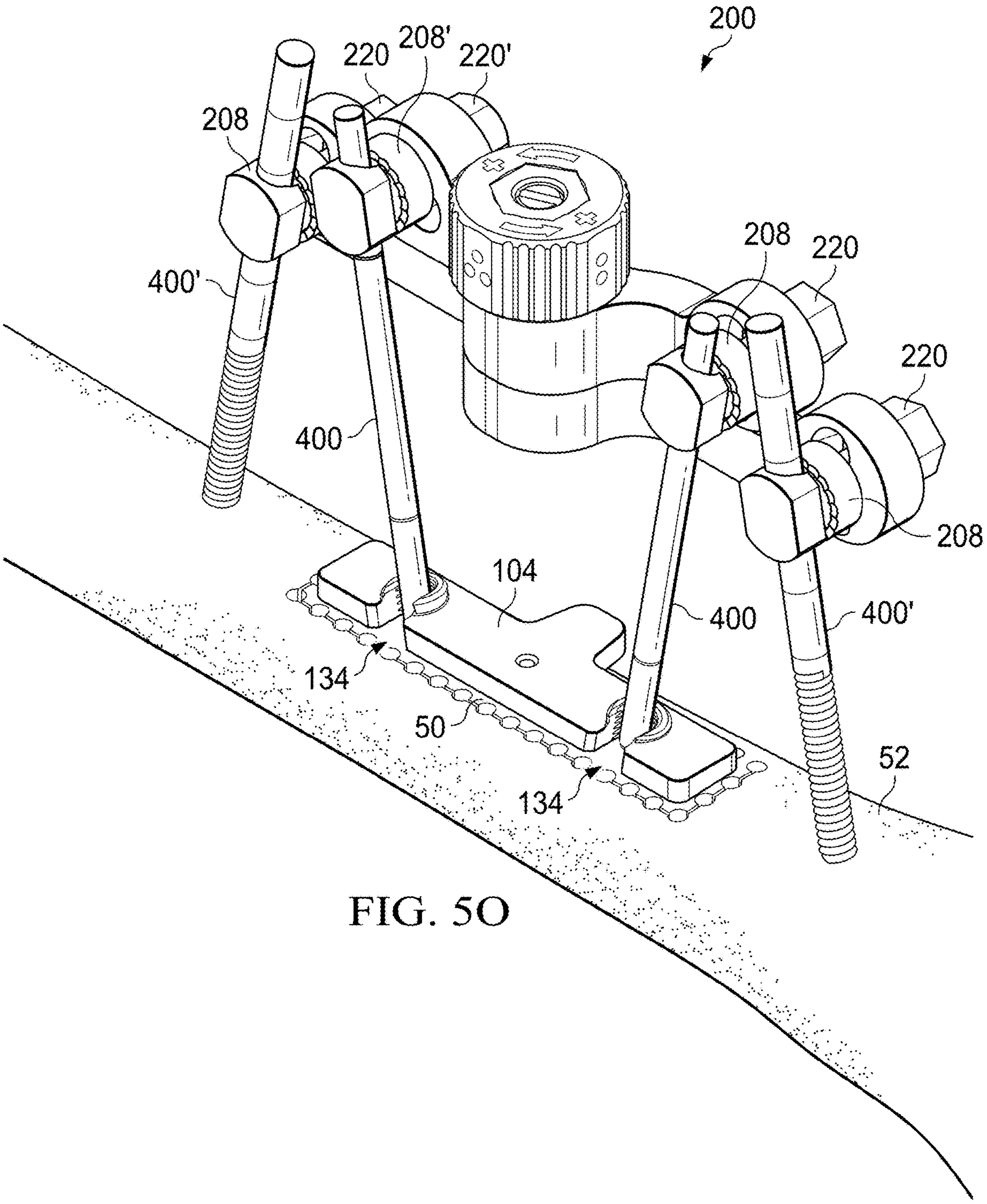

Step 322 of the method 300 shown in FIG. 4 may include inserting half-pins 400' into the base portion 52 of the bone proximate to the transport segment 50 and attaching the half-pins 400' to the distractor 200. Step 322 is illustrated in FIG. 5O (skin and subcutaneous tissue not shown). The half-pins 400' inserted into the base portion 52 may be the same as or different from the half-pins 400 inserted into the transport portion 50 as described in more detail below. In some embodiments, the half-pins 400' inserted into the base portion 52 may be bi-cortical and may extend through the entire bone, through both cortical layers. Thus, the half-pins 400' inserted into the base portion 52 may be stationary relative to the half-pins 400 inserted into the transport segment 50. The half-pin holders 208 of the lower beam 204 of the distractor 200 may be placed over the half-pins 400' inserted into the base portion 52. The half-pin holders 208 may be moved, rotated, pivoted, or swiveled to fit over the inserted half-pins 400', which may be inserted at an angle relative to the surface of the base portion 52. The nuts 220 of the half-pin holders 208 may be tightened to tighten the half-pin holders 208 around the half-pins 400' and secure the distractor 200 to the half-pins 400'. The half-pins 400' may be inserted into the base portion 52 before or after they are attached to the distractor 200. The half-pins 400' may be inserted using any appropriate method, including by screwing or tapping.

In some embodiments, one or more of the half-pins 400, 400' may be cut or trimmed. The physician may cut or trim the half-pins 400 to make the bone transport system easier to handle or so that the half-pins 400, 400' do not get in the way of the distractor 200 during distraction and contraction.

Figure 5P:
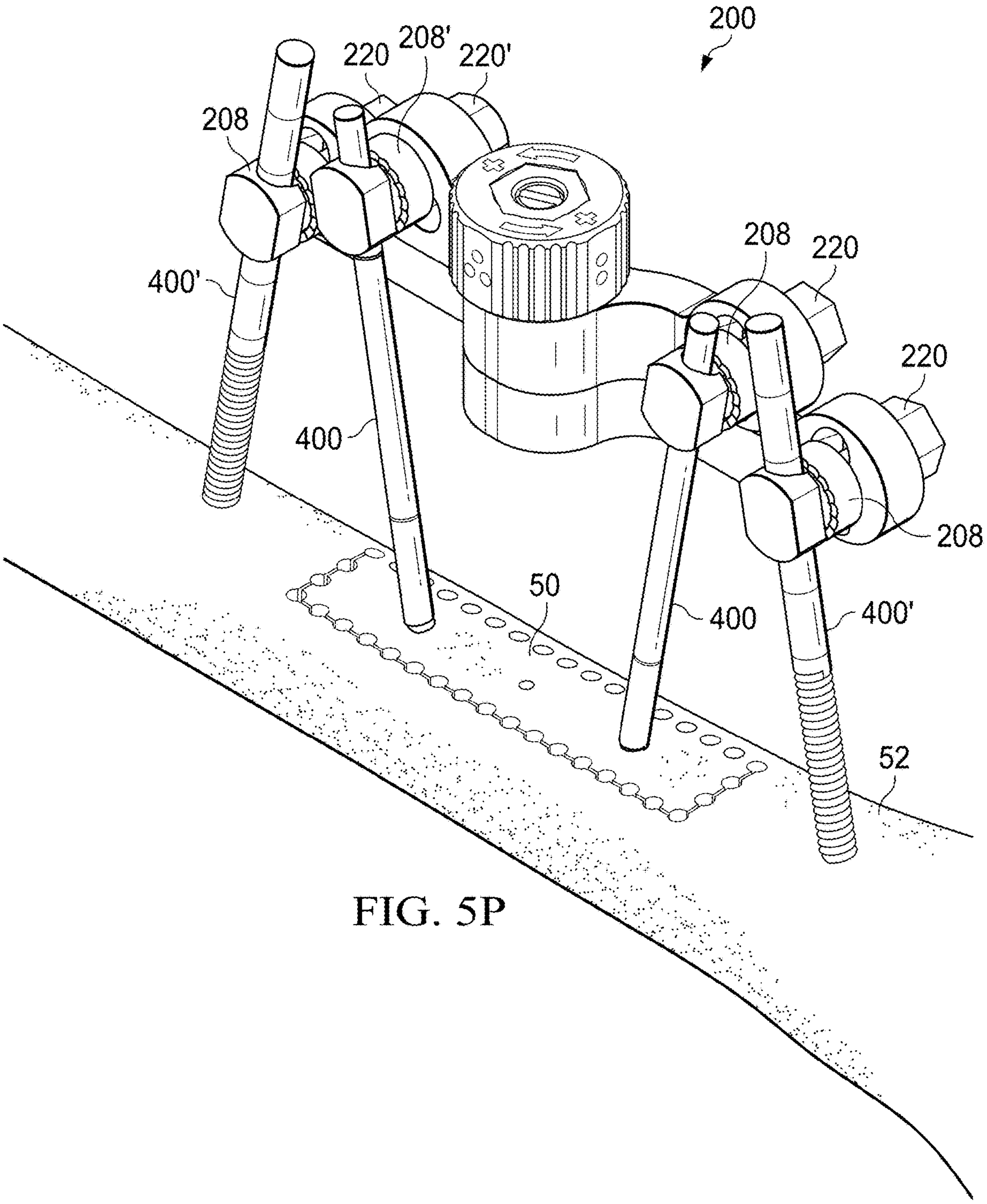
Figure 5Q:
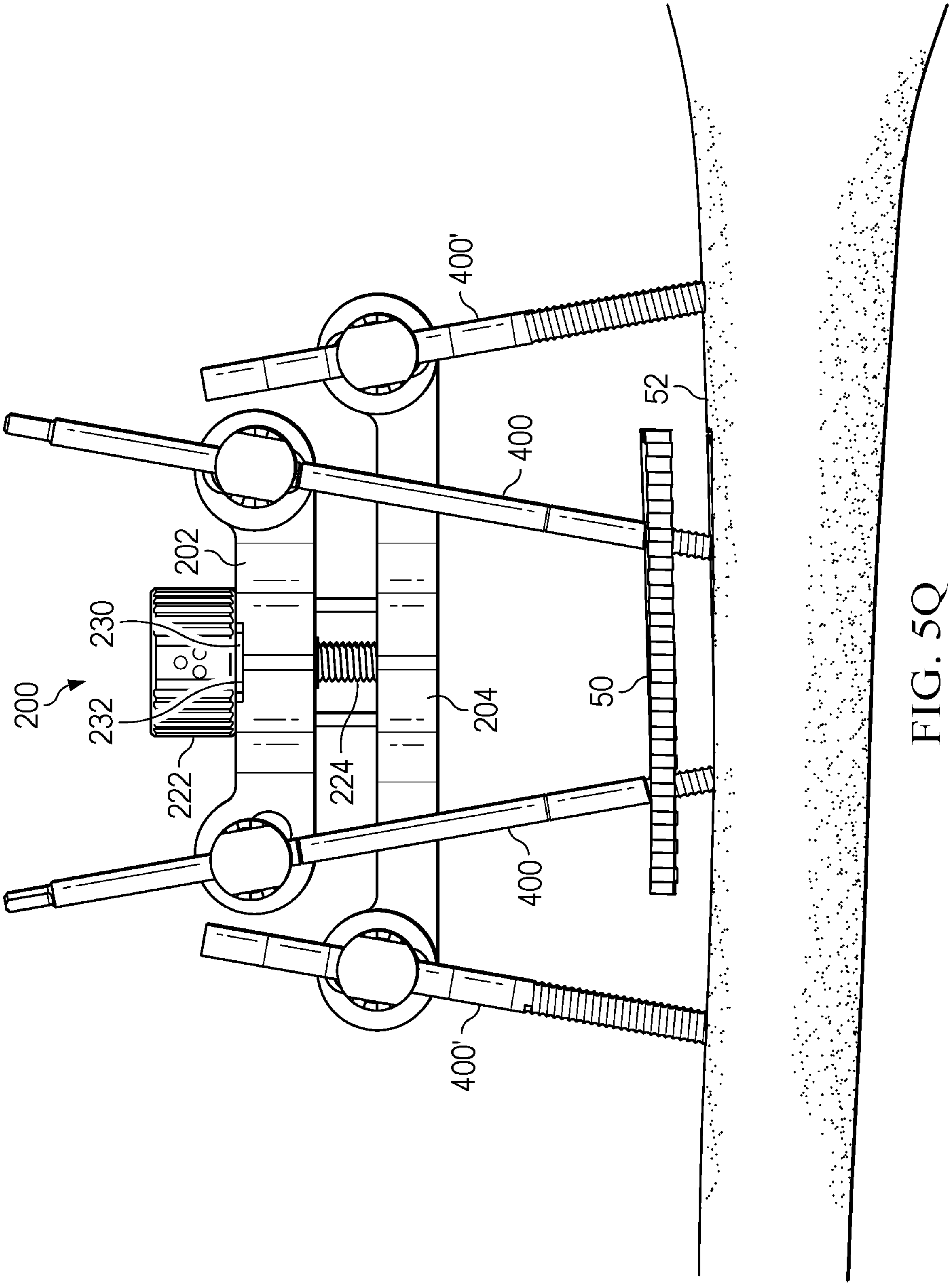

Step 324 of the method 300 shown in FIG. 4 may include removing the plate 104 of the template 100. Because the half-pin sleeves 106 have a diameter 146 that is larger than the width 138 of the channel 134 of the plate 104 and the width 138 of the channel 134 is greater than a diameter 408 of the half-pins 400 in the transport portion 50, the plate 104 cannot be removed until the half-pin sleeves 106 are removed (see e.g., FIG. 1A). Moreover, the first guide wire 192 must be removed before the plate 104 can be removed (see e.g., FIG. 5J). Once the half-pin sleeves 106 and first guide wire 192 are removed (see e.g., FIGS. 5H-5J and 5L), the plate 104 may be removed to the side of the transport segment 50 in a direction generally perpendicularly relative to the lateral direction that the second and third guide wires 190, wire sleeves 108, and half-pin sleeves 106 were removed. The plate 104 may slide off the transport segment 50 and out from under the skin flap through the opening at the posterior incision 380 (see e.g., FIG. 5G). The plate 104 is removed by moving the channels 134 along the inserted half-pins 400. FIG. 5P illustrates the system after step 324, where the plate 104 of the template 100 (see e.g., FIG. 5O) has been removed, the half-pins 400 are inserted into the transport segment 50, the half-pins 400' are inserted into the base portion 52, and the distractor 200 is attached to the half pins 400, 400' (skin and subcutaneous tissue not shown).

Step 326 of the method 300 shown in FIG. 4 may include cutting the bone to free the transport segment 50. This may include cutting the remaining side of the transport segment 50. After the distractor 200 is attached to the half pins 400 in the transport segment 50 and the half pins 400' in the base portion 52, the remaining side or sides of the transport segment 50 may be cut. Once all of the sides are cut, the transport segment 50 may be moveable relative to the base portion 52 of the bone. In particular, the posterior side of the transport segment 50 may be cut. Because the skin flap is open towards the posterior side, the posterior side of the transport segment 50 may be easily accessible. In some embodiments, the wound may be closed around the transport segment 50. For example, the skin flap may be sutured to the neighboring skin.

Step 328 of the method 300 shown in FIG. 4 may include turning or rotating the actuator 206 in a first direction to move the transport segment 50 laterally away from the bone portion 52. As described above, the actuator 206 may include a knob 222 and a threaded rod 224 that are configured to move the upper beam 202 and the lower beam 204 towards each other or away from each other. When the half-pins 400' inserted into the base portion 52 are bi-cortical, the upper beam 202 may move upward relative to the lower beam 204 such that the half-pins 400 inserted into the transport segment 50 move upwards relative to the half-pins 400' inserted into the base portion 52. Thus, the transport segment 50 may be moved upward and away from the base portion 52 as the knob 222 of the actuator 206 is rotated in the first direction (i.e., distraction). FIG. 5Q illustrates the bone transport system after the transport segment 50 has been distracted according to step 328 (skin and subcutaneous tissue not shown). In the distracted position, the transport segment 50 has been moved upward away from the neighboring bone portion 52. Moreover, the upper beam 202 and lower beam 204 are spaced from one another and the threaded rod 224 and the support posts 228 are visible in the space between the beams 202, 204.

Step 330 of the method 300 shown in FIG. 4 may include turning the actuator 206 in a second direction to move the transport segment 50 laterally towards the base portion 52. This step may occur after or during treatment. When the half-pins 400' inserted into the base portion 52 are bi-cortical, the upper beam 202 may move downward relative to the lower beam 204 such that the half-pins 400 inserted into the transport segment 50 move downwards relative to the half-pins 400' inserted into the base portion 52. Thus, the transport segment 50 may be moved downward and towards the base portion 52 as the knob 222 of the actuator 206 is rotated in the second direction (i.e., contraction).

Figure 6A:
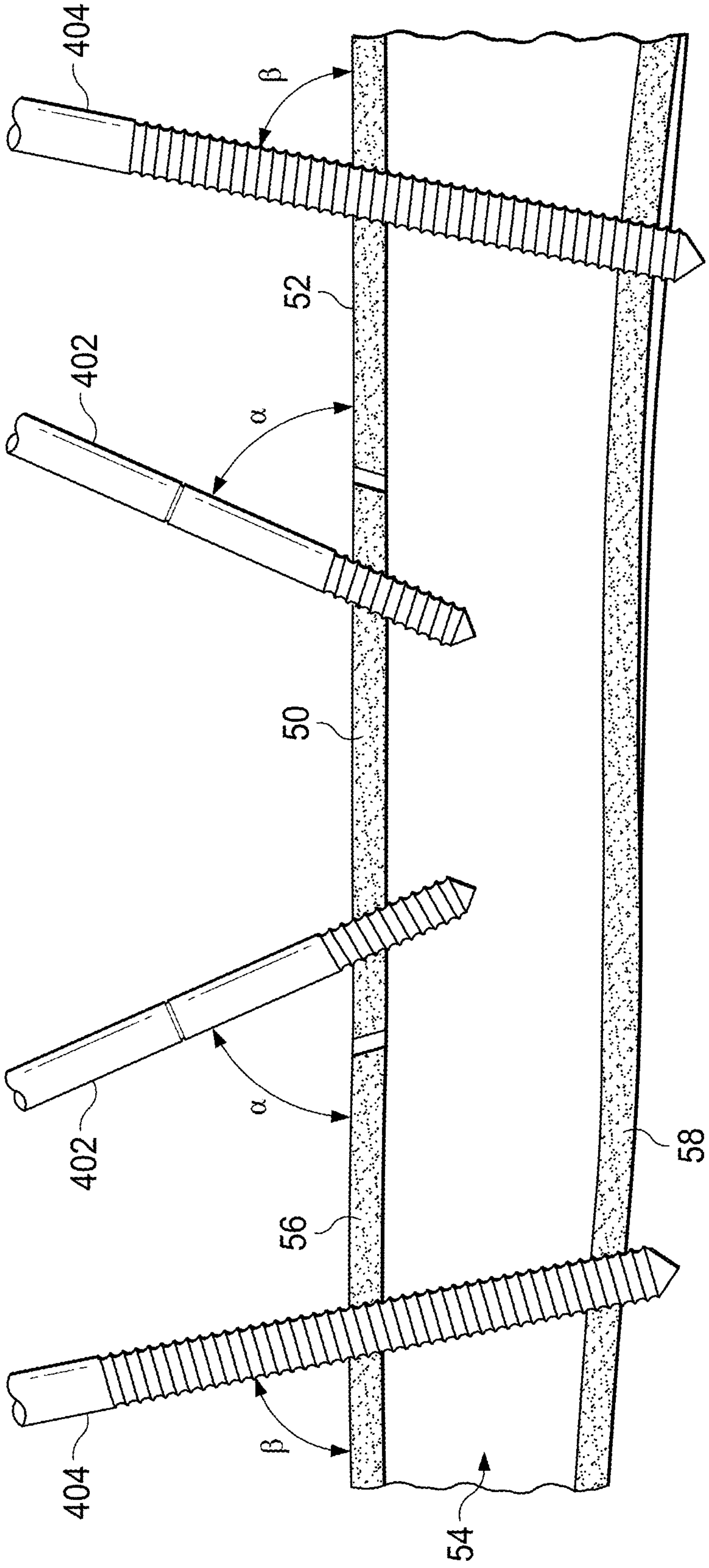
FIG. 6A is a diagram illustrating a cross-sectional view of a bone with half-pins inserted, according to some embodiments of the present disclosure.

FIG. 6A illustrates a diagram of a cross-sectional view of the bone with the half-pins inserted into the transport segment 50 and the base portion 52, according to some embodiments of the present disclosure. The bone may comprise an inner core of softer, medullary canal with bone marrow 54 surrounded by an outer layer of harder cortical bone 56, 58. In some cases, the half-pins 404 (referred to as half-pins 400' in FIGS. 1A-5Q) inserted into the base portion 52 of the bone may be bi-cortical, meaning they extend across the bone through both the proximal 56 and distal sections 58 of cortical bone. The half-pins 402 (referred to as half-pins 400 in FIGS. 1A-5Q) inserted into the transport segment 50 of the bone may be uni-cortical rather than bi-cortical. Thus, the uni-cortical half-pins 402 may extend partially through the bone and pass through only the proximal section 56 of the cortical bone. Thus, the transport segment 50 may not extend across the bone but may only extend partially through the bone. In this way, the transport segment 50 may be more easily moveable relative to the base portion 52. For example, the transport segment 50 may include a part of the proximal section 56 of the cortical bone and may not include bone marrow from the medullary cavity 54 or the distal section 58 of cortical bone.

In some cases, the half-pins 402 of the transport segment 50 are angled relative to the surface of the bone at an angle $\alpha$. Angle $\alpha$ may be any appropriate value. For example, a may be any angle within a range of 0 degrees to 90 degrees. In some embodiments, a may be 0, 5, 10, 15, 20, 25 30, 35, 40, 45, 50, 60, 70, 80 or 90 degrees. In some embodiments, the half-pins 402 may be at a 15-degree angle relative to the surface of the bone. In some cases, the half-pins 402 may be at the same or different angles relative to the surface of the bone. Although the half-pins 402 are shown as being angled inward towards each other, the half-pins 402 may also be angled outward away from each other or may be angled in the same direction.

In some cases, the half-pins 404 of the base portion 52 are angled relative to the surface of the bone at an angle $\beta$. Angle $\beta$ may be any appropriate value. For example, $\beta$ may be any angle within a range of 0 degrees to 90 degrees. In some embodiments, $\beta$ may be 0, 5, 10, 15, 20, 25 30, 35, 40, 45, 50, 60, 70, 80 or 90 degrees. In some embodiments, the half-pins 404 may be at a 15-degree angle relative to the surface of the bone. In some cases, the half-pins 404 may be at the same or different angles relative to the surface of the bone. Although the half-pins 404 are shown as being angled inward towards each other, the half-pins 404 may also be angled outward away from each other or may be angled in the same direction.

Figure 6B:
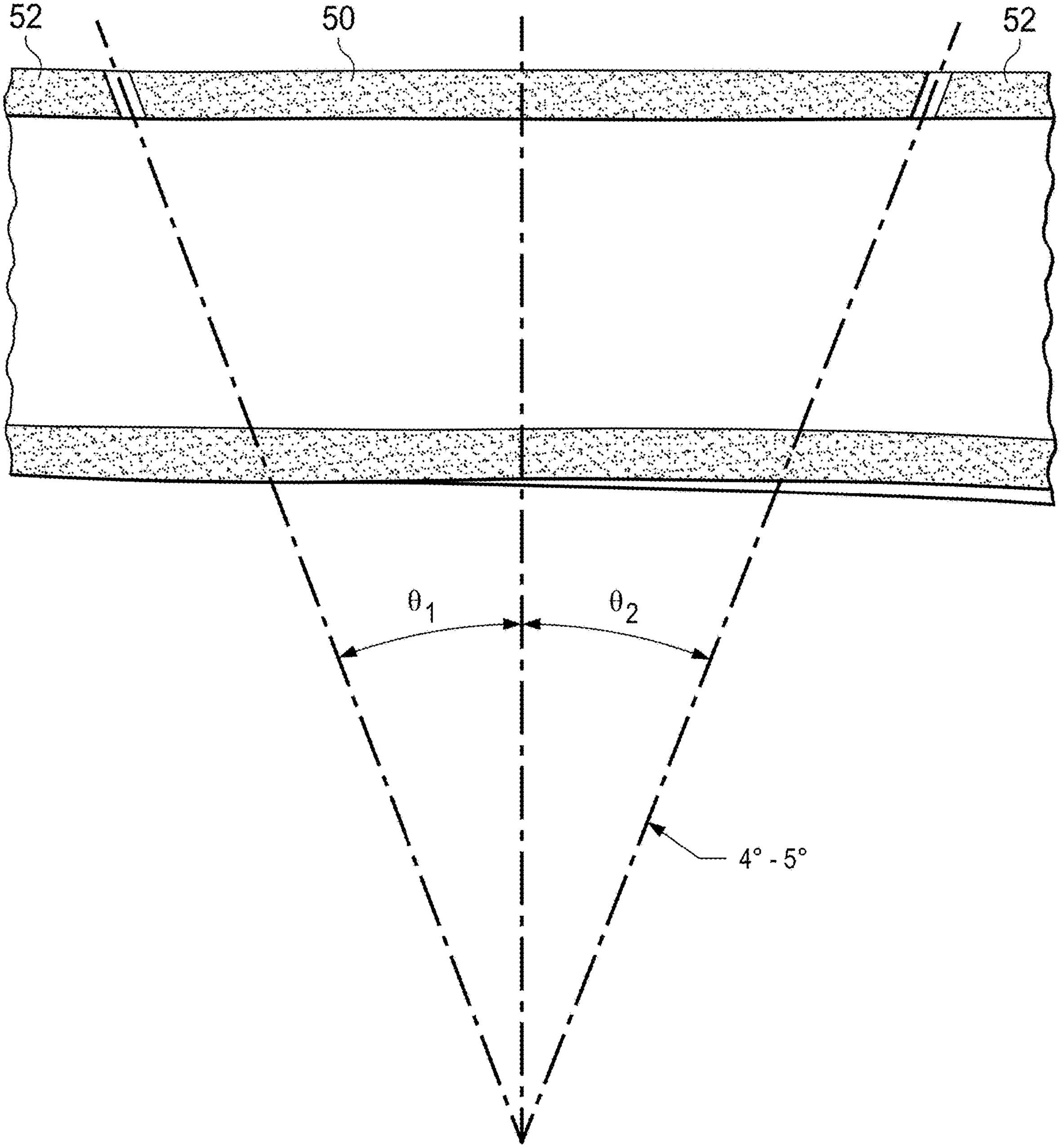
FIG. 6B is a diagram illustrating a side view of a transport segment of a bone, according to some embodiments of the present disclosure.

FIG. 6B illustrates a side view of the transport portion 50, according to one or more embodiments. As explained above, the plurality of holes around the perimeter of the plate 104 (see e.g., FIGS. 1A-1D) may be angled inward to create a transport segment 50 with a slight chamfer on the bottom such that the perimeter of the transport segment 50 is angled inward. The angle θ of the sides of the transport segment may be the same for all sides or one side may be angled at angle θ1 and one side may be angled at angle θ2. The sides may be angled at any suitable angle θ. For example, 01 and 02 may be any angle in a range of 0° to 15°. For example, angle θ1 and/or angle θ2 may be 0°, 1°, 2°, 3°, 4°, 5°, 6°, 7°, 8°, 9°, 10°, 11°, 12°, 13°, 14°, or 15°. This may prevent the transport segment 50 from interfering with the surrounding bone portion 52. The chamfer may also prevent the transport segment 50 from moving downward into the medullary cavity of the bone after being cut.

Figure 7A:
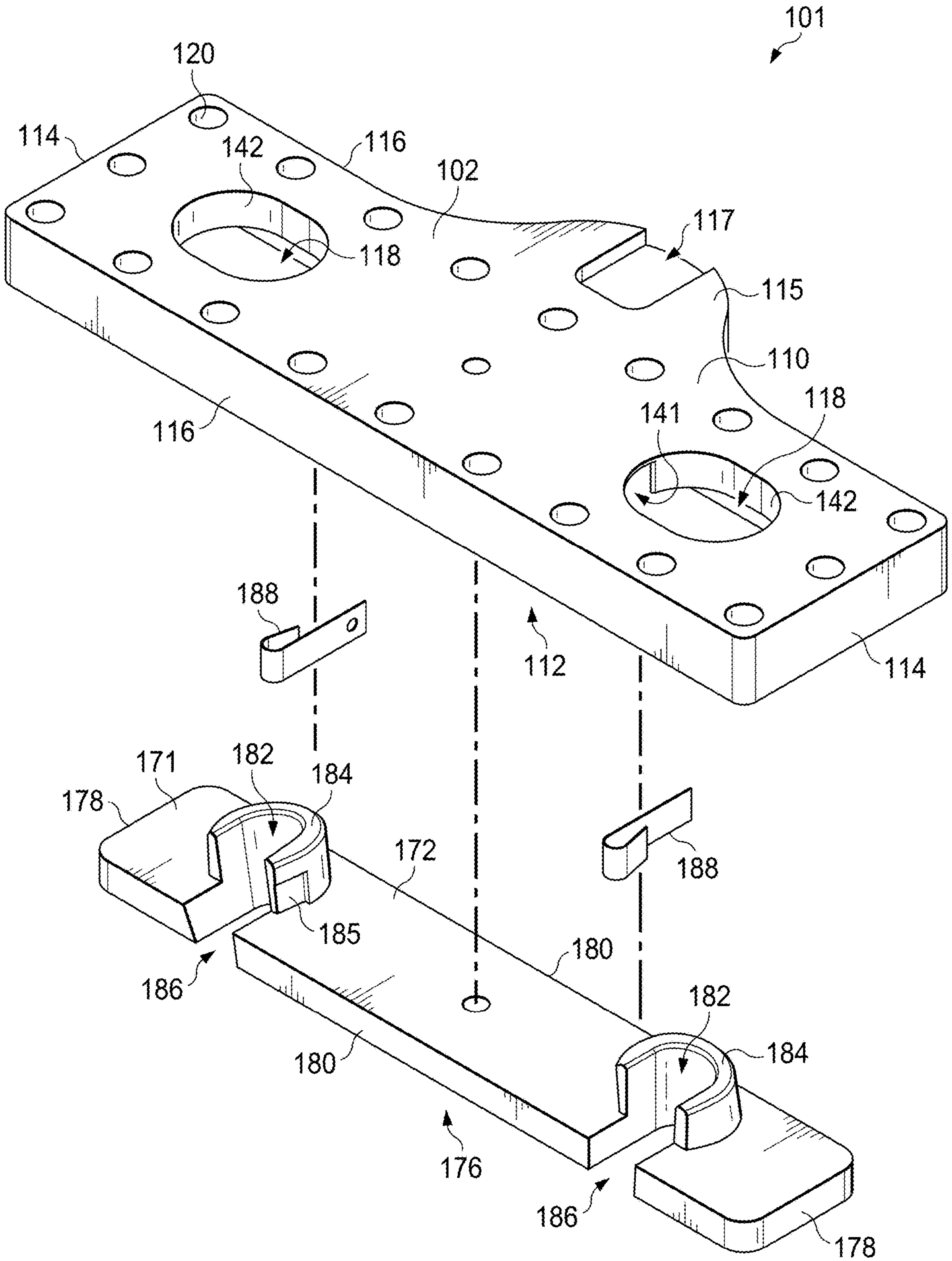
FIGS. 7A-7B illustrate another embodiment of a template, according to some embodiments of the present disclosure.
Figure 7B:
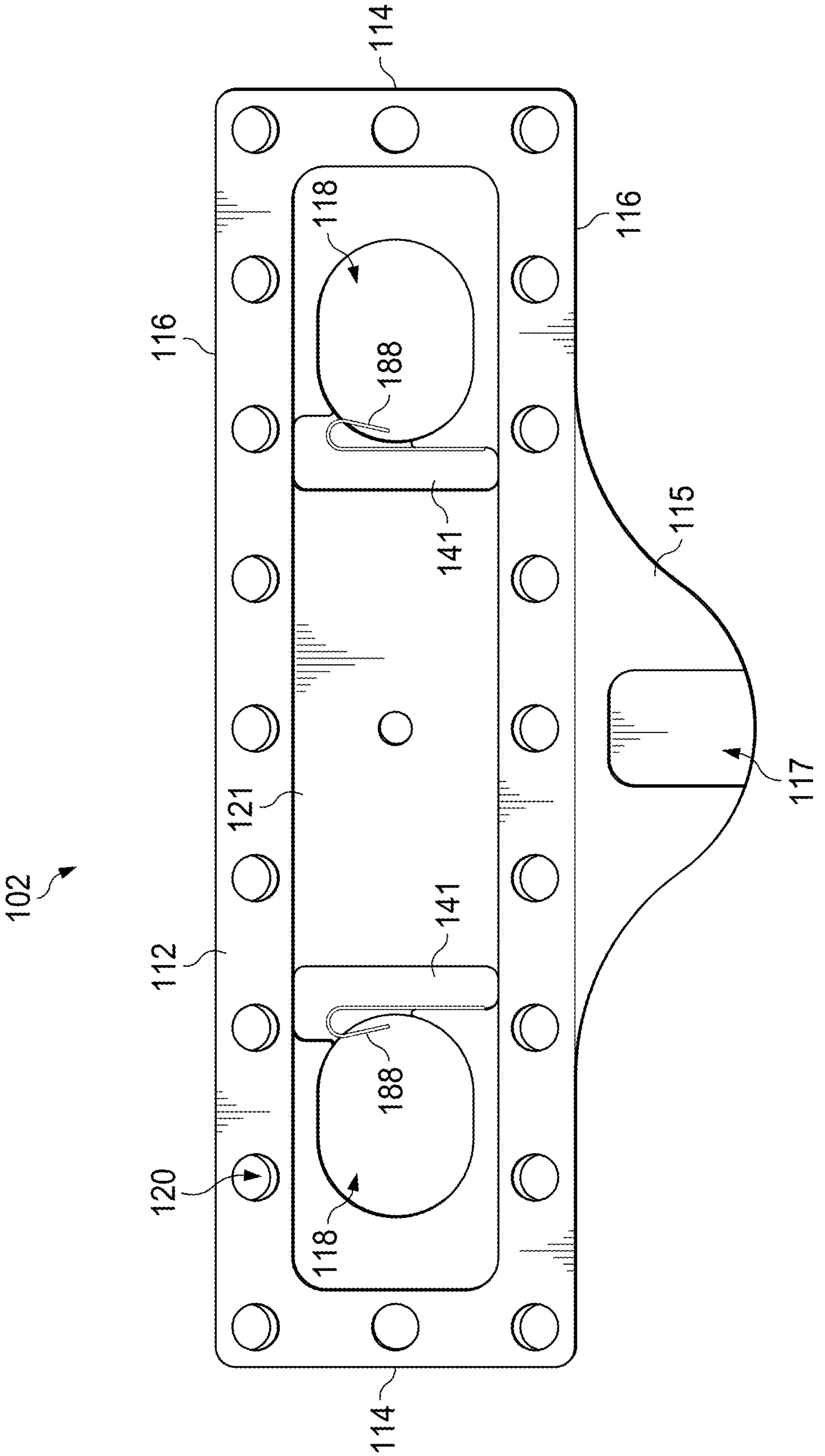

FIGS. 7A-7B illustrate another embodiment of a template 101 for use in a bone transport system. FIG. 7A is an exploded view of the template 101. FIG. 7B is a bottom view of the upper plate 102 with the clip 188 disposed therein. Unlike the template 100 illustrated in FIGS. 1A-1D, the template 101 illustrated in FIGS. 7A-7B includes two plates 102, 171: an upper plate 102 and a lower plate 171. The lower plate 171 illustrated in FIGS. 7A-7B may be substantially similar to the plate 104 illustrated in FIGS. 1A-1D. The lower plate 171 may have a top surface 172, a bottom surface 176, two ends 178, and two sides 180 disposed between the top surface 172 and the bottom surface 176. The plate includes two openings 182 that extend through the lower plate 171. The openings 182 may be generally circular. There may be channels 186 that extend from the openings 182 to one of the sides 180. However, the lower plate 171 illustrated in FIGS. 7A-7B may not have a tab 140. Moreover, unlike the openings 130 in the plate 104 illustrated in FIGS. 1A-1D, the openings 182 in the lower plate 171 illustrated in FIGS. 7A-7B are not threaded. Additionally, the extensions 184 of the lower plate 171 illustrated in FIGS. 7A-7B includes a recess 185 for a clip 188 that couples the upper plate 102 to the lower plate 171, which is not included in the plate 104 illustrated in FIGS. 1A-1D.

The upper plate 102 may have a top surface 110, a bottom surface 112, two ends 114, and two sides 116 disposed between the top surface 110 and the bottom surface 112 and between the two ends 114. The upper plate 102 may also include two elongate openings 118 that extend through the upper plate 102. The elongate openings 118 may be generally oblong, but, in some cases, may be any appropriate shape including, for example, rectangular, ovate, egg-shaped, elliptical, or ovoid.

The upper plate 102 may include a recess 121 defined in or sunken with respect to the bottom surface 112 of the upper plate 102. The recess 121 may be sized and shaped to fit the lower plate 171. In some cases, the lower plate 171 may fit into the recess 121 such that it is partially or completely disposed within the upper plate 102. The recess 121 may be centered on the bottom surface 112 or it may be disposed along an end 114 or side 116 of the bottom surface 112. In some embodiments, there is no recess 121 and the lower plate 171 is disposed below the upper plate 102. In some embodiments, the width and/or length of the lower plate 171 are smaller than the width and/or length of the upper plate 102. However, in other embodiments, the width and/or length of the lower plate 171 are larger than or equal to the width and/or length of the upper plate 102.

The upper plate 102 is configured as a drill guide having a plurality of holes 120 extending through the upper plate 102. The plurality of holes 120 may be arranged around a perimeter of the upper plate 102. In some cases, the plurality of holes 120 may be arranged around the recess 121 in the bottom surface 112 of the upper plate 102. In some embodiments, the plurality of holes 120 may only be arranged around three or fewer sides of the upper plate 102. The plurality of holes 120 in the upper plate may be used as guides for drilling holes in the bone to define a perimeter of the transport segment 50 (see e.g., FIG. 5P-5Q) of the bone, as described in more detail below. Thus, for the template illustrated in FIGS. 7A-7B, the T-shaped drill guide 500 illustrated in FIGS. 3A-3F may not be needed to drill holes around the transport segment 50.

The openings 182 of the lower plate 171 may be aligned with the elongate openings 118 of the upper plate 102. In some cases, the extensions 184 may extend into or through the elongate openings 118.

The upper plate 102 may also include a tab 115 that includes a recess 117 on the top and a recess 117 on the bottom. The recesses 117 may allow the physician to easily grip and/or maneuver the upper plate 102 using her hand or a tool (e.g., forceps) (not shown).

In some embodiments, the plurality of holes 120 around the perimeter of the template 100 may be angled inward to create a transport segment 50 with a slight chamfer on the bottom as shown in FIGS. 6A-6B. Thus, the plurality of holes 120 may be angled to create a transport segment 50 described in reference to FIGS. 6A-6B.

In some embodiments, the upper plate 102 may include projections 142 that project from the bottom surface 112 or the walls of the recess 121 into the recess 121. The projections 142 may define a recess or cavity 141 that is configured to fit the clip 188. Thus, the cavities 141 of the projections 142 141 on the upper plate 102 and the clip recess 185 of the extensions 184 on the lower plate 171 may only allow the lower plate 171 to be inserted in one orientation within the upper plate 102. In some embodiments, the clip 188 may allow the lower plate 171 to be snapped into and out of the recess 121 in the upper plate 102.

Figure 8A:
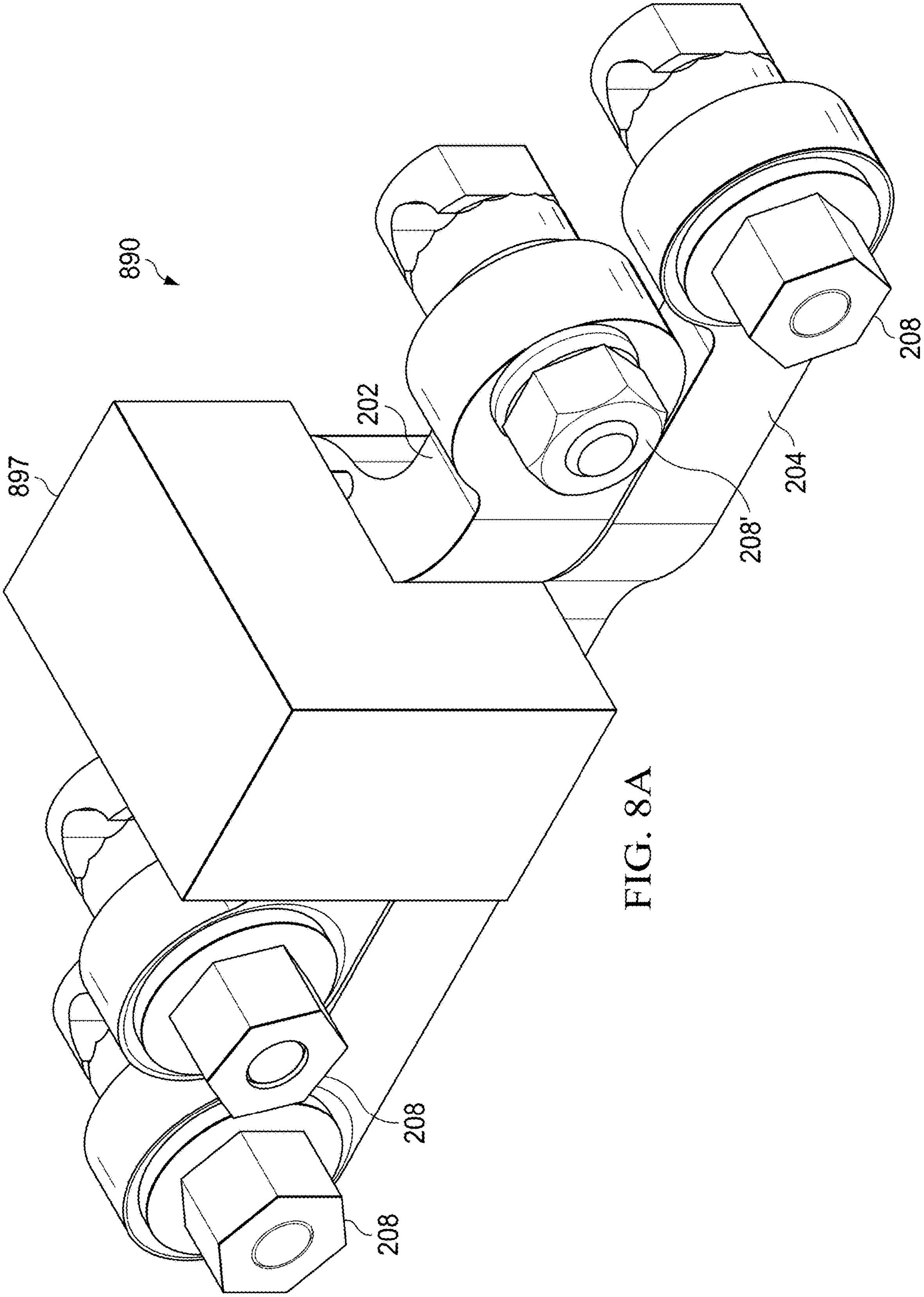
FIGS. 8A-8B illustrate another embodiment of a distractor, according to some embodiments of the present disclosure.
Figure 8B:
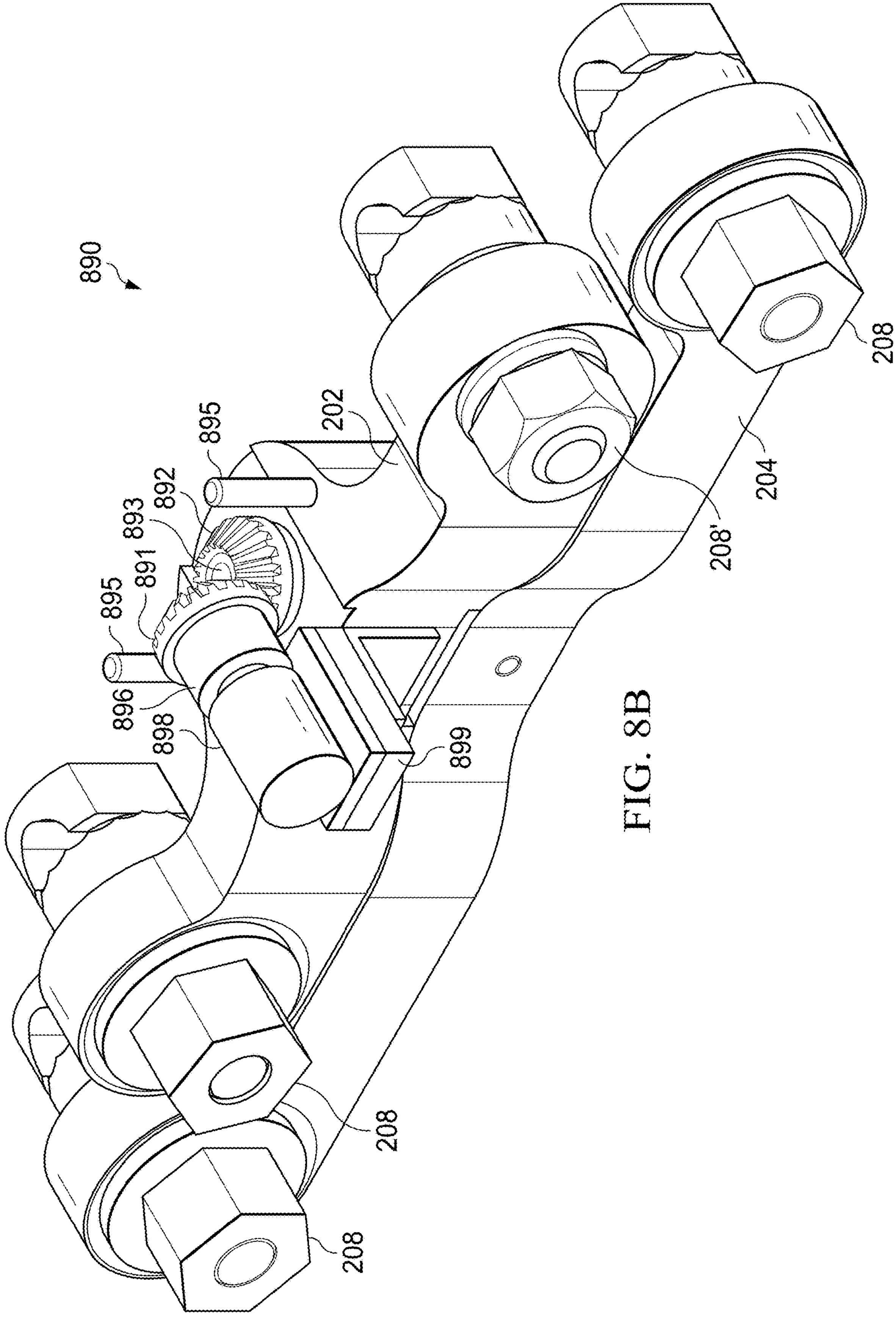

FIGS. 8A-8B illustrate another embodiment of a distractor 890, according to some embodiments of the present disclosure. FIG. 8A is a perspective view of the distractor 890 and FIG. 8B is a perspective view of the distractor 890 with the motor cover 897 removed. The distractor 890 illustrated in FIGS. 8A-8B is similar to the distractor 200 illustrated in FIGS. 2A-2D. The distractor 890 illustrated in FIGS. 8A-8B includes the same upper beam 202, lower beam 204, and half-pin holders 208, 208'. However, the distractor 890 in FIGS. 8A-8B uses a motorized actuation mechanism 896. The actuation mechanism illustrated in FIGS. 8A-8B uses a powered actuator 896 along with gears 891, 892 to actuate the distractor 890 between a distracted and contracted position. The actuator motor 896 has a drive shaft that includes a first gear 891. The actuator 896 may be powered in any suitable manner. For example, the actuator 896 may be a battery powered motor. The first gear 891 interconnects with a second gear 892. The second gear 892 is coupled to a threaded rod 893 that extends through the upper beam 202 and the lower beam 204. There may be support posts 895 on either side of the threaded rod 893 for stability. A motor cover 897 may be shaped and configured to cover the gears 891, 892 of the motor 896. The motor 896 may be operably coupled to a power source 898 and a processor circuit 899. The first gear 891 may be rotated using the power source 898. This may cause the second gear 892 to rotate, thus moving the threaded rod 893 upwards or downwards to move the upper 202 and lower 204 beams relative to each other. In some cases, rotating the first gear 891 in a first direction causes the upper 202 and lower 204 beams to move away from each other (distraction) and rotating the first gear 891 in a second direction may cause the upper 202 and lower 204 beams to move towards each other (contraction).

In some embodiments, the processor circuit 899 may include a processor and a memory storing computer-readable instructions. The processor circuit 899 may be operably coupled to the power source 898 and/or the motor 896 to control movement of the motor 896. For example, the processor circuit 899 may cause the first gear 891 to move in a first direction to cause distraction of the distractor 890 or in a second direction to cause contraction of the distractor 890.

The processor circuit 899 may include a wireless communication module that allows the processor circuit 899 to communicate wirelessly (for example, via Wi-Fi or Bluetooth) with a remote computer system. The computer system may send signals to the wireless communication module that control the power source 898 and/or motor 896.

In some embodiments, the transverse bone transport device may include a motorized engine with automatic controller of distraction/compression module potentially including sinusoidal rate of distraction and compression.

In some embodiments, the distractor 890 includes one or more sensors that measure, for example, at least one of blood volume, speed of blood flow, vascularization/neovascularization, strain, displacement, or any other suitable measurement. The processor circuit 899 may store the measurement data obtained by the one or more sensors and/or send the measurement data to a remote computer system. These measurement data may be analyzed by either the processor within the processor circuit 899 or by the computer system. For example, the processor circuit 899/computer system may compare the measurement data to stored program values and, based on such comparisons, control distraction, compression, and remodeling during consolidation. The measurement data and optionally other data (e.g., data about the patient) may be used to predict, determine, or suggest a treatment protocol. The power supply 898 and/or motor 896 may then be operated according to the treatment protocol. In some embodiments, artificial intelligence (AI) may be used to analyze the one or more measurements to predict a treatment protocol. The AI model can analyze the correlation between the physiological data detected on the patient and what is reported in clinical studies to propose, during the treatment, a variation of the treatment parameters different from what was planned to the physician. The AI model can also signal anomalies between the standard physiological parameters in this treatment and those detected on the patient. For example, if the level of oxygenation in surrounding soft tissues is higher than a set point, an AI module can adjust the rate of transport (e.g., 0.25 mm per day instead of standard 1 mm per day), which may lower the oxygenation levels to thereby provide better conditions for new vessel formation. Alternatively, in another example, the rate of transverse transport can be increased in the view of sensed enhanced new vessels formation adjacent to the transport segment, which increased daily movement of the transport segment may avoid premature bone consolidation between the transport segment and surrounding bone resulting in the interruption of bone transport.

In some embodiments, the transverse bone transport system may provide other treatments in addition to bone transport. For example, the bone transport system may include modules for delivery of chemical/biological agents. In some embodiments, the transverse bone transport device may include modules for mechanical stimulation of new vessels formation and increasing blood volume and flow.

Figure 9A:
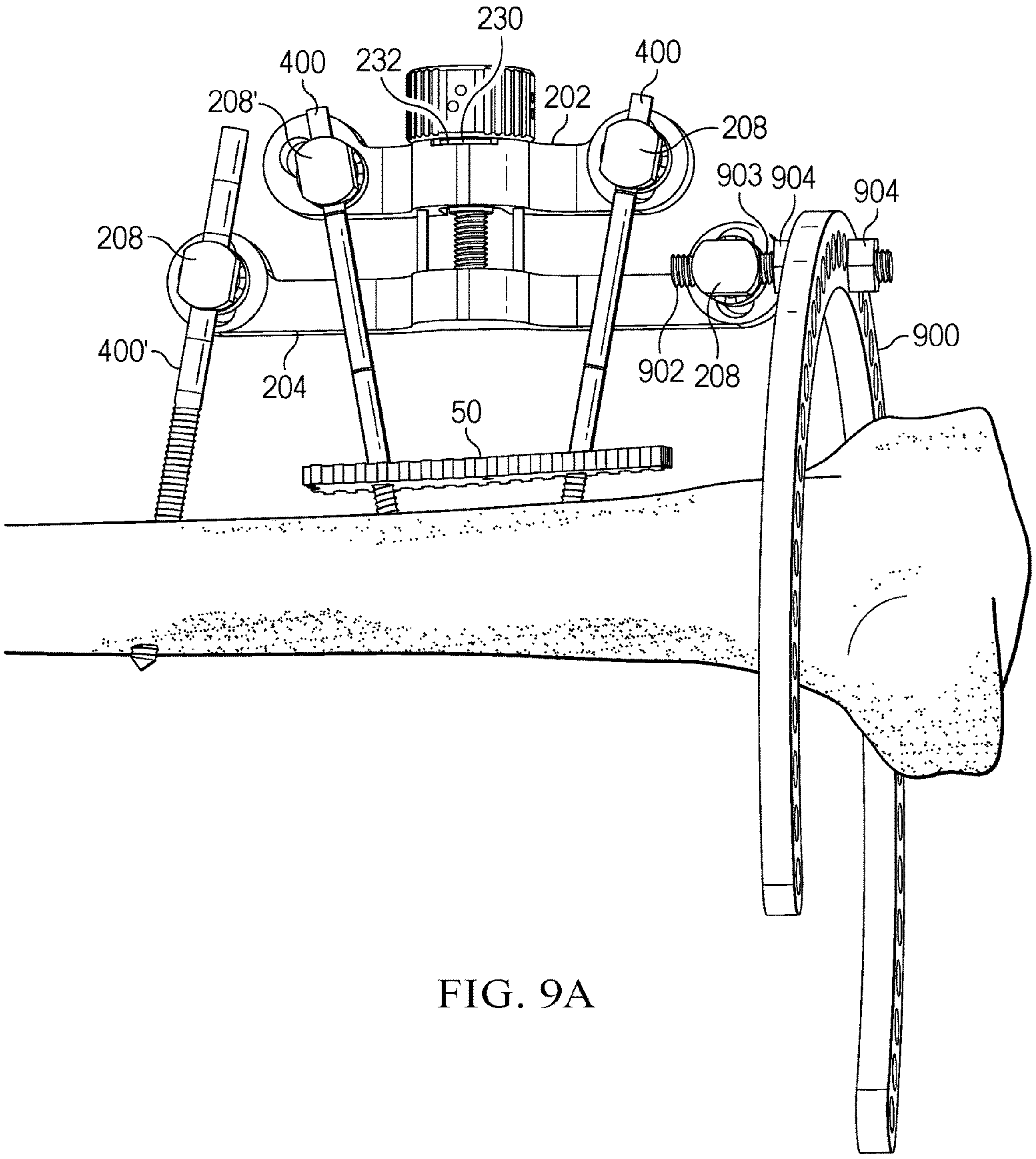
FIG. 9A illustrates the distractor shown in FIGS. 2A-2D connected to half pins and a ring, according to some embodiments of the present disclosure.

In some embodiments, a distractor may be attached to both the bone using half-pins 400 and to a ring 900 used in an external fixation system. FIG. 9A illustrates a distractor 200 coupled to the bone and to a ring 900. The distractor 200 in FIG. 9A is the same distractor 200 shown in FIGS. 2A-2D and, thus, the components/parts thereof will not be discussed in detail here (see discussion above). The upper beam 202 of the distractor 200 is attached to two half-pins 400 that are inserted into the transport segment 50. However, the lower beam 204 is only attached to one half-pin 400', which is inserted into the base portion 52 of the bone on one end of the transport segment 50. On the other end of the transport segment 50, the lower beam 204 is attached to an end of the ring connector 902. The ring connector 902 is attached to a ring 900 on the other end. In some embodiments, the ring connector 902 includes a threaded rod 903 and two bolts 904. The threaded rod 903 may be attached to the lower beam 204 of the distractor 200 by inserting the threaded rod 903 into the half-pin holder 208 and tightening the half-pin holder 208. The half-pin holder 208 may need to rotate more than it would to attach to a half-pin 400'. For example, the threaded rod 903 is oriented approximately parallel to the lower beam 204 in the illustrated embodiment. However, the half-pin holder 208 tightens around the threaded rod 903 in substantially the same way.

The threaded rod 903 may extend through a hole in the ring 900. The bolts 904 may threadedly engage the threaded rod 903 on either side of the ring 900. The bolts 904 may thus be tightened on either side of the ring 900 to secure the ring 900 between the bolts 904.

Once the distractor 200 is secured to the half-pins 400, 400' and to the ring 900, distraction and contraction of the distractor 200 works in the same way as described above in reference to FIGS. 2A-2D.

Figure 9B:
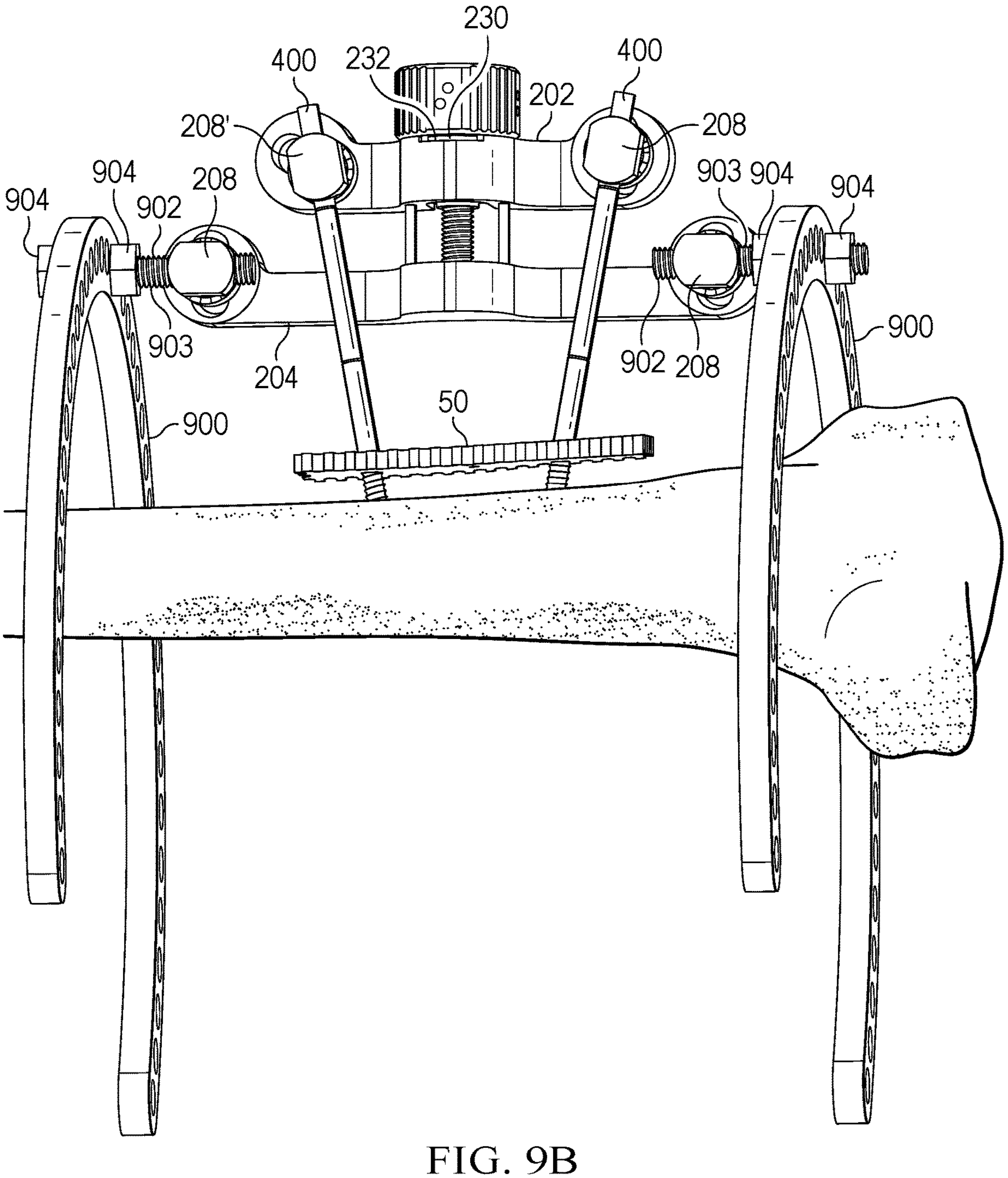
FIG. 9B illustrates the distractor shown in FIGS. 2A-2D connected to half pins and two rings, according to some embodiments of the present disclosure.

In some embodiments, a distractor 200 may be attached to both the transport segment 50 of the bone using half-pins 400 and to two rings 900 used in an external fixation system. FIG. 9B illustrates a distractor 200 coupled to the bone and to two rings 900. The distractor 200 in FIG. 9B is the same distractor 200 shown in FIGS. 2A-2D and, thus, the components/parts thereof will not be discussed in detail here (see discussion above). Moreover, the ring connector 902 illustrated in FIG. 9A is the same as the ring connectors 902 illustrated in FIG. 9B. Like in FIG. 9A, the upper beam 202 of the distractor 200 is coupled to two half-pins 400 inserted into the transport segment 50 of the bone. In FIG. 9B, both ends 212 of the lower beam 204 are coupled to rings 900 via ring connectors 902, as described above. Once the distractor 200 is secured to the half-pins 400 and to the rings 900, distraction and contraction of the distractor 200 works in the same way as described above in reference to FIGS. 2A-2D.

Although the distractor 200 shown in FIGS. 2A-2D is illustrated in FIGS. 9A-9B, it should also be understood that any suitable distractor, including the distractor 890 illustrated in FIGS. 8A-8B, could be used with one or more rings 900.

Figure 10A:
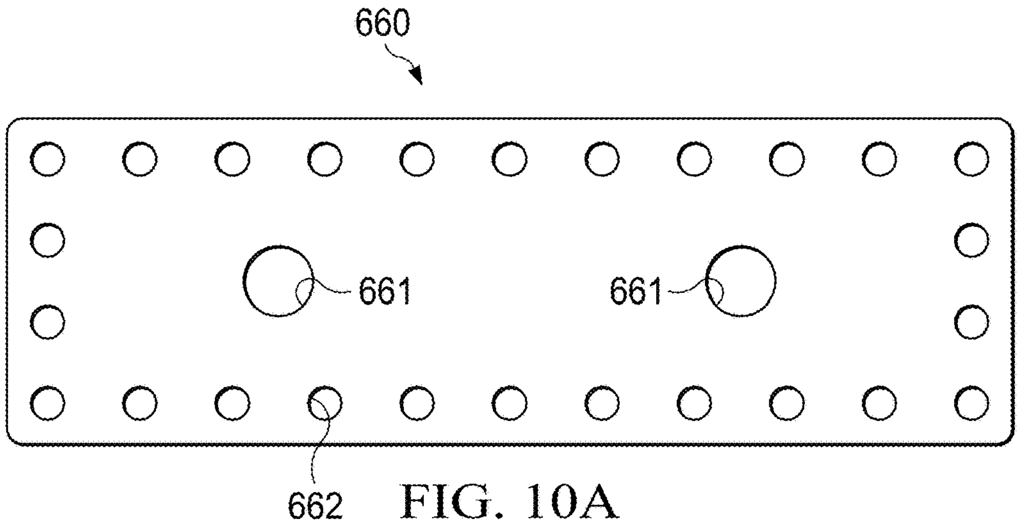
FIGS. 10A-10L illustrate various embodiments of templates, according to some embodiments of the present disclosure.

FIGS. 10A-10L illustrate various embodiments of templates, according to the embodiments described herein. FIG. 10A is an example of a template 660 having two openings 661 for fitting half-pins 400 and a plurality of holes 662.

Figure 10B:
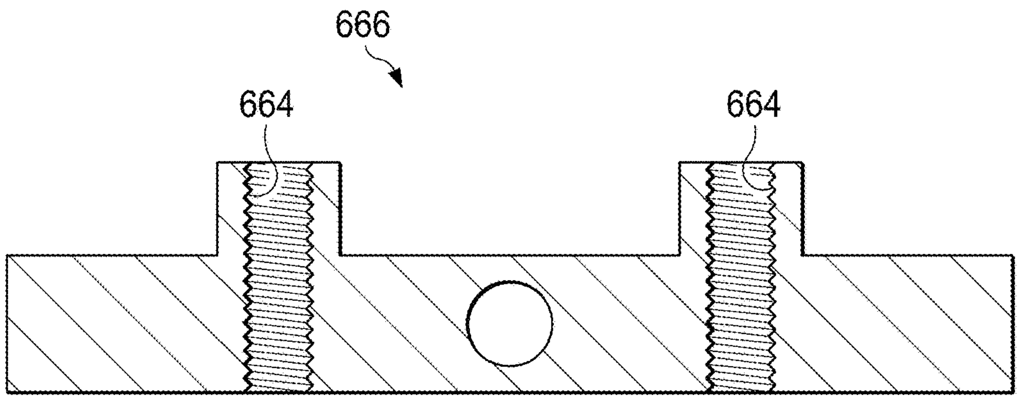
Figure 10C:
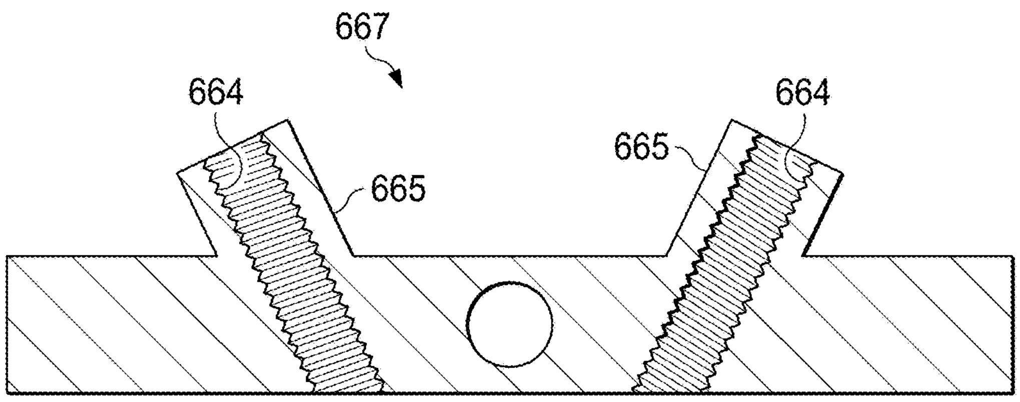

FIG. 10B is a side view of a template 666. The template 666 includes openings 664 that have extensions 665 extending upward from the top of the template 666. The openings 664 may not be angled and may be oriented generally perpendicular to the top and bottom surfaces of the template 666. FIG. 10C is an example of a template 667 that is similar to the template 666 shown in FIG. 10B. In the template 667 shown in FIG. 10C, the openings 664 are angled relative to the top and bottom surfaces of the template 667. The openings 664 may be angled outward towards the ends of the template 667.

Figure 10D:
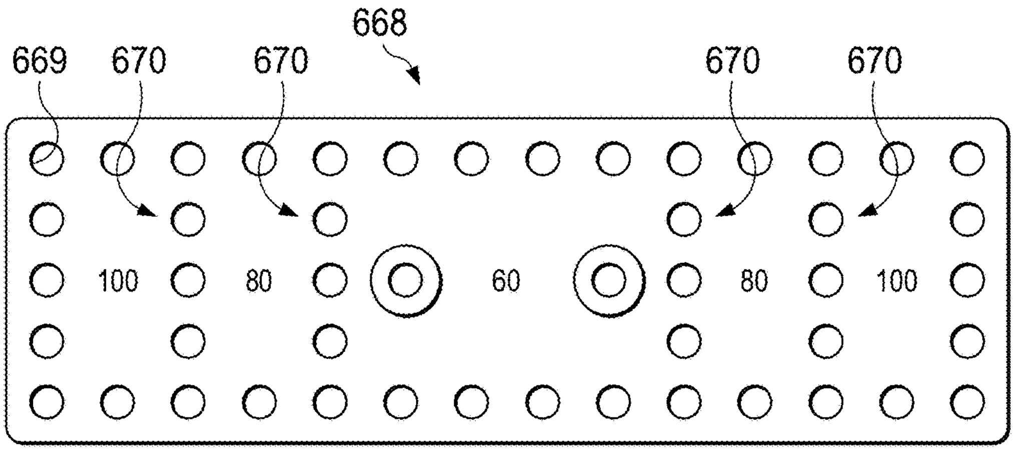
Figure 10E:
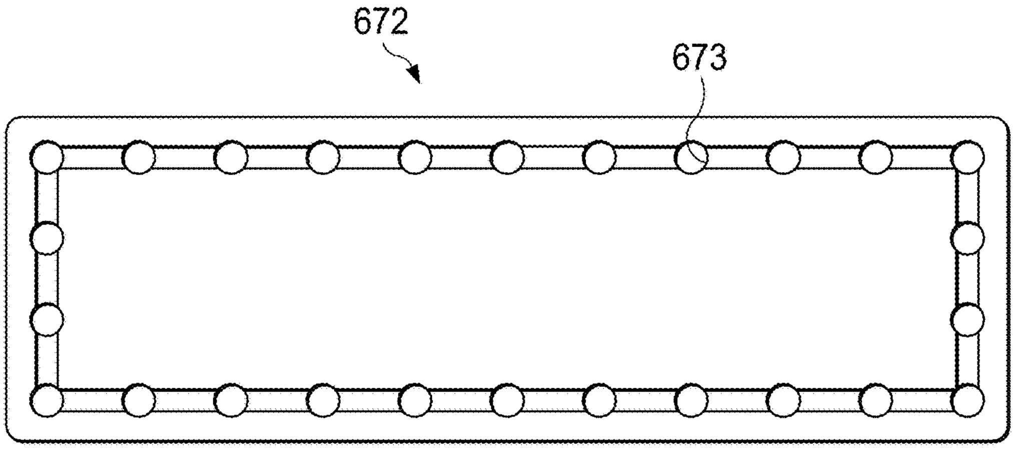

FIG. 10D illustrates an example of a template 668. The template 668 in FIG. 10D includes a plurality of holes 669 around the perimeter of the template 668 and rows of holes 670 from the holes 669 on one side to the holes on the other side of the template 668. This allows multiple sizes of transport segments 50 (see e.g., FIGS. 5P-5Q) to be measured and cut using a single template 668. FIG. 10E is an example of a template 672 including a plurality of holes 673 around the perimeter of the template 672. The plurality of holes 673 may be connected via a series of channels. Thus, the template 662 may be used to drill holes in the transport segment 50 and cut between the holes to form the transport segment 50 (see e.g., FIGS. 5P-5Q).

Figure 10F:
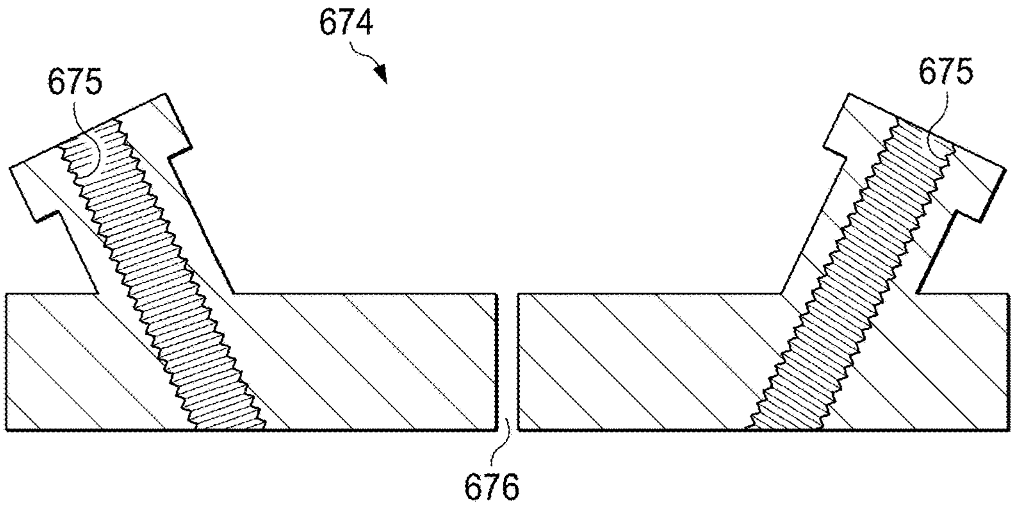
Figure 10G:
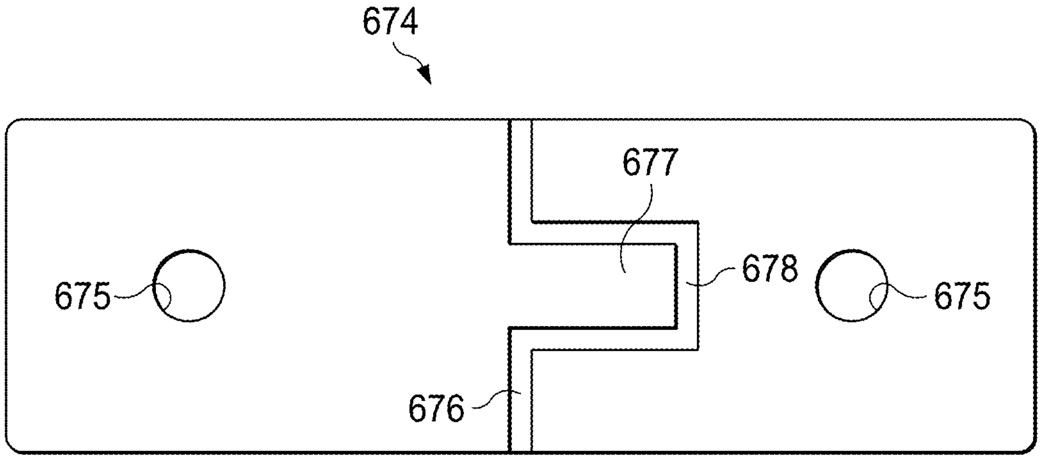
Figure 10H:
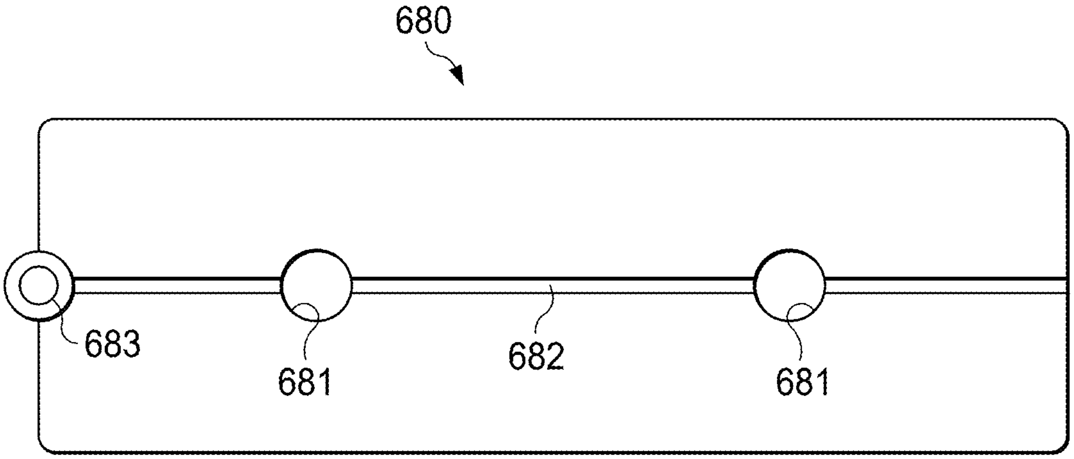

FIG. 10F is an example of a template 674 that is formed in two pieces. The template includes two angled openings 675 and a break 676 between the two openings 675. Thus, the opening 675 may be located on separate pieces of the template 674. The break 676 may pass from one side of the template 674 to the other. In some cases, the break 676 may be a straight line. FIG. 10G shows a top view of a template 674 where the break 676 is not a straight line. Instead, one piece comprises a projection 677 and one piece comprises a recess 678 that fits the projection 677. The shape of the template 674 in FIG. 10G may provide added stability and prevent the pieces moving relative to each other. FIG. 10H shows a two-piece template 680, where the openings 681 are disposed along the break 682 and a hinge 683 is located between the pieces on one end of the template 680.

Figure 10I:
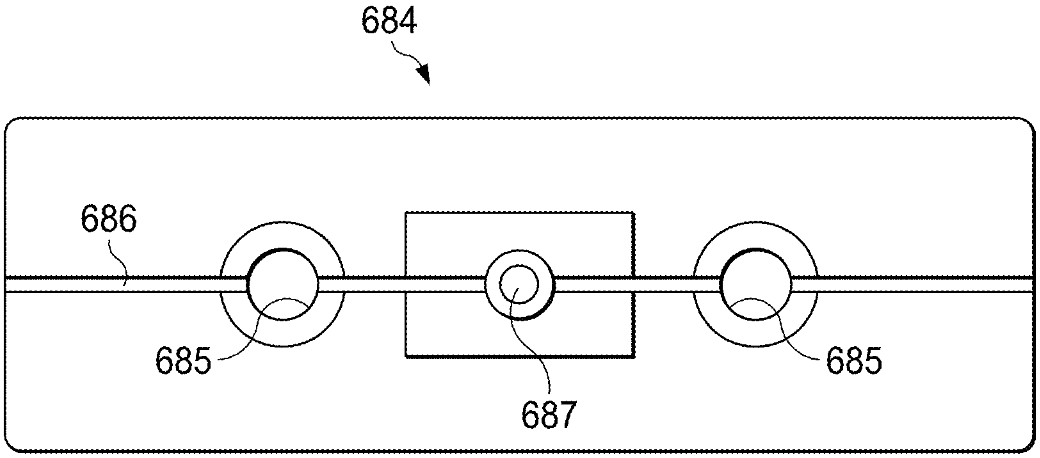

FIG. 10I is a top view of an example of a two-piece template 684. The template 684 includes two openings 685 disposed along a break 686 that extends from one end of the template 684 to the other. There is a hinge or locking plate 687 located along the break 686 that may allow the pieces to be disconnected from each other and move away from each other.

Figure 10J:
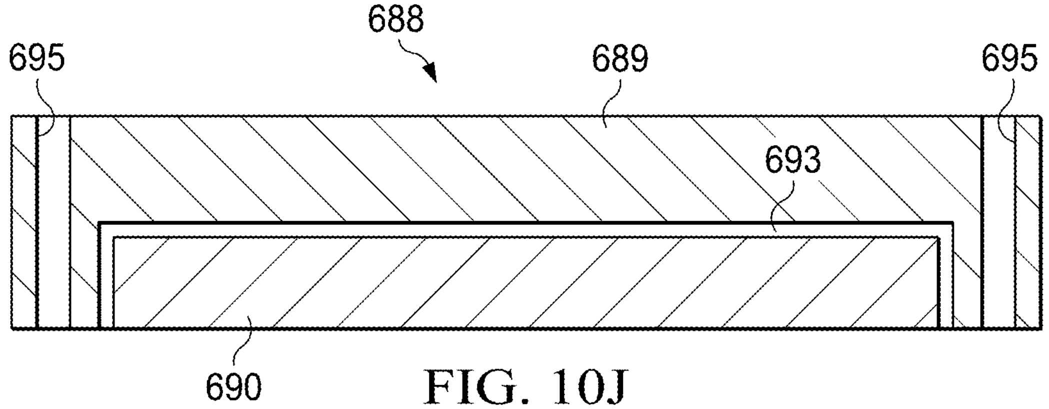
Figure 10K:
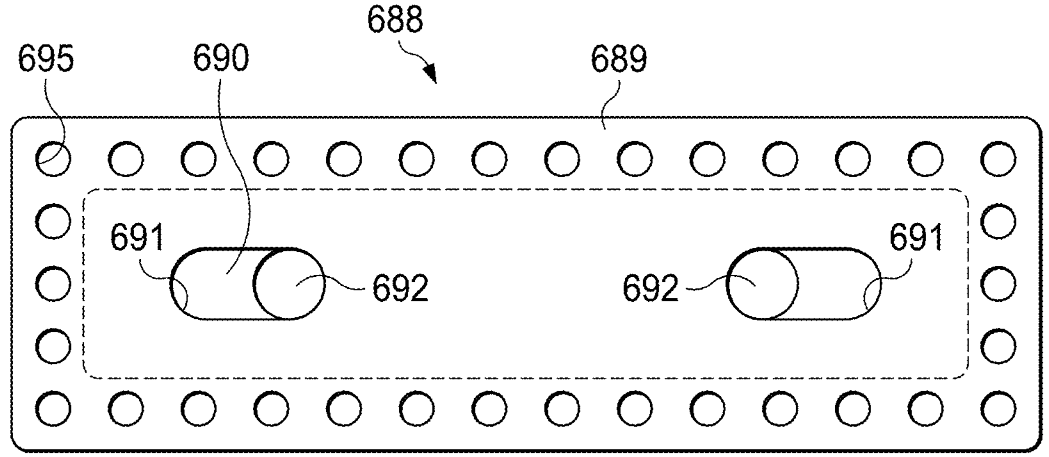
Figure 10L:
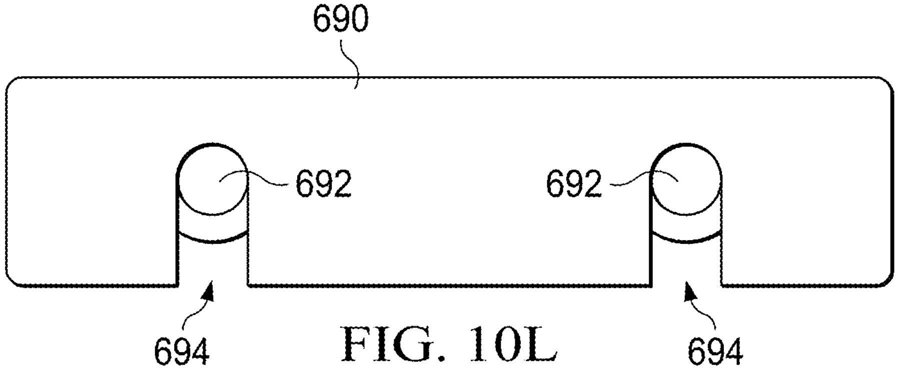

FIGS. 10J-10L illustrate a two-piece template 688, similar to the template 101 illustrated in FIGS. 7A-7B. The template 688 includes an upper plate 689 and a lower plate 690. The lower plate 690 may fit into a recess 693 in the bottom of the upper plate 689. The upper plate 689 includes two elongate openings 691 and the lower plate 690 includes two openings 692 that may not be elongate. The lower plate 690 may also include channels 694 that extend from the openings 692 to a side of the lower plate 690. The upper plate 689 may include a plurality of holes 695 arranged around the perimeter and around the recess 693.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages

What is claimed is:

1. A distractor for a transverse bone transport system, comprising:

a first beam comprising a first opening and a first moveable half-pin holder;

a second beam comprising a second opening and a second moveable half-pin holder, wherein a length of the second beam is larger than a length of the first beam, wherein the first moveable half-pin holder and the second moveable half-pin holder are longitudinally and radially displaced; and an actuator comprising:

a threaded rod disposed within the first opening of the first beam and the second opening of the second beam; and a knob operably coupled to the threaded rod, wherein the first beam carries either a plurality of recesses or a plurality of projections and the knob carries the other of the plurality of recesses or the plurality of projections, wherein the knob is biased against the first beam by a spring member such that the plurality of projections is disposed in the plurality of recesses to hold the knob in a first rotational position, wherein the knob is movable into a second rotational position by:

rotating the knob relative to the rod in a first direction to move the plurality of projections relative to the plurality of recesses to increase a distance between the first beam and the second beam and releasing the knob to hold the knob in the second rotational position; or rotating the knob relative to the threaded rod in a second direction to move the plurality of projections relative to the plurality of recesses to decrease a distance between the first beam and the second beam and releasing the knob to hold the knob in the second rotational position.

2. The distractor of claim 1, wherein the spring member includes a cylindrical body.

3. The distractor of claim 1, wherein the knob is biased against the first beam into a plurality of rotational positions comprising the first rotational position and the second rotational position, wherein each of the plurality of rotational positions of the knob is located a set angular distance from neighboring rotational positions.

4. The distractor of claim 3, wherein the set angular distance corresponds to a set lateral distance between the first beam and the second beam.

5. The distractor of claim 4, wherein the set lateral distance is 0.25 millimeters.

6. The distractor of claim 3, wherein the set angular distance is 90 degrees.

7. The distractor of claim 1, wherein the first moveable half-pin holder and the second moveable half-pin holder are configured to pivot between a plurality of angular positions.

8. The distractor of claim 7, wherein the first moveable half-pin holder is configured to hold a first pin, wherein the first moveable half-pin holder is configured to tighten around the first pin such that the first pin is held in a first angular position of the plurality of angular positions.

9. The distractor of claim 8, wherein the second moveable half-pin holder is configured to hold a second pin, wherein the second moveable half-pin holder is configured to tighten around the second pin such that the second pin is held in a second angular position of the plurality of angular positions.

10. The distractor of claim 9, wherein the first angular position and the second angular position are different.

11. The distractor of claim 1, wherein the threaded rod is threadedly received in the second beam such that the actuator is configured to move the first beam relative to the second beam.

12. The distractor of claim 1, further comprising a support post coupled to at least one of the first beam or the second beam and disposed proximate to the threaded rod.

13. The distractor of claim 1, wherein the threaded rod is threadedly received in the first beam such that the actuator is configured to move the second beam relative to the first beam.

14. The distractor of claim 1, further comprises a motor configured to rotate the actuator.

15. The distractor of claim 1, wherein the first moveable half-pin holder is configured to hold a first half-pin attached to a transport segment of a bone.

16. The distractor of claim 15, wherein the second moveable half-pin holder is configured to hold a second half-pin inserted into the bone proximate to a transport segment.

17. The distractor of claim 16, wherein the first half-pin is configured to be disposed at a first angle relative to an axis transverse to the bone and the second half-pin is configured to be disposed at a second angle relative to the axis, and wherein the first angle and the second angle are different and non-zero.

18. The distractor of claim 1, wherein the second moveable half-pin holder is configured to couple to a connector coupled to a ring of an external fixation device.

19. A distractor for a bone transport system, comprising:

a first portion comprising at least two openings, each opening being configured to receive a screw for holding a half-pin, wherein the first portion carries a first structure;

a second portion comprising at least two openings, each opening being configured to receive a screw for holding a half-pin;

an actuator coupled to the first portion and the second portion that moves the first portion relative to the second portion, the actuator comprising:

a threaded rod extending through the first portion;

a knob operably coupled to the threaded rod such that rotation of the knob moves the threaded rod, wherein the knob carries a second structure complementary to the first structure; and a spring that biases the knob towards the first portion such that the second structure cooperates with the first structure to hold the knob in one of a plurality of discrete positions of the first portion relative to the second portion, wherein the knob is rotatable into another of the plurality of discrete positions. thereby moving the threaded rod to translate at least one of the first portion or the second portion along the threaded rod towards or away from each other.

20. The distractor of claim 19, wherein the first structure is at least one of a projection or a recess and the second structure is the other of the at least one of a projection or a recess, wherein the spring is configured to bias the projection into the recess after rotation of the knob.

21. The distractor of claim 19, wherein the actuator further comprises a sleeve adapter receivable within the knob and having an opening for receiving the threaded rod.

22. The distractor of claim 21, wherein the spring is disposed between the sleeve adapter and the knob.

23. The distractor of claim 19, wherein the knob is configured to rotate the threaded rod:

in a first direction to move the first portion laterally outward; and in a second direction to move the first portion laterally inward.

24. The distractor of claim 19, wherein each discrete position of the plurality of discrete positions of the first portion relative to the second portion is a same lateral distance from a neighboring discrete position.

25. The distractor of claim 19, further comprising at least one support post extending between the first portion and the second portion.

26. The distractor of claim 19, wherein the screw for holding the half-pin is configured to hold the half-pin in a plurality of angular positions.

27. A distractor for a bone transport system, comprising:

a first beam having a longitudinal axis disposed at a horizontal angle, comprising:

a first slot proximate a first end of the first beam and disposed at a first angle;

a second slot proximate a second end of the first beam and disposed at a vertical angle approximately perpendicular to the longitudinal axis, wherein the first angle is disposed between the vertical angle and the horizontal angle;

a first half-pin holder slidable within the first slot; and a second half-pin holder slidable within the second slot;

a second beam comprising:

a third slot proximate a first end of the second beam and disposed at the vertical angle;

a fourth slot proximate a second end of the second beam and disposed at the vertical angle;

a third half-pin holder slidable within the third slot; and a fourth half-pin holder slidable within the fourth slot, wherein a first length of the first beam is smaller than a second length of the second beam; and an actuator comprising:

a rod comprising a threaded portion extending through the first beam and the second beam; and a knob coupled to the rod, wherein rotation of the knob causes rotation of the rod to move at least one of the first beam or the second beam vertically.

28. The distractor of claim 27, wherein the first half-pin holder is different than the second half-pin holder, the third half-pin holder, and the fourth half-pin holder, and wherein the second half-pin holder, the third half-pin holder, and the fourth half-pin holder are the same.

29. The distractor of claim 27, wherein the first angle is approximately 45 degrees relative to the longitudinal axis.

30. The distractor of claim 27, wherein the first half-pin holder and the second half-pin holder are configured to hold half-pins attached to a transport segment of a bone and the third half-pin holder and the fourth half-pin holder are configured to hold half-pins attached to the bone proximate the transport segment.

31. A distractor for a bone transport system, comprising:

a first beam comprising a first slot disposed at a first angle and a first half-pin holder slidable within the first slot;

a second beam comprising a second slot disposed at a second angle and a second half-pin holder slidable within the second slot, wherein a first length of the first beam is smaller than a second length of the second beam, and wherein the first angle and the second angle are different; and an actuator comprising:

a rod comprising a threaded portion extending through the first beam and the second beam; and a knob coupled to the rod, wherein rotation of the knob causes movement of the rod to thereby move at least one of the first beam or the second beam along an axis transverse to a bone of a patient, wherein the first beam further comprises a third slot disposed at a third angle and a third half-pin holder slidable within the third slot, wherein the second beam further comprises a fourth slot disposed at a fourth angle and a fourth half-pin holder slidable within the fourth slot, wherein the first angle is different than the third angle and the fourth angle, wherein the second angle, the third angle, and the fourth angle are the same, wherein the first half-pin holder is different than the second half-pin holder, the third half-pin holder, and the fourth half-pin holder, and wherein the second half-pin holder, the third half-pin holder, and the fourth half-pin holder are the same.

* * * * *